United States Patent
Han et al.

(10) Patent No.: US 7,507,730 B2
(45) Date of Patent: Mar. 24, 2009

(54) SUBSTITUTED PYRAZOLO[1,5-A]PYRIMIDINES AS POTASSIUM CHANNEL ACTIVATORS

(75) Inventors: Wei Han, Yardley, PA (US); Zilun Hu, Jamison, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 143 days.

(21) Appl. No.: 11/511,154

(22) Filed: Aug. 28, 2006

(65) Prior Publication Data

US 2007/0203157 A1    Aug. 30, 2007

Related U.S. Application Data

(60) Provisional application No. 60/712,497, filed on Aug. 30, 2005.

(51) Int. Cl.
| | |
|---|---|
| C07D 487/04 | (2006.01) |
| C07D 291/06 | (2006.01) |
| A61K 31/519 | (2006.01) |
| A61K 31/541 | (2006.01) |
| C07D 413/12 | (2006.01) |
| A61K 31/5355 | (2006.01) |
| A61P 25/06 | (2006.01) |
| A61P 9/06 | (2006.01) |
| A61P 25/08 | (2006.01) |
| A61P 1/04 | (2006.01) |
| A61P 11/08 | (2006.01) |

(52) U.S. Cl. .............. 514/222.2; 514/234.2; 514/259.3; 544/2; 544/117; 544/281

(58) Field of Classification Search .................. 544/281, 544/117, 2; 514/259.31, 234.2, 259.3, 222.2
See application file for complete search history.

(56) References Cited

U.S. PATENT DOCUMENTS 5,612,359 A    3/1997    Murugesan (Continued)

FOREIGN PATENT DOCUMENTS

WO    WO 01/40231 A1    6/2001

OTHER PUBLICATIONS

Balser, J.R. et al., "Suppression of Time-Dependent Outward Current in Guinea Pig Ventricular Myocytes: Actions of Quinidine and Amiodarone", Circulation Research, vol. 69, No. 2, pp. 519-529 (1991).

Bowlby, M.R. et al., "Block of Cloned Voltage-Gated Potassium Channels by the Second Messenger Diacylglycerol Independent of Protein Kinase C", Journal of Neurophysiology, vol. 73, No. 6, pp. 2221-2229 (1995).

(Continued)

*Primary Examiner*—Brenda L Coleman
*Assistant Examiner*—Susanna Moore
(74) *Attorney, Agent, or Firm*—Terence J. Bogie; Burton Rodney

(57) ABSTRACT

Novel heterocyclic dihydropyrimidine compounds useful as inhibitors of potassium channel function (especially inhibitors of the $K_v1$ subfamily of voltage gated $K^+$ channels, especially inhibitors $K_v1.5$ which has been linked to the ultra-rapidly activating delayed rectifier, which have the structure

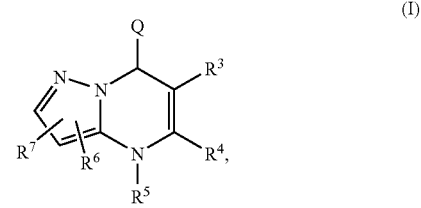

(I)

stereoisomers including enantiomers thereof and diastereomers thereof, or a pharmaceutically acceptable salt thereof, wherein Q is alkyl, substituted alkyl, cycloalkyl, substituted cycloalkyl, cycloheteroalkyl, substituted cycloheteroalkyl or

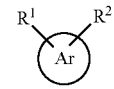

which is aryl, substituted aryl, heteroaryl or substituted heteroaryl; $R^3$ is

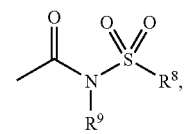 a)

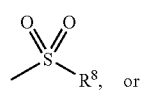

b)

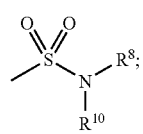

c)

wherein $R^1$, $R^2$, $R^4$, $R^5$, $R^6$, $R^7$, $R^8$, $R^9$ and $R^{10}$ are defined herein.

Methods of using such compounds in the prevention and treatment of arrhythmia and $I_{Kur}$-associated conditions, and pharmaceutical compositions containing such compounds are also provided.

14 Claims, No Drawings

U.S. PATENT DOCUMENTS

| | | | |
|---|---|---|---|
| 5,631,282 | A | 5/1997 | Goetz |
| 5,670,504 | A | 9/1997 | Bochis et al. |
| 5,679,705 | A | 10/1997 | Baker et al. |
| 5,696,156 | A | 12/1997 | Baker et al. |
| 6,043,265 | A | 3/2000 | Murugesan et al. |

OTHER PUBLICATIONS

Chandy, K.G. et al., Chapter 1: "Voltage-Gated Potassium Channel Genes", Handbook of Receptors and Channels: Ligand- and Voltage-Gated Ion Channels, CRC Press, Inc., publ., North, R.A., ed., pp. 1-71 (1995).

Chandy, K.G. et al., "Voltage-Gated Potassium Channels are Required for Human T Lymphocyte Activation", J. Exp. Med., vol. 160, pp. 369-385 (1984).

DeCoursey, T.E. et al., "Voltage-gated $K^+$ channels in human T lymphocytes: a role in mitogenesis?", Nature, vol. 307, pp. 465-468 (1984).

Doupnik, C.A. et al., "The inward rectifier potassium channel family", Current Opinion in Neurobiology, vol. 5, pp. 268-277 (1995).

Fedida, D. et al., "Identity of a Novel Delayed Rectifier Current From Human Heart With a Cloned $K^+$ Channel Current", Circulation Research, vol. 73, No. 1, pp. 210-216 (1993).

Greene, T.W. et al., Protective Groups in Organic Synthesis, Second Edition, John Wiley & Sons, Inc., publ., pp. ix-x (table of contents) (1991).

Grissmer, S. et al., "Pharmacological Characterization of Five Cloned Voltage-Gated $K^+$ Channels, Types Kv1.1, 1.2, 1.3, 1.5, and 3.1, Stably Expressed in Mammalian Cell Lines", Molecular Pharmacology, vol. 45, pp. 1227-1234 (1994).

Hondeghem, L.M., "Development of Class III Antiarrhythmic Agents", Journal of Cardiovascular Pharmacology, vol. 20, Suppl. 2, pp. S17-S22 (1992).

Kalman, K. et al., "Genomic Organization, Chromosomal Localization, Tissue Distribution, and Biophysical Characterization of a Novel Mammalian *Shaker*-related Voltage-gated Potassium Channel, Kv1.7", The Journal of Biological Chemistry, vol. 273, No. 10, pp. 5851-5857 (1998).

Leonard, R.J. et al., "Selective blockers of voltage-gated $K^+$ channels depolarize human T lymphocytes: Mechanism of the antiproliferative effect of charybdotoxin", Proc. Natl. Acad. Sci. USA, vol. 89, pp. 10094-10098 (1992).

Lins, C.S. et al., "Voltage-gated Potassium Channels Regulate Calcium-dependent Pathways Involved in Human T Lymphocyte Activation", J. Exp. Med., vol. 177, pp. 637-645 (1993).

Nademanee, K., "The Amiodarone Odyssey", Journal of the American College of Cardiology, vol. 20, No. 5, pp. 1063-1065 (1992).

Petersen, K.R. et al., "Expression environment determines $K^+$ current properties: Kv1 and Kv4 α-subunit-induced $K^+$ currents in mammalian cell lines and cardiac myocytes", Pflügers Arch.—Eur. J. Physiol., vol. 437, pp. 381-392 (1999).

Roden, D.M., "Current Status of Class III Antiarrhythmic Drug Therapy", The American Journal of Cardiology, vol. 72, pp. 44B-49B (1993).

Sanguinetti, M.C. et al., "Two Components of Cardiac Delayed Rectifier $K^+$ Current: Differential Sensitivity to Block by Class III Antiarrhythmic Agents", J. Gen. Physiol., vol. 96, pp. 195-215 (1990).

Singh, B.N. et al., "A third class of anti-arrhythmic action. Effects on atrial and ventricular intracellular potentials, and other pharmacological actions on cardiac muscle, of MJ 1999 and AH 3474", Br. J. Pharmacol., vol. 39, pp. 675-687 (1970).

Singh, B.N. et al., "The effect of amiodarone, a new anti-anginal drug, on cardiac muscle", Br. J. Pharmacol., vol. 39, pp. 657-667 (1970).

Snyders, D.J. et al., "A Rapidly Activating and Slowly Inactivating Potassium Channel Cloned from Human Heart: Functional Analysis after Stable Mammalian Cell Culture Expression", J. Gen. Physiol., vol. 101, pp. 513-543 (1993).

Swanson, R. et al., "Cloning and Expression of cDNA and Genomic Clones Encoding Three Delayed Rectifier Potassium Channels in Rat Brain", Neuron, vol. 4, pp. 929-939 (1990).

Vaughan Williams, E.M., Chapter 20: "Classification of anti-arrhythmic drugs", Symposium on Cardiac Arrhythmias, Elsinore, Denmark, Apr. 23-25, 1970, AB Astra, Södertälje, Sweden, publ., Sandøe, E. et al., eds., pp. 449-472 (1970).

Wang, Z. et al., "Sustained Depolarization-Induced Outward Current in Human Atrial Myocytes: Evidence for a Novel Delayed Rectifier $K^+$ Current Similar to Kv1.5 Cloned Channel Currents", Circulation Research, vol. 73, No. 6, pp. 1061-1076 (1993).

Witzeman, J.S. et al., "Transacetoacetylation with *tert*-Butyl Acetoacetate: Synthetic Applications", J. Org. Chem., vol. 56, No. 5, pp. 1713-1718 (1991).

Yang, T. et al., "Mechanism of block of a human cardiac potassium channel by terfenadine racemate and enantiomers", British Journal of Pharmacology, vol. 115, pp. 267-274 (1995).

SUBSTITUTED PYRAZOLO[1,5-A]PYRIMIDINES AS POTASSIUM CHANNEL ACTIVATORS

The present application takes priority from U.S. provisional application No. 60/712,497 filed Aug. 30, 2005, the disclosure of which is incorporated herein by reference.

FIELD OF THE INVENTION

The present invention provides for heterocyclic dihydropyrimidine compounds useful as inhibitors of potassium channel function (especially inhibitors of the $K_v1$ subfamily of voltage gated $K^+$ channels, more especially inhibitors $K_v1.5$ which has been linked to the ultra-rapidly activating delayed rectifier $K^+$ current $I_{Kur}$) and to pharmaceutical compositions containing such compounds. The present invention further provides for methods of using such compounds in the treatment of arrhythmia, $I_{Kur}$-associated disorders, and other disorders mediated by ion channel function.

BACKGROUND OF THE INVENTION

The importance of potassium channels was first recognized approximately fifty years ago when Hodgkin and Huxley discovered that potassium ions contributed to the current that excited the squid giant axon. Research in the area, however, was hampered by the lack of selective, high affinity ligands for potassium channels. But the advent of recombinant DNA techniques and single cell and whole cell voltage clamp techniques has changed the slow pace of the field. Indeed, potassium channels that exhibit functional, pharmacological and tissue distribution characteristics have been cloned. These cloned potassium channels are useful targets in assays for identifying candidate compounds for the treatment of various disease states. Potassium channels have turned out to be the most diverse family of ion channels discovered to date. They modulate a number of cellular events such as muscle contraction, neuro-endocrine secretion, frequency and duration of action potentials, electrolyte homeostatis, and resting membrane potential.

Potassium channels are expressed in eukaryotic and procaryotic cells and are elements in the control of electrical and non-electrical cellular functions. Potassium channels have been classified according to their biophysical and pharmacological characteristics. Subclasses of these channels have been named based on amino acid sequence and functional properties. Salient among these are the voltage dependent potassium channels, for example voltage gated potassium channels (e.g., $K_v1$, $K_v2$, $K_v3$, $K_v4$). Subtypes within these subclasses have been characterized as to their putative function, pharmacology and distribution in cells and tissues (Chandy and Gutman, "Voltage-gated potassium channel genes" in Handbook of Receptors and Channels—Ligand and Voltage-gated Ion Channels, ed. R. A. North, 1995; Doupnik et al., Curr. Opin. Neurobiol. 5:268, 1995). For example, the $K_v1$ class of potassium channels is further subdivided depending on the molecular sequence of the channel, for example $K_v1.1$, $K_v1.2$, $K_v1.3$, $K_v1.4$, $K_v1.5$, $K_v1.6$, and $K_v1.7$. Functional voltage-gated $K^+$ channels can exist as multimeric structures formed by the association of either identical or dissimilar subunits. This phenomena is thought to account for the wide diversity of $K^+$ channels. However, subunit compositions of native $K^+$ channels and the physiologic role that particular channels play are, in most cases, still unclear.

Membrane depolarization by $K_v1.3$ inhibition has been shown to be an effective method to prevent T-cell proliferation and therefore has applications in many autoimmune conditions. Inhibition of $K^+$ channels in the plasma membrane of human T-lymphocytes has been postulated to play a role in eliciting immunosuppressive responses by regulating intracellular $Ca^{++}$ homeostasis, which has been found to be important in T-cell activation.

The $K_v1.3$ voltage-gated potassium channel is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., J. Exp. Med. 160, 369, 1984; Decoursey et al., Nature, 307, 465, 1984). However, the $K^+$ channel blockers employed in their studies were non-selective. Until research with the peptide margatoxin, a peptide found in scorpion venom, no specific inhibitor of the $K_v1.3$ channel existed to test this hypothesis. Although a laboratory (Price et al., Proc. Natl. Acad. Sci. USA, 86, 10171, 1989) showed that charybdotoxin would block $K_v1.3$ in human T-cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., Proc. Natl, Acad. Sci, USA, 89, 10094, 1992). Margatoxin, on the other hand, blocks only $K_v1.3$ in T-cells, and has immunosuppressant activity on both in in vitro and in vivo models. (Lin et al., J. exp. Med, 177, 637, 1993). The therapeutic utility of this compound, however, is limited by its potent toxicity. Recently, a class of compounds has been reported that may be an attractive alternative to the above mentioned drugs, see for example U.S. Pat. Nos. 5,670,504; 5,631,282; 5,696,156; 5,679,705; and 5,696,156. While addressing some of the activity/toxicity problems of previous drugs, these compounds tend to be of large molecular weight and are generally produced by synthetic manipulation of a natural product, isolation of which is cumbersome and labor intensive.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort. Therefore, a selective immunosuppressant without these side effects still remains to be developed. Potassium channel inhibitors promise to be the solution to this problem.

Atrial fibrillation (AF) and atrial flutter are the most common cardiac arrhythmias in clinical practice and are likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse effects including ventricular proarrhythmia. Because current therapy is inadequate and fraught with side effects, there is a clear need to develop new therapeutic approaches Antiarrhythmic agents of Class III are drugs that cause a selective prolongation of the duration of the action potential without significant cardiac depression. Available drugs in this class are limited in number. Examples such as sotalol and amiodarone have been shown to possess interesting Class III properties (Singh B. N., Vaughan Williams E. M. "A Third Class of Anti-Arrhythmic Action: Effects On Atrial And Ventricular Intracellular Potentials And Other Pharmacological Actions On Cardiac Muscle, of MJ 1999 and AH 3747" Br. J. Pharmacol. 1970; 39:675-689. and Singh B. N., Vaughan Williams E. M, "The Effect of Amiodarone, A New Anti-Anginal Drug, On Cardiac Muscle", Br. J. Pharmacol. 1970; 39:657-667), but these are not selective Class III agents. Sotalol also possesses Class II effects which may cause cardiac depression and is contraindicated in certain susceptible patients. Amiodarone, also is not a selective Class III antiarrhythmic agent because it possesses multiple electrophysiological actions and is severely limited by side effects (Nademanee, K. "The Amiodarone Odyssey". J. Am. Coll. Cardiol. 1992; 20:1063-1065.) Drugs of this class are expected to be effective in preventing ventricular fibrillation. Selective class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. $Na^+$ or $Ca^{2+}$ currents; hereinafter $I_{Na}$ and $I_{Ca}$, respectively) or by reducing outward repolarizing potassium ($K^+$) currents. The delayed rectifier ($I_K$) $K^+$ current is the main outward current involved in the overall repolarization process during the action potential plateau, whereas the transient outward ($I_{to}$) and inward rectifier ($I_{K1}$) $K^+$ currents are responsible for the rapid initial and terminal phases of repolarization, respectively. Cellular electrophysiologic studies have demonstrated that $I_K$ consists of two pharmacologically and kinetically distinct $K^+$ current subtypes, $I_{Kr}$ (rapidly activating and deactivating) and $I_{Ks}$ (slowly activating and deactivating) (Sanguinetti and Jurkiewicz, Two Components Of Cardiac Delayed Rectifier $K^+$ Current: Differential Sensitivity To Block By Class III Antiarrhythmic Agents, J. Gen. Physiol. 1990, 96:195-215). Class III antiarrhythmic agents currently in development, including d-sotalol, dofetilide (UK-68,798), almokalant (H234/09), E-4031 and methanesulfonamide-N-[1'-6-cyano-1,2,3,4-tetrahydro-2-naphthalenyl)-3,4-dihydro-4-hydroxyspiro[2H-1-benzopyran-2,4'-piperidin]-6-yl]monochloride, predominantly, if not exclusively, block $I_{Kr}$. Although, amiodarone is a blocker of $I_{Ks}$ (Balser J. R. Bennett, P. B., Hondeghem, L. M. and Roden, D. M. "Suppression Of Time-Dependent Outward Current In Guinea Pig Ventricular Myocytes: Actions Of Quinidine And Amiodarone. Circ. Res. 1991, 69:519-529), it also blocks $I_{Na}$ and $I_{Ca}$, effects thyroid function, is as a nonspecific adrenergic blocker, and acts as an inhibitor of the enzyme phospholipase (Nademanee, K. "The Amiodarone Odyssey" J. Am. Coll. Cardiol. 1992; 20:1063-1065). Therefore its method of treating arrhythmia is uncertain. Most Class III agents that are known to be in development predominantly block $I_{Kr}$.

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD), prevents and/or terminates reentrant arrhythmias. Most selective Class III antiarrhythmic agents currently in development, such as d-sotalol and dofetilide predominantly, if not exclusively, block $I_{kr}$, the rapidly activating component of $I_K$ found both in the human atrium and ventricle.

Since these $I_{kr}$ blockers increase APD and refractoriness both in atria and ventricle without affecting conduction per se, theoretically they represent potential useful agents for the treatment of arrhythmias like AF. These agents have a liability in that they have an enhanced risk of proarrhythmia at slow heart rates. For example, torsades de points has been observed when these compounds are utilized (Roden, D. M. "Current Status of Class III Antiarrhythmic Drug Therapy", Am J. Cardiol, 1993; 72:44B-49B). This exaggerated effect at slow heart rates has been termed "reverse frequency-dependence", and is in contrast to frequency-independent or frequency-dependent actions (Hondeghem, L. M. "Development of Class III Antiarrhythmic Agents", J. Cadiovasc. Cardiol. 20 (Suppl. 2):S17-S22).

The slowly activating component of the delayed rectifier ($I_{ks}$) potentially overcomes some of the limitations of $I_{kr}$ blockers associated with ventricular arrhythmias. Because of its slow activation kinetics however, the role of $I_{ks}$ in atrial repolarization may be limited due to the relatively short APD of the atrium. Consequently, although $I_{ks}$ blockers may provide distinct advantage in the case of ventricular arrhythmias, their ability to affect SVT is considered to be minimal.

The ultra-rapidly activating delayed rectifier $K^+$ current ($I_{kur}$) is believed to represent the native counterpart to a cloned potassium channel designated $K_v1.5$ and, while present in human atrium, it appears to be absent in human ventricle. Furthermore, because of its rapidity of activation and limited slow inactivation, $I_{kur}$ is believed to contribute significantly to repolarization in human atrium. Consequently, a specific blocker of $I_{kur}$, that is a compound which blocks $K_v1.5$, would overcome the short coming of other compounds by prolonging refractoriness by retarding repolarization in the human atrium without causing the delays in ventricular repolarization that underlie arrhythmogenic after depolarizations and acquired long QT syndrome observed during treatment with current Class III drugs.

In intact human atrial myocytes an ultra-rapidly activating delayed rectifier K+ current $I_{kur}$ which is also known as the sustained outward current, $I_{sus}$, or $I_{so}$, has been identified and this current has properties and kinetics identical to those expressed by the human K+ channel clone (hK$_v$1.5, HK2) when isolated from human heart and stably expressed in human (HEK-293) cell lines. (Wang et al., 1993, Circ. Res. 73:1061-1076; Fedida et al., 1993, Circ. Res. 73:210-216; Snyders et al., 1993, J. Gen. Physiol. 101:513-543) and originally cloned from rat brain (Swanson et al., 10, Neuron 4:929-939). Although various antiarrhythmic agents are now available on the market, those having both satisfactory efficacy and a high margin of safety have not been obtained. For example, antiarrhythmic agents of Class I according to the classification scheme of Vaughan-Williams ("Classification Of Antiarrhythmic Drugs: In: Cardiac Arrhythmias, edited by: E. Sandoe, E. Flensted-Jensen, K. Olesen; Sweden, Astra, Sodertalje, pp 449-472, 1981) which cause a selective inhibition of the maximum velocity of the upstroke of the action potential ($_{max}$) are inadequate for preventing ventricular fibrillation. In addition, they have problems regarding safety, namely, they cause a depression of myocardial contractility and have a tendency to induce arrhythmias due to an inhibition of impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

SUMMARY OF THE INVENTION

The present invention provides heterocyclic dihydropyrimidine compounds of the following formula I, including enantiomers, diastereomers, and pharmaceutically acceptable salts thereof, useful as inhibitors of potassium channel function (especially inhibitors of the K$_v$1 subfamily of voltage gated K+ channels, more especially inhibitors K$_v$1.5 which has been linked to the ultra-rapidly activating delayed rectifier K+ current $I_{Kur}$) for the treatment of disorders such as arrhythmia and $I_{Kur}$-associated disorders, which have the structure

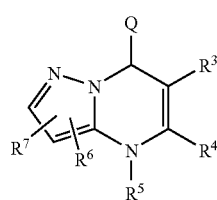

(I)

stereoisomers including enantiomers thereof and diastereomers thereof, or a pharmaceutically acceptable salt thereof, wherein Q is alkyl, substituted alkyl, cycloalkyl, substituted cycloalkyl, cycloheteroalkyl, substituted cycloheteroalkyl, or

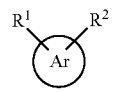

which is aryl, substituted aryl, heteroaryl or substituted heteroaryl;

$R^1$ and $R^2$ are the same or different and are independently selected from H, alkyl, substituted alkyl, halogen, carbocyclo, substituted carbocyclo, aryl, substituted aryl, heterocyclo, substituted heterocyclo, alkenyl, substituted alkenyl, alkynyl, substituted alkynyl, $CO_2R^a$, $CONR^bR^c$, $NR^dR^e$, $SO_2NR^fR^g$ or $SO_2R^hR^i$ where $R^a$, $R^b$, $R^c$, $R^d$, $R^e$, $R^f$, $R^g$, $R^h$ and $R^i$ are the same or different and are independently selected from H, alkyl or aryl;

$R^3$ is

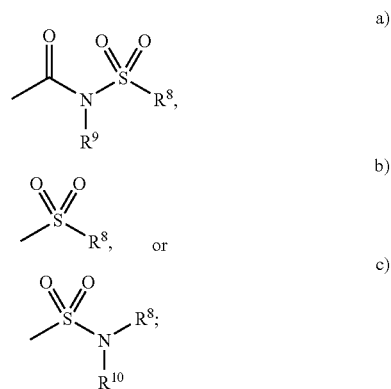

wherein $R^8$ is aryl, substituted aryl, carbocyclo, substituted carbocyclo, alkenyl, substituted alkenyl, alkynyl, substituted alkynyl, alkyl, substituted alkyl, heterocyclo, or substituted heterocyclo, $R^9$ is H, alkyl, substituted alkyl, cycloalkyl or substituted cycloalkyl;

$R^{10}$ is H, alkyl, substituted alkyl, cycloalkyl or substituted cycloalkyl; and wherein $R^8$ and $R^9$ or $R^8$ and $R^{10}$ together with the atoms to which they are bonded may optionally form a heterocyclic group or a substituted heterocyclic group;

$R^4$ is alkyl or substituted alkyl;

$R^5$ is H, alkyl or substituted alkyl;

$R^6$ and $R^7$ are the same or different and are independently selected from H, alkyl, substituted alkyl or polyhaloalkyl.

The present invention provides novel methods for the prevention and treatment of arrhythmia and $I_{Kur}$-associated disorders employing one or more compounds of the formula I, enantiomers, diastereomers or pharmaceutically acceptable salts thereof. In particular the present invention provides a novel method for the selective prevention and treatment of supraventricular arrhythmias.

Preferred Compounds

Compounds of the formula I and salts thereof wherein one or more, and especially all, of

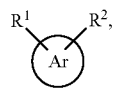

$R^1$, $R^2$, $R^3$, $R^4$, $R^5$, $R^6$, $R^7$, $R^8$ and $R^9$ are selected from the following definitions, are preferred compounds of the present invention.

Preferred are compounds of formula I wherein Q is

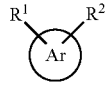

which is aryl (optionally substituted), or heteroaryl (optionally substituted), more preferably substituted aryl which is substituted phenyl, R¹ is halogen or alkyl,
R² is halogen or hydrogen,
R³ is

where R⁸ is phenyl, halophenyl, alkoxyphenyl, dialkoxyphenyl, cycloalkyl such as cyclohexyl, heteroaryl such as

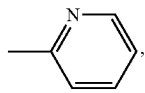

alkyl, alkylphenyl, cycloheteroalkyl such as

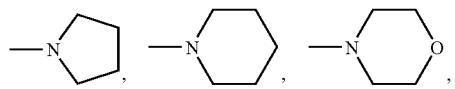

alkylamino, dialkylamino, or

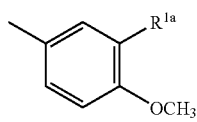

where R¹ᵃ is alkyl, heteroaryl or cycloheteroalkyl (each of which may be optionally substituted), or R³ is

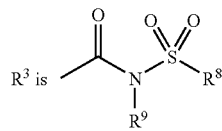

where R⁸ is alkyl, alkoxyphenyl, phenyl, halophenyl, heteroaryl, dialkylheteroaryl such as

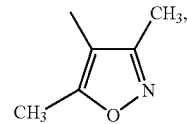

cycloheteroalkyl such as

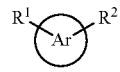

or cycloalkyl, and R⁹ is alkyl or cycloalkyl such as cyclopropyl,

R⁴ is hydroxyalkyl, alkyl or substituted alkyl, preferably substituted alkoxyalkyl such as benzyloxymethyl, R⁵ is hydrogen,
R⁶ is alkyl, hydrogen or trifluoromethyl, and
R⁷ is hydrogen.

More preferred are compounds of formula I wherein Q is

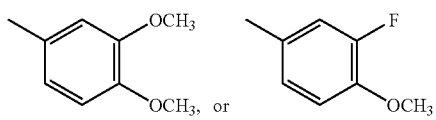

which is aryl, more preferably phenyl;

R¹ and R² are independently halogen, methyl, more preferably chlorine, fluorine or methyl;

R³ is —SO₂R⁸ where R⁸ is aryl, more preferably halophenyl, alkoxyphenyl,

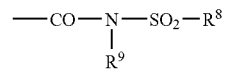

or R³ is $$-\text{CO}-\underset{\underset{R^9}{|}}{\text{N}}-\text{SO}_2-R^8$$

where R⁸ is aryl or substituted aryl, more preferably substituted phenyl; and R⁹ is alkyl or cycloalkyl, more preferably methyl, ethyl, i-propyl or cyclopropyl;

R⁴ is alkyl, more preferably methyl, ethyl or i-propyl or cyclopropyl,

R⁵ is hydrogen;
R⁶ is hydrogen, polyhaloalkyl, preferably CF₃, or methyl;
R⁷ is hydrogen.

Examples of preferred compounds in accordance with the present invention include the following:

-continued

| Example | Structure |
|---|---|
| 1 | 3,4-dichlorophenyl / 2,5-dimethyl-pyrazolo[1,5-a]pyrimidine with 6-(4-fluorophenylsulfonyl) |
| 2 | 3,4-dichlorophenyl / 2,5-dimethyl-pyrazolo[1,5-a]pyrimidine with 6-(4-chlorophenylsulfonyl) |
| 3 | 3,4-dichlorophenyl / 2,5-dimethyl-pyrazolo[1,5-a]pyrimidine with 6-(phenylsulfonyl) |
| 7 | 4-chloro-3-fluorophenyl / 2,5-dimethyl-pyrazolo[1,5-a]pyrimidine with 6-(phenylsulfonyl) |
| 8 | 3,4-dichlorophenyl / 2,5-dimethyl-pyrazolo[1,5-a]pyrimidine with 6-(4-methoxyphenylsulfonyl) |
| 10 | 3,4-dichlorophenyl / 2,5-dimethyl-pyrazolo[1,5-a]pyrimidine with 6-(cyclohexylsulfonyl) |
| 11 | 3,4-dichlorophenyl / 2,5-dimethyl-pyrazolo[1,5-a]pyrimidine with 6-(2-pyridylsulfonyl) |
| 18 | 3,4-dichlorophenyl / 2,5-dimethyl-pyrazolo[1,5-a]pyrimidine with 6-(n-butylsulfonyl) |
| 19 | 4-chlorophenyl / 2,5-dimethyl-pyrazolo[1,5-a]pyrimidine with 6-(4-methoxyphenylsulfonyl) |
| 24 | 4-methyl-3-fluorophenyl / 2,5-dimethyl-pyrazolo[1,5-a]pyrimidine with 6-(4-methoxyphenylsulfonyl) |

-continued
| Example | Structure |
|---|---|
| 25 | 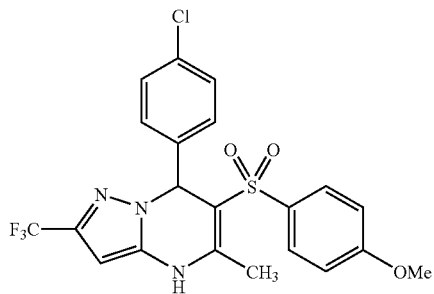 |
| 26 | 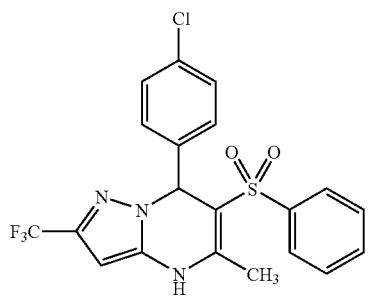 |
| 28 | 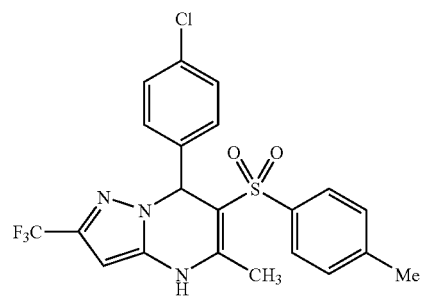 |
| 29 | 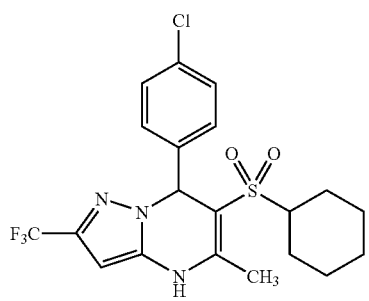 |
| 31 | 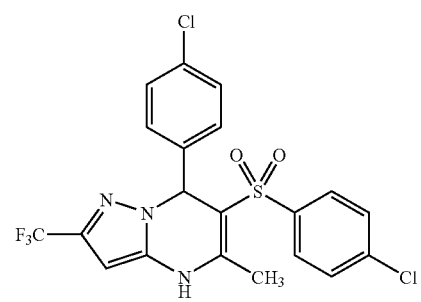 |
-continued
| Example | Structure |
|---|---|
| 32 | 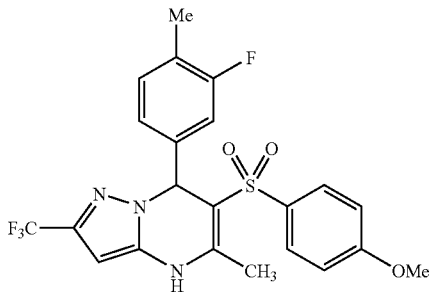 |
| 35 | 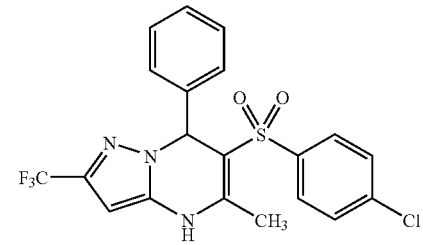 |
| 38 | 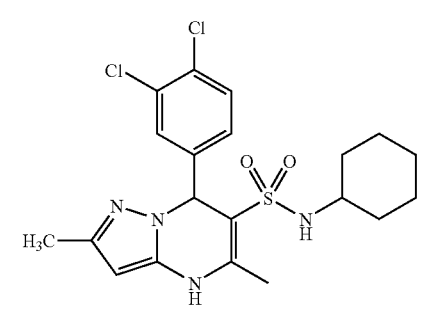 |
| 39 | 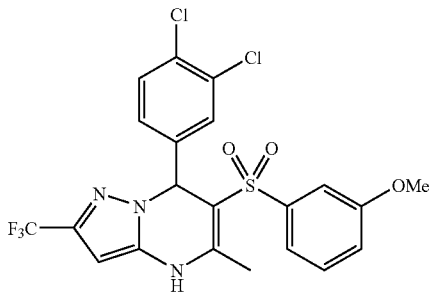 |
| 41 | 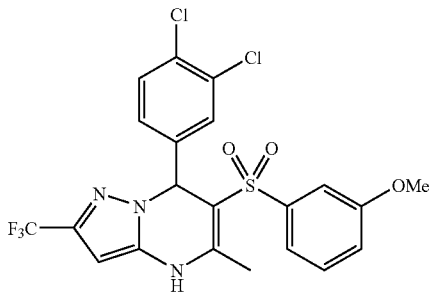 |

-continued
| Example | Structure |
|---|---|
| 42 | 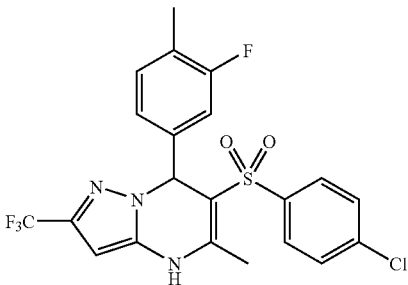 |
| 43 | 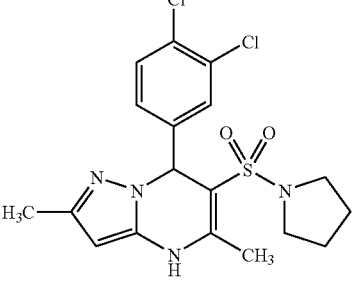 |
| 47 | 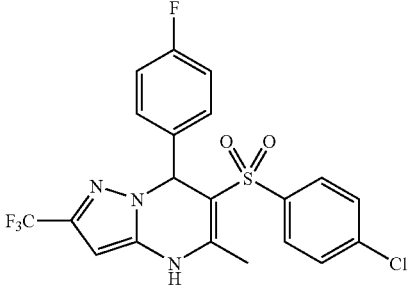 |
| 48 | 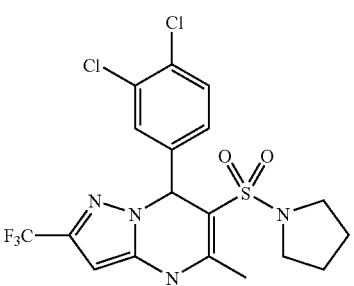 |
| 51 | 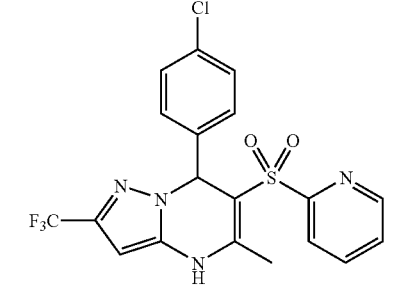 |
-continued
| Example | Structure |
|---|---|
| 53 | 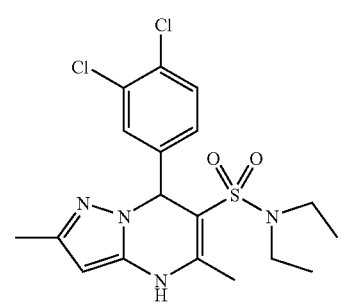 |
| 59 | 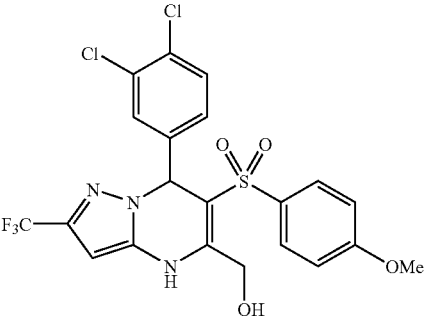 |
| 61 | 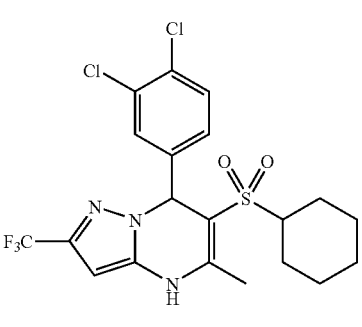 |
| 65 | 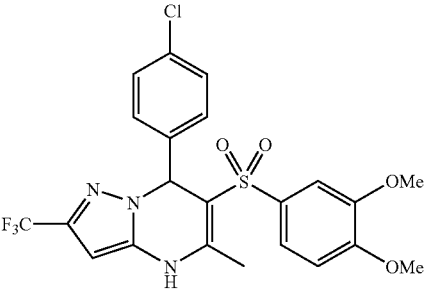 |
| 66 | 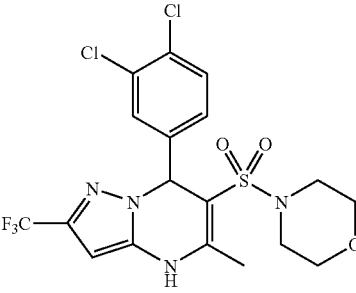 |

| Example | Structure |
|---------|-----------|
| 77 | 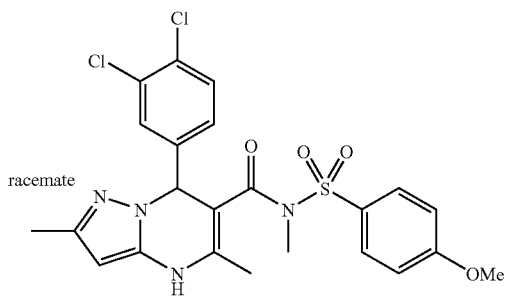 |
| 78 | 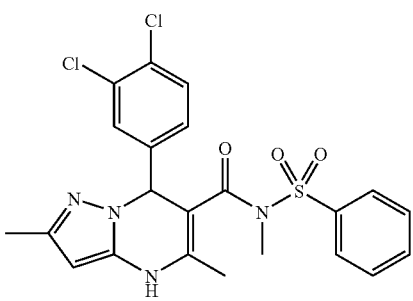 |
| 81 | 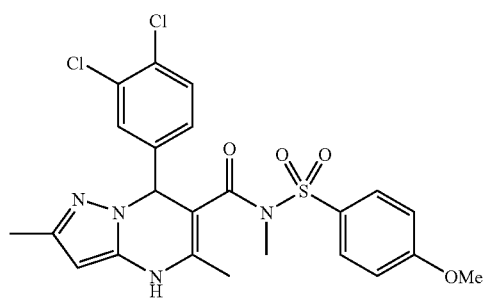 |
| 87 | 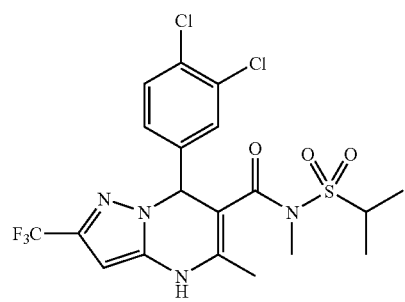 |
| 88 | 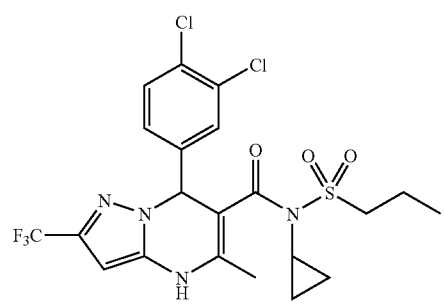 |"
| Example | Structure |
|---------|-----------|
| 93 | 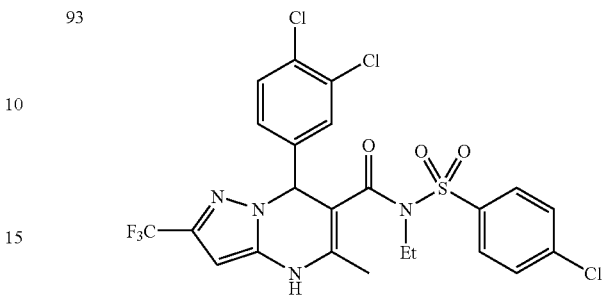 |
| 94 | 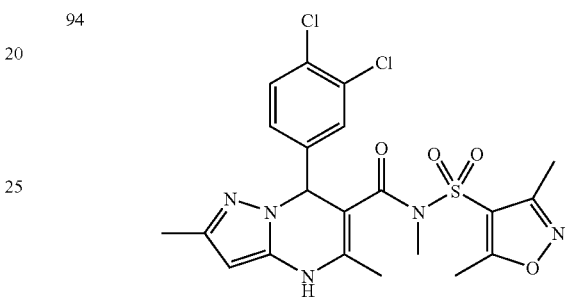 |
| 95 | 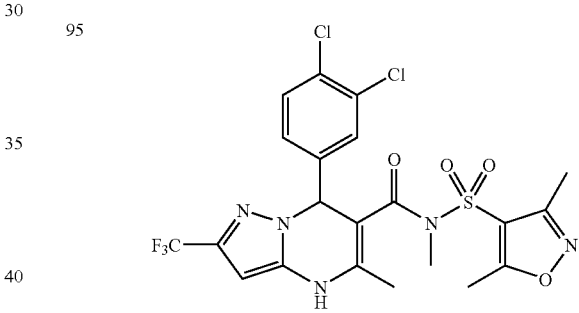 |
| 97 | 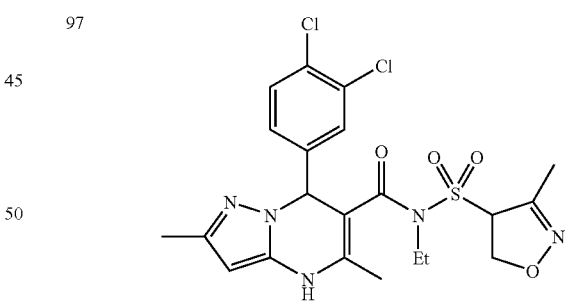 |
| 98 | 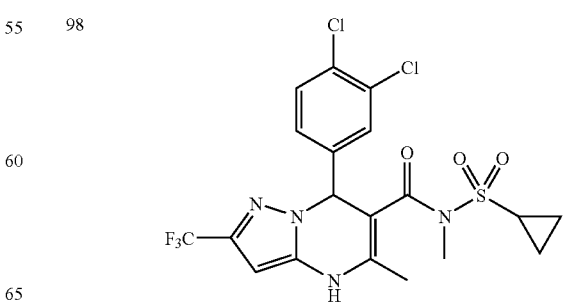 |

| Example | Structure |
|---|---|
| 99 | 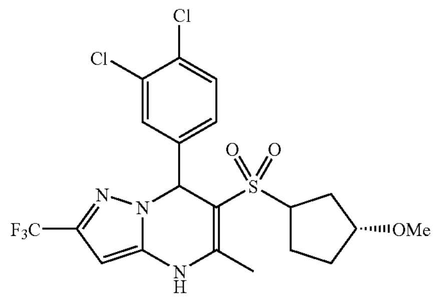 |

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "substituted" as used in conjunction with a particular radical or group (for example, substituted alkyl) refers to the fact that such group may be substituted as indicated in the definition for such group (for example, the definition for substituted alkyl). However, even where such group is not referred to as being substituted, it still may be optionally substituted as indicated in the definition for such group.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred. The term "substituted alkyl" refers to alkyl groups substituted with one or more groups selected from alkyl, substituted alkyl, aryl such as phenyl (optionally substituted), substituted aryl, heterocyclo, substituted heterocyclo, carbocyclo, substituted carbocyclo, halo, hydroxy, arylalkoxy (optionally substituted), alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. The term "substituted alkenyl" refers to alkenyl groups substituted with one or more groups (such as by groups described above in the definition of alkyl), preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The term "alkynyl" refers to straight or branched chain hydrocarbon groups having 2 to 12 carbon atoms, preferably 2 to 4 carbon atoms, and at least one triple carbon to carbon bond, such as ethynyl. The term "substituted alkynyl" refers to alkynyl groups substituted with one or more groups (such as by groups described above in the definition of alkyl), preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms

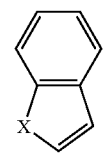

"ar" or "aryl" refer to aromatic homocyclic (i.e., hydrocarbon) mono-, bi- or tricyclic ring-containing groups preferably having 6 to 12 members such as phenyl, naphthyl and biphenyl and may optionally include one to three additional rings fused to a carbocyclic ring or a heterocyclic ring (such as aryl, cycloalkyl, heteroaryl or cycloheteroalkyl), for example

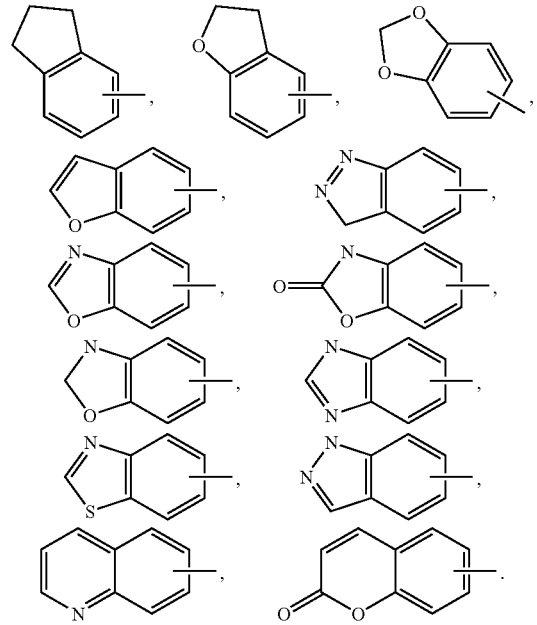

(where X is N, $R^j$—N (where $R^j$ is alkyl) or O),

Phenyl is a preferred aryl group. The term "substituted aryl" refers to aryl groups substituted with one or more groups (such as by groups described above in the definition of alkyl), preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, etc., where optionally one or more pair of substitutents together with the atoms to which they are bonded form a 3 to 7 member ring.

The terms "cycloalkyl" and "cycloalkenyl" refer to mono-, bi- or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g. fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups (such as by groups described above in the definition of alkyl), preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The terms "carbocyclo", "carbocyclic" or "carbocyclic group" refer to both cycloalkyl and cycloalkenyl groups. The terms "substituted carbocyclo", "substituted carbocyclic" or "substituted carbocyclic group" refer to carbocyclo or carbocyclic groups substituted with one or more groups as described in the definition of cycloalkyl and cycloalkenyl.

The terms "halogen" and "halo" refer to fluorine, chlorine, bromine and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring ("cycloheteroalkyl"). Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

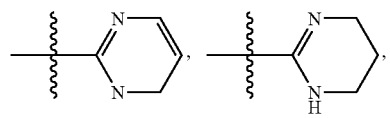

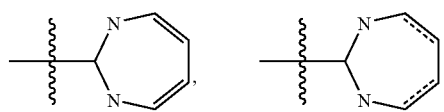

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4dioxa-8-azaspiro[4,5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

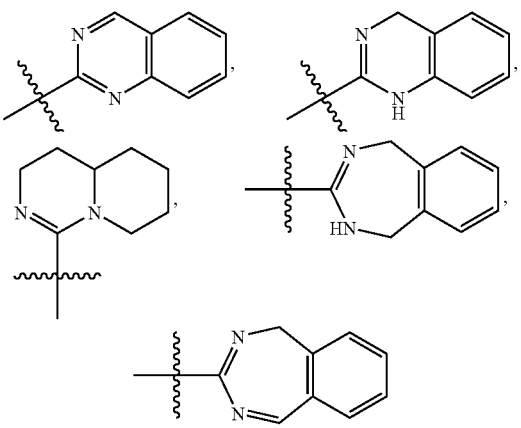

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups (such as by groups described above in the definition of alkyl), preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, etc., where optionally one or more pair of substitutents together with the atoms to which they are bonded form a 3 to 7 member ring.

The term "alkanoyl" refers to alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

Throughout the specification, groups and substitutents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form pharmaceutically acceptable salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form pharmaceutically acceptable salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

To the extent that compounds of the formula I, and salts thereof, may exist in their tautomeric form, all such tautomeric forms are contemplated herein as part of the present invention.

All stereoisomers of the present compounds, such as those which may exist due to asymmetric carbons on the various R and Z substitutents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The terms "including", "such as", "for example" and the like are intended to refer to exemplary embodiments and not to limit the scope of the present invention.

Schemes

Compounds of formula I may be prepared using the sequence of steps outlined below.

Compound I of the present invention can be prepared in a number of ways known to one skilled in the art of organic synthesis. Compound I of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts, *Protective Groups in Organic Synthesis*, Wiley and Sons, 1991. All references cited herein are hereby incorporated in their entirety herein by reference.

Compound I of this invention where $R^3$ is $SO_2R^8$ can be prepared as shown in Scheme 1, wherein an appropriate aminoheteroaryl 1, aldehyde 2 and β-ketosulfone 3 are converted to dihydropyrimidine of the invention IA under Bignelli conditions (*J. Org. Chem.*, 1991, 56:1713).

SCHEME 1

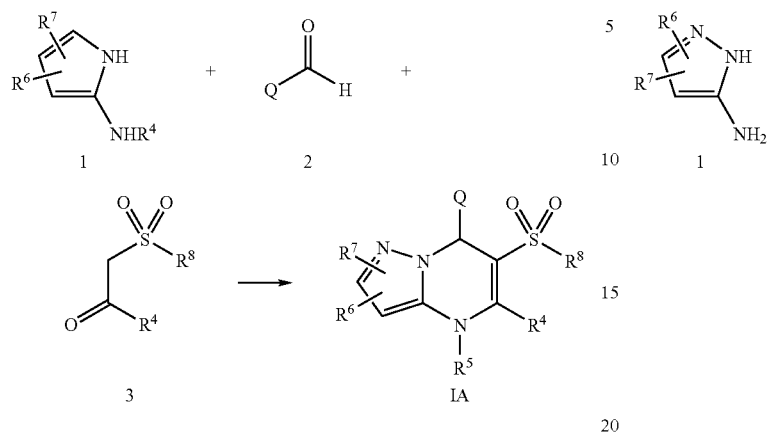

Compound I of the invention where $R^3$ is $SO_2$—$NR^8R^{10}$ can be prepared as outlined in Scheme 2, where an appropriate aminoheteroaryl 1, aldehyde 2 and β-ketosulfonamide 4 are converted to dihydropyrimidine of the invention IB under Bignelli conditions.

SCHEME 2

Compound I of the invention where $R^3$ is $$-\overset{O}{\underset{}{C}}-\underset{R^9}{N}-SO_2-R^8$$

and $R^5$ is H can be prepared as outlined in Scheme 3. Under Bignelli conditions, aminoheteroaryl 1, aldehyde 2 and β-ketoester 5 are converted to dihydropyrimidine 6 which is then converted to compound 7 after protection of NH with a protecting group (PG). Ester hydrolysis of 7 followed by coupling with sulfonamide $R^8SO_2NHR^9$ provides acylsulfonamide 8, which upon deprotection give desired compound of the invention IC. PG can be a protecting group such as BOC, methylmethoxymethyl (MOM) or methylethoxymethyl (MEM).

SCHEME 3

Compound I of the invention where $R^3$ is $$-\overset{O}{\underset{}{C}}-\underset{R^9}{N}-SO_2R^8$$

and $R^5$ is alkyl or substituted alkyl can be prepared as shown in Scheme 3a. Under Bignelli conditions, aminoheteroaryl 1, aldehyde 2 and β-ketoester 9 are converted to dihydropyrimidine 9a. Ester hydrolysis of 10 followed by coupling with sulfonamide 11 provides the compound of the invention ICa.

SCHEME 3a

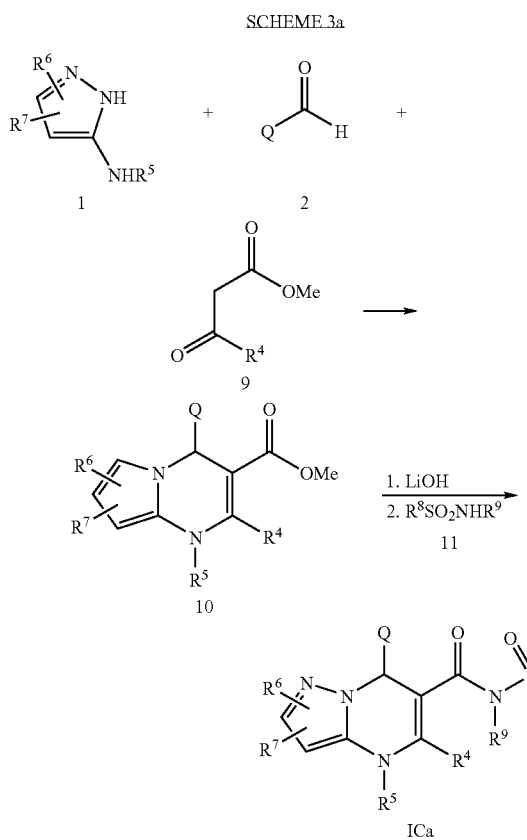

Alternatively, compounds of the invention can also be prepared as outlined in Scheme 4. Condensation of aldehyde 2 with β-ketosulfone 3 in the presence of a base such as piperidine provides 12, which reacts with aminoheteroaryl 1 under elevated temperature to give compounds of the invention IA.

SCHEME 4

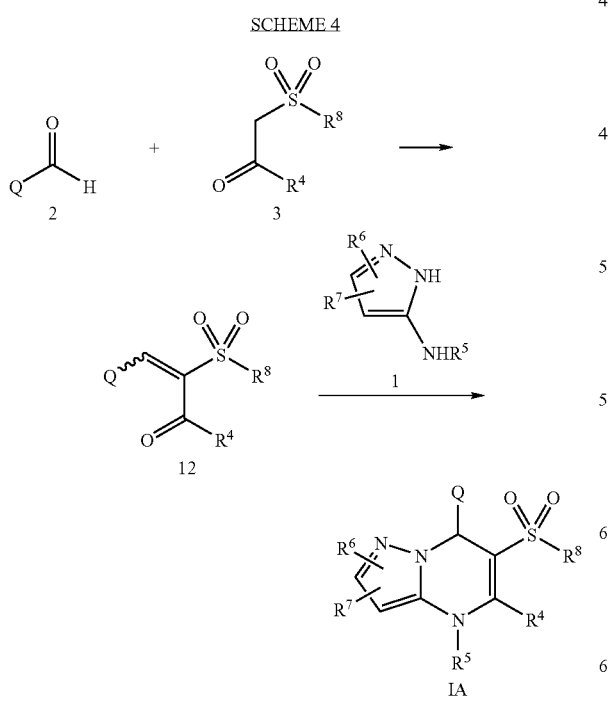

Alternatively, compounds of the invention can also be prepared as outlined in Scheme 5. Condensation of aldehyde 2 with β-ketosulfonamide 4 in the presence of a base such as piperidine provides 13, which reacts with aminoheteroaryl 1-under elevated temperature to give compounds of the invention IB.

SCHEME 5

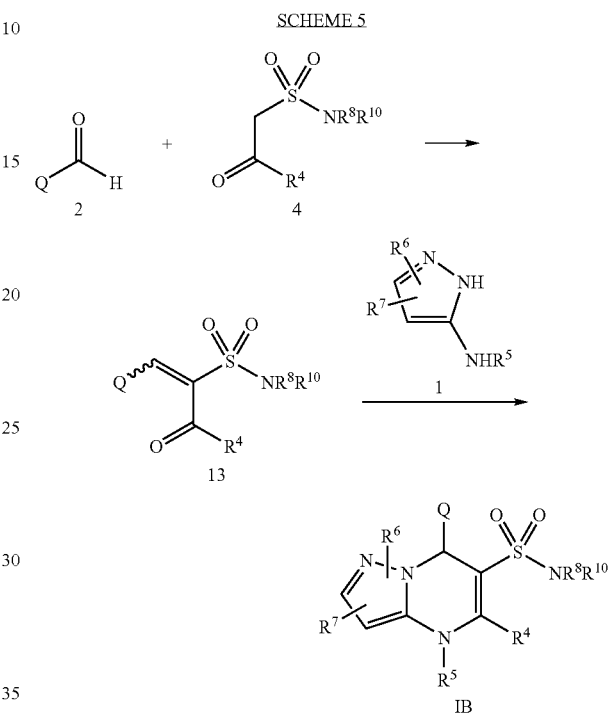

Alternatively, compounds of the invention can also be prepared as outlined in Scheme 6. Condensation of aldehyde 2 with β-ketoester 9 in the presence of a base such as piperidine provides 14, which reacts with aminoheteroaryl 1a under elevated temperature to give compounds of formula 6. Compounds of the invention IC can be obtained via procedures known to those skilled in the art such as Scheme 3.

SCHEME 6

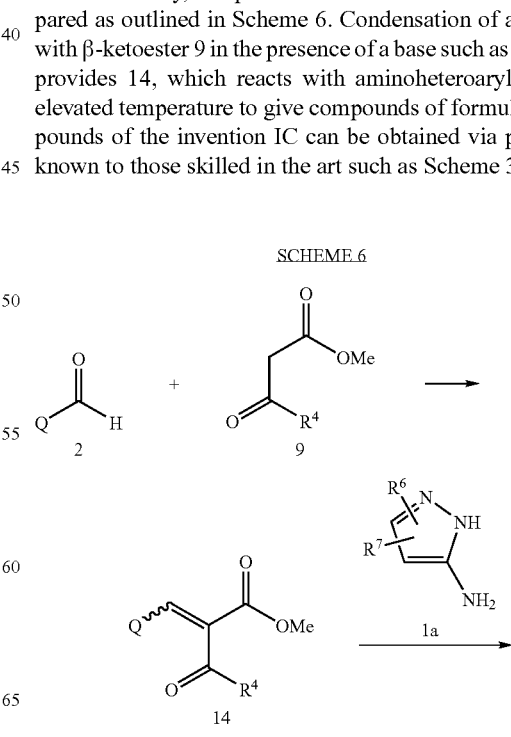

-continued

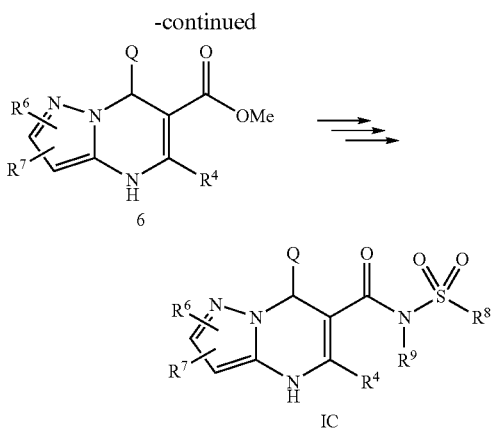

A fully elaborated β-ketosulfone 3 can be prepared as shown in Scheme 7. Thiol 15 and chloroacetone 16 are converted to sulfide 17 under basic conditions. Upon oxidation, sulfide 17 is converted to β-ketosulfone 3, which is then converted to compounds of the invention IA via procedures such as described with respect to Schemes 1 and 4.

SCHEME 7

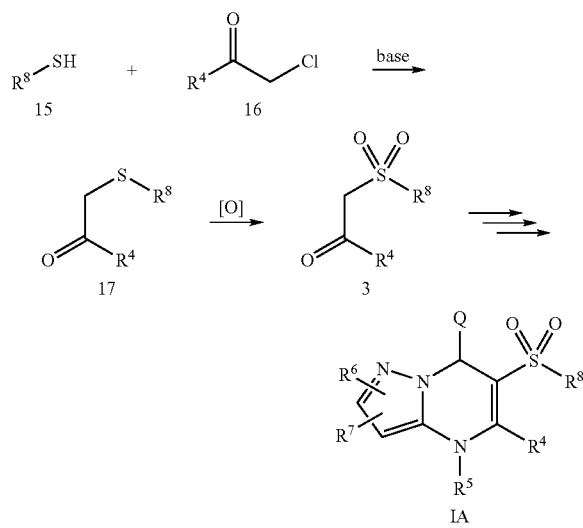

Alternatively, compounds of the invention can also be prepared as outlined in Scheme 8. Sulfone 18, upon acylation, is converted to β-ketosulfone 3, which is then converted to compounds of the invention IA via procedures such as described with respect to Schemes 1 and 4.

SCHEME 8

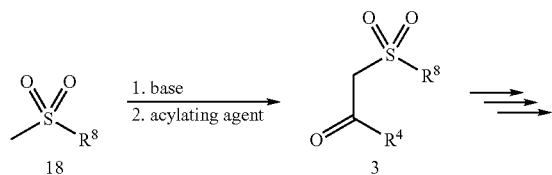

-continued

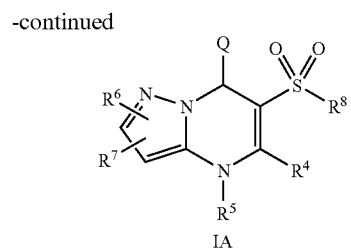

Alternatively, compounds of the invention can also be prepared as outlined in Scheme 9. Methanesulfonyl chloride 19 is treated with amine 20 in the presence of base to give sulfonamide 21, which is then converted to β-ketosulfonamide 4 by acylation employing an acylating agent such as Weinreb amide or aryl chloride. Compounds of the present invention IB are obtained from 4 via procedures such as described with respect to Scheme 2.

SCHEME 9

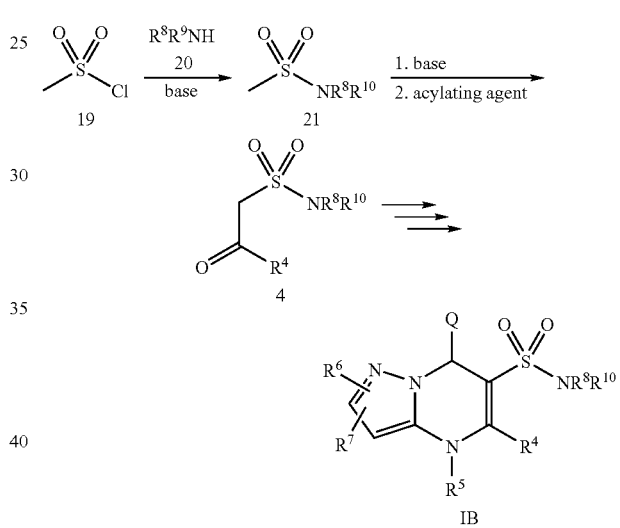

Alternatively, compounds of the invention can also be prepared as outlined in Scheme 10. Reaction of amine 22 with chlorosulfonic acid 23 provides sulfamic acid 24, which is then converted to sulfamoyl chloride 25 by treatment of base such as NaOH followed by $PCl_5$. Upon treatment with silylenoether 26, compound 25 is converted to β-ketosulfonamide 5, which is then converted to compounds of the invention IB via procedures such as described with respect to Scheme 2.

SCHEME 10

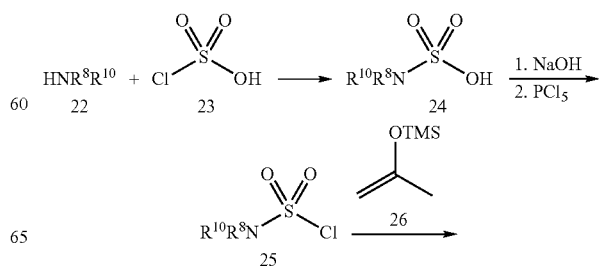

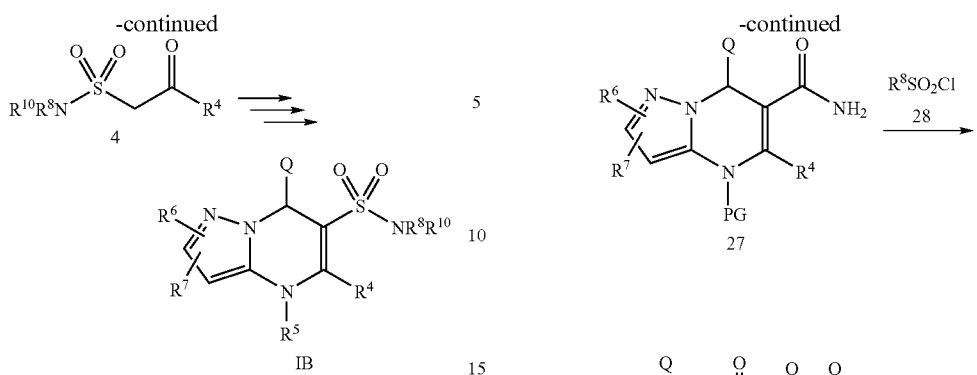
Alternatively, compounds of the invention can also be prepared as outlined in Scheme 1. Starting from intermediate 8a, ester hydrolysis followed by amide formation gives compound 27, which is reacted with sulfonyl chloride 28 to provide compound 29. Alkylation followed by deprotection gives compounds of the invention IC.
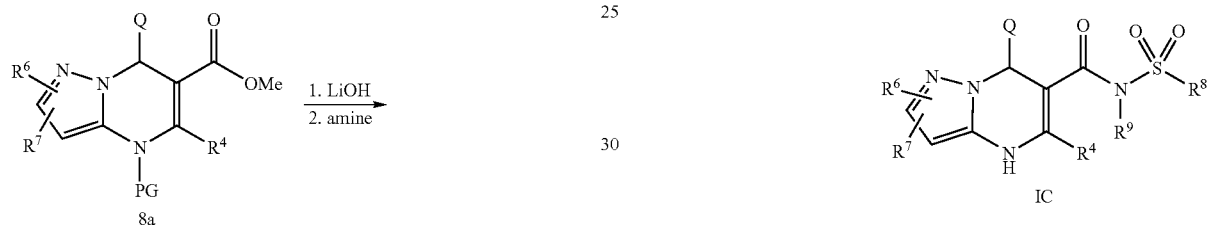
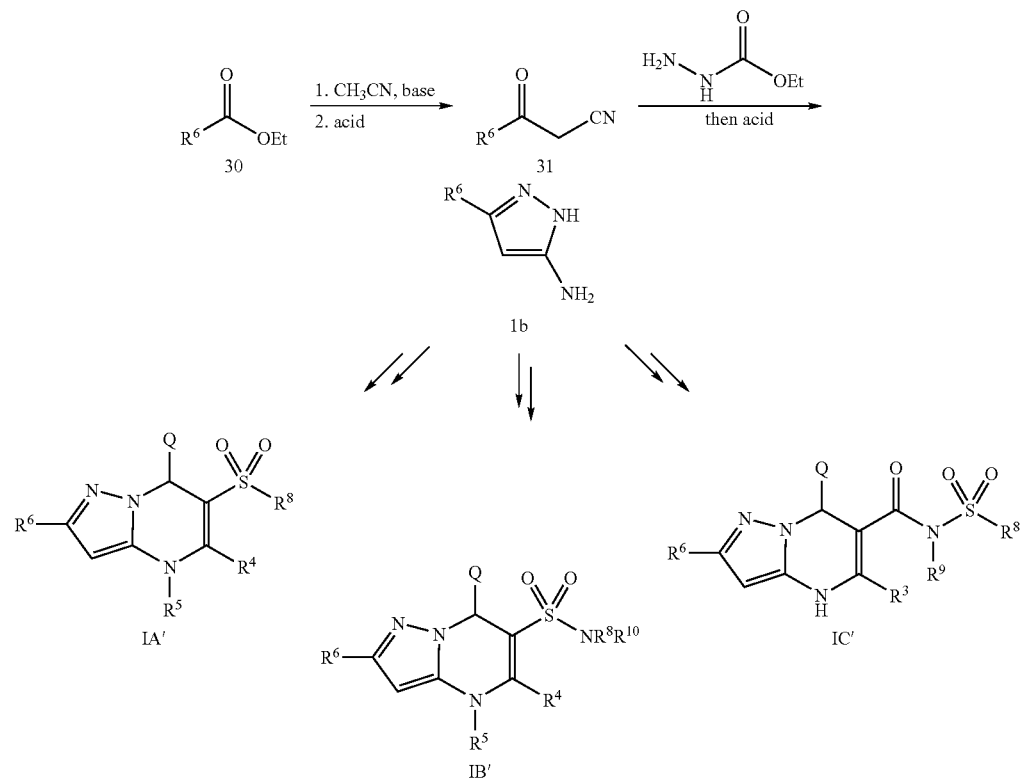

Alternatively, compounds of the invention can also be prepared as outlined in Scheme 12. Ester 30 is converted to compound 31 by treatment with acetonitrile in the presence of a base, followed by treatment with acid such as HCl. Aminopyrazole 1b is obtained according to Zohdi's procedure (*J. Chem. Research*, 1992, 82). Compounds of this invention IA', IB' and IC' can then be obtained via procedures such as described with respect to Schemes 1 to 6.

Alternatively, compounds of the invention can be prepared as outlined in Scheme 13. Nitration of pyrazole 32 gives compound 33, which under thermal migration and reduction provides aminopyrazole 30. Compounds of the invention IA, IB and IC can then be obtained via procedures known in the art or as described with respect to Schemes 1 to 6.

Utility

Compounds within the scope of the present invention inhibit the $K_v1$ subfamily of voltage-gated $K^+$ channels, and as such are useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents; angina pectoris including relief of Prinzmetal's symptoms, vasospastic symptoms and variant symptoms; gastrointestinal disorders including reflux esophagitis, functional dispepsia, motility disorders (including constipation and diarrhea), and irritable bowel syndrome; disorders of vascular and visceral smooth muscle including asthma,

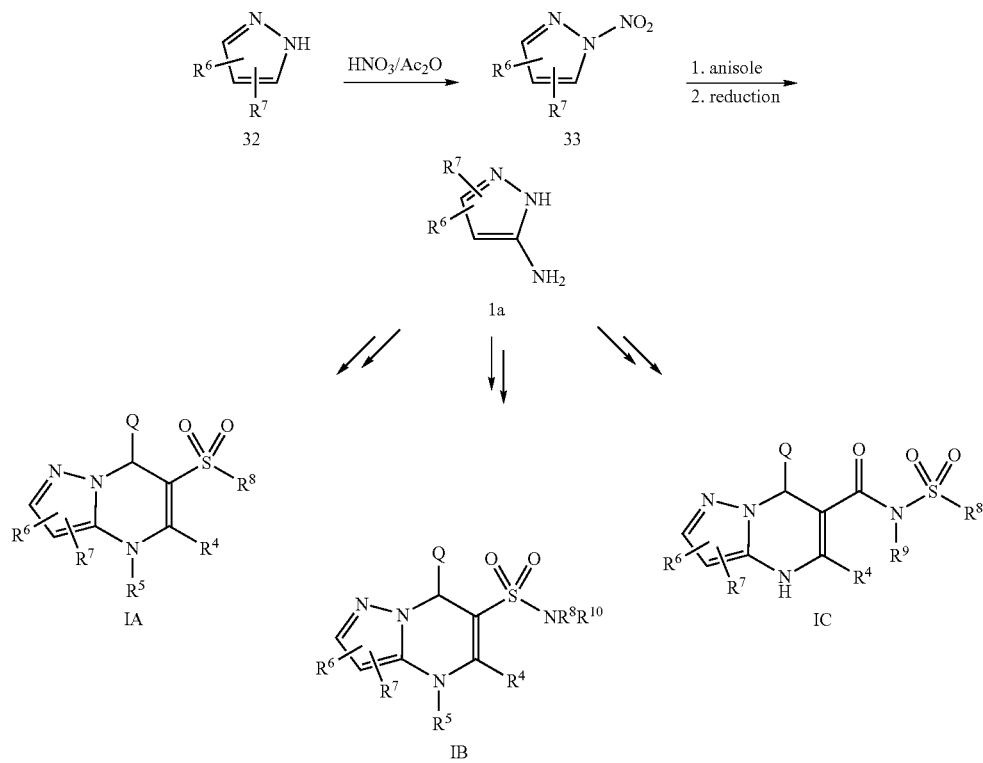

Additional compounds within the scope of the present invention can be prepared from the compounds obtained by the above described methods through conversion of the substitutent groups to other functionality by the usual methods of chemical synthesis, as illustrated in the following examples.

Compounds of formula I that contain chiral centers maybe obtained in non-racemic form by non-racemic synthesis or resolution by methods well known to those skilled in the art. Compounds that are non-racemic are designated as "chiral" in the examples.

In the examples described below it may be necessary to protect reactive functionality such as hydroxy, amino, thio or carboxy groups, where these are desired in the final product, to avoid their unwanted participation in reactions. The introduction and removal of protecting groups are well known to those skilled in the art, for example see Green, T. W. in "Protective Groups in Organic Synthesis", John Wiley and Sons, 1991.

chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma. chronic obstructive pulmonary disease, cystic fibrosis and atherosclerosis; cell proliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As inhibitors of the $K_v1$ subfamily of voltage-gated $K^+$ channels compounds of the present invention are useful to treat a variety of disorders including resistance by transplantation of organs or tissue, graft-versus-host diseases brought about by medulla ossium transplantation, rheumatoid arthritis, systemic lupus erythematosus, hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenicmicroorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-$C_4$ release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention are antiarrhythmic agents which are useful in the prevention and treatment (including partial alleviation or cure) of arrhythmias. As inhibitors of $K_v1.5$ compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio is preferably greater than 4:1, more preferably greater than 10:1, and most preferably such that prolongation of the atrial effective refractory response period is achieved without significantly detectable prolongation of the ventricular effective refractory period.

In addition, the compounds within the scope of the present invention block $I_{Kur}$, and thus may be useful in the prevention and treatment of all $I_{Kur}$-associated conditions. An "$I_{Kur}$-associated condition" is a disorder which may be prevented, partially alleviated or cured by the administration of an $I_{Kur}$ blocker. The $K_v1.5$ gene is known to be expressed in stomach tissue, intestinal/colon tissue, the pulmonary artery, and pancreatic beta cells. Thus, administration of an $I_{Kur}$ blocker could provide useful treatment for disorders such as: reflux esophagitis, functional dispepsia, constipation, asthma, and diabetes. Additionally, $K_v1.5$ is known to be expressed in the anterior pituitary. Thus, administration of an $I_{Kur}$ blocker could stimulate growth hormone secretion. $I_{Kur}$ inhibitors can additionally be useful in cell proliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the formula I. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of the formula I or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula I are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inhibitors (i.e., COX-1 and/or COX-2 inhibitors) such as aspirin, indomethacin, ibuprofen, piroxicam, Naproxen®, Celebrex®, Vioxx® and NSAIDs; anti-platelet agents such as GPIIb/IIIa blockers (e.g., abciximab, eptifibatide and tirofiban), $P2Y_{12}$ antagonists (e.g., clopidogrel, ticlopidine and prasugrel (CS-747), thromboxane receptor antagonists (e.g., ifetroban), aspirin, and PDE-III inhibitors (e.g., dipyridamole) with or without aspirin; as well as antiplatelet agents such as abciximab, eptifibatide and anagrelide; diruetics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetaide, triamtrenene, amiloride, and spironolactone; antihypertensive agents such as alpha adrenergic blockers, beta adrenergic blockers, calcium channel blockers, diuretics, renin inhibitors, ACE inhibitors, (e.g., captropril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g. sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such anti-hypertensive agents; anti-thrombotic/thrombolytic agents such as tissue plasminogen activator (tPA), recombinant tPA, tenecteplase (TNK), lanoteplase (nPA), factor VIIa inhibitors, factor Xa inhibitors, thrombin inhibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as LDL lowering agents such as torcetrapid (Pfizer), ezetimibe, a combination of atorvastatin and torcetrapid, a combination of simvastatin and ezetimibe, squalene synthetase inhibitors, fibrates, and bile acid sequestrants (e.g., questran); antiproliferative agents such as cyclosporin A, taxol, FK 506, and adriamycin; antitumor agents such as taxol, adriamycin, epothilones, cisplatin and carboplatin; anti-diabetic agents such as biguanides (e.g. metformin), glucosidase inhibitors (e.g. acarbose), insulins, meglitinides (e.g. repaglinide), sulfonylureas (e.g. glimepiride, glyburide and glipizide), biguanide/glyburide combinations (i.e., glucovance), thiazolidinediones (e.g. troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplernone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inhibitors including PDE III inhibitors (e.g. cilostazol), and PDE V inhibitors (e.g., sildenafil); protein tyrosine kinase inhibitors; steroidal anti-inflammatory agents such as prednisone, and dexamethasone; and other anti-inflammatory agents such as enbrel.

The above other therapeutic agents, when employed in combination with the compounds of the present invention, may be used, for example, in those amounts indicated in the Physicians' Desk Reference (PDR) or as otherwise determined by one of ordinary skill in the art.

The following examples and preparations represent preferred embodiments of the invention and describe the manner and process of making and using the invention. It is to be understood that there may be other embodiments which fall within the spirit and scope of the invention as defined by the claims appended hereto. Abbreviations employed herein are defined below.

CDI=carbonyl diimidazole
DCM=dichloromethane
DMAP=dimethylaminopyridine
DMF=dimethylformamide
DMPU=1,3-Dimethyl-3,4,5,6-tetrahydro-2(1H)-pyrimidinone
EDCl (or EDC)=1-(3-Dimethylaminopropyl)-3-ethylcarbodiimide hydrochloride
M+H=monoisotopic mass plus one proton
Et=ethyl
h=hours
HPLC=high performance liquid chromatography
HOBT=hydroxybenzotriazole
LC/MS=liquid chromatography/mass spectrometry
Me=methyl
min=minutes
MS=mass spectrometry
NaOAc=sodium acetate
Ph=phenyl
PPA=poly phosphoric acid
Pr=propyl
Py=pyridine
PyBrOP=bromo-tris-pyrrolidino-phosphonium hexafluorophosphate
RT=room temperature
Rt=retention time
TEA=triethylamine
TFA=trifluoroacetic acid
TLC=thin layer chromatography
THF=tetrahydrofuran
TMSOTf=trimethylsilyl trifluoromethanesulfonate Assays to determine the degree of activity of a compound as an $I_{Kur}$ inhibitor are well known in the art and are described in references such as *J. Gen. Physiol.* Apr.; 101 (4):513-43, and *Br. J. Pharmacol.* 1995 May; 115(2):267-74.

Assays to determine the degree of activity of a compound as an inhibitor of other members of the $K_v1$ subfamily are also well known in the art. For example, inhibition of Kv1.1, $K_v1.2$ and $K_v$ 1.3 can be measured using procedures described by Grissmer S, et al., *Mol Pharmacol* 1994 June; 45(6):1227-34. Inhibition of Kv1.4 can be measured using procedures described by Petersen K R, and Nerbonne J M, *Pflugers Arch* 1999 Feb.; 437(3):381-92. Inhibition of Kv1.6 can be measured using procedures described by Bowlby M R, and Levitan I B, *J Neurophysiol* 1995 Jun.; 73(6):2221-9. And inhibition of Kv1.7 can be measured using procedures described by Kalman K, et al., *J Biol Chem* 1998 Mar. 6; 273(10):5851-7.

Compounds within the scope of the present invention demonstrate activity in $K_v1$ assays such as the ones described above.

All documents cited in the present specification are incorporated herein by reference in their entirety.

EXAMPLES

Where an example refers to Isomer 1 and Isomer 2, it refers to the two enantiomers separated from a racemic mixture without designating which is R or S. The various enantiomers or isomers were separated on Chiral PAK AS using 15-20% EtOH-MeOH in heptane.

Example 1

7-(3,4-Dichlorophenyl)-6-(4-fluorophenylsulfonyl)-2,5-dimethyl-4,7-dihydropyrazolo[1,5-a]pyrimidine Isomer 1: $K_v1.5$% inhibition: 98% at 0.3 μM Isomer 2: $K_v1.5$% inhibition: 48% at 0.3 μM

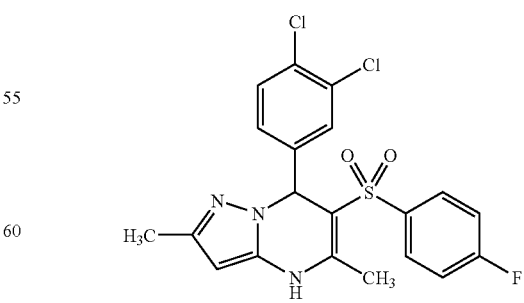

7-(3,4-Dichlorophenyl)-6-(4-fluorophenylsulfonyl)-2,5-dimethyl-4,7-dihydropyrazolo[1,5-a]pyrimidine was synthesized following the synthetic scheme outlined below.

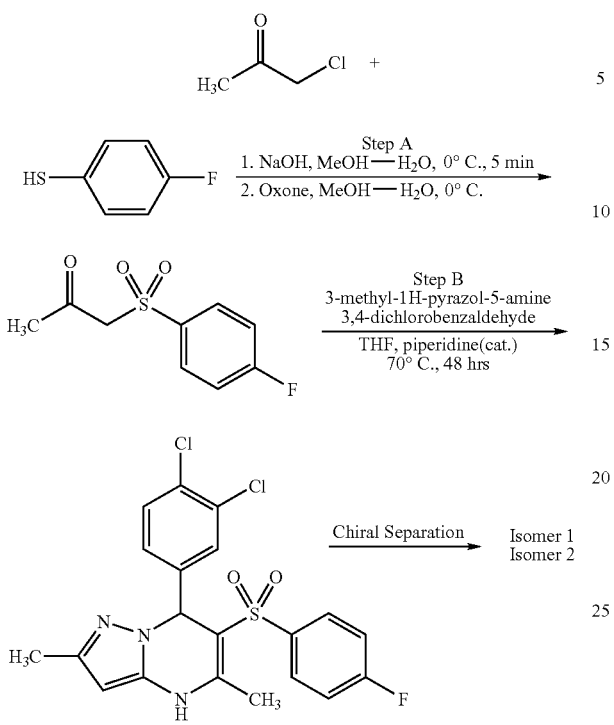

Step A:

NaOH (1.0M, 40.5 mL, 40.5 mmol) was added at 0° C. to a solution of 4-fluorothiophenol (5.20 g, 40.5 mmol) in methanol (100 mL) followed by addition of chloroacetone (3.87 mL, 48.6 mmol). The reaction was stirred at 0° C. for 5 minutes. Oxone (50 g, 81 mmol) was added all at once. The suspension was stirred at 0° C. and monitored by LC-MS until there was no sulfoxide (reaction intermediate) observed. The reaction was filtered and solid washed with diethyl ether. Most organic solvents were removed from the filtrate. The solution was extracted with diethyl ether three times. Combined organic phases were extracted with 5% NaOH aq. solution three times. Combined aqueous phases were acidified with 1.0N hydrochloric acid to precipitate product. Pure Step A product, 1-(4-fluorophenylsulfonyl)propan-2-one, was obtained after flash chromatography (silica gel, 3:7 ethyl acetate:hexanes) as a white solid. LC-MS found: $(M+1)^+=217.2$.

Step B:

1-(4-Fluorophenylsulfonyl)propan-2-one (150 mg, 0.69 mmol), 3-methyl-1H-pyrazol-5-amine (67 mg, 0.69 mmol) and 3,4-dichlorobenzaldehyde (121 mg, 0.69 mmol) were dissolved in THF (5 mL), to which was added a catalytic amount of piperidine (3 drops). The reaction in a sealed tube was stirred at 70° C. for about 48 hrs. After cooling to rt., solvent was removed and crude product was purified by HPLC (acetonitrile-water, 5% to 95% gradient) to provide pure Step B product 7-(3,4-dichlorophenyl)-6-(4-fluorophenylsulfonyl)-2,5-dimethyl-4,7-dihydropyrazolo[1,5-a]pyrimidine as a solid. LC-MS found: $(M+1)^+=452.17$. The two enantiomers were readily separated on Chiral PAK AS using 15% EtOH-MeOH in heptane.

Example 2

6-(4-Chlorophenylsulfonyl)-7-(3,4-dichlorophenyl)-5-methyl-4,7-dihydropyrazolo[1,5-a]pyrimidine Isomer 1: $K_v1.5$ $IC_{50}$ 92 nM Isomer 2: $K_v1.5$ $IC_{50}$ 37 nM

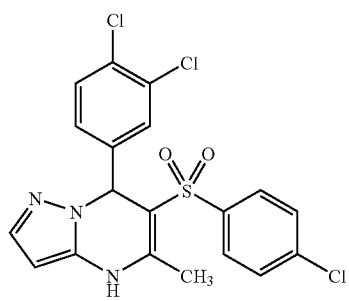

Following a procedure similar to that described in Example 1, 6-(4-chlorophenylsulfonyl)-7-(3,4-dichlorophenyl)-5-methyl-4,7-dihydropyrazolo[1,5-a]pyrimidine was obtained as a white solid. LC-MS found: $(M+1)^+=454.2$.

Example 3

7-(3,4-Dichlorophenyl)-2,5-dimethyl-6-(phenylsulfonyl)-4,7-dihydropyrazolo[1,5-a]pyrimidine Isomer 1: $K_v1.5$ $IC_{50}$ 41 nM Isomer 2: $K_v1.5$ $IC_{50}$ 293 nM

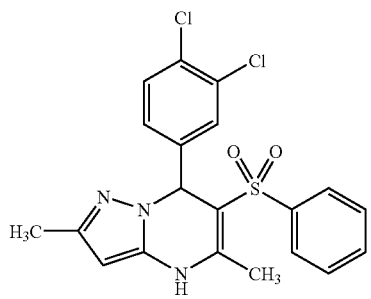

Following a procedure similar to that described in Example 1, 7-(3,4-dichlorophenyl)-2,5-dimethyl-6-(phenylsulfonyl)-4,7-dihydropyrazolo[1,5-a]pyrimidine was obtained as a white solid. LC-MS found: $(M+1)^+=434.16$.

Example 4

6-(4-Chlorophenylsulfonyl)-7-(3,4-dichlorophenyl)-5-methyl-2-(trifluoromethyl)-4,7-dihydropyrazolo[1,5-a]pyrimidine Isomer 1: $K_v1.5$ $IC_{50}$ 180 nM Isomer 2: $K_v1.5$% inhibition: 36.2% at 0.3 μM

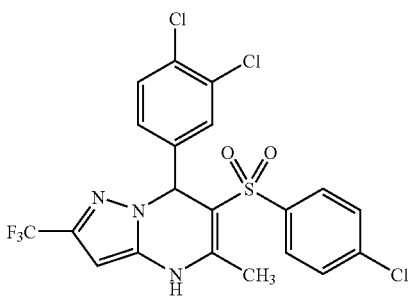

Following a procedure similar to that described in Example 1, 6-(4-chlorophenylsulfonyl)-7-(3,4-dichlorophenyl)-5-methyl-2-(trifluoromethyl)-4,7-dihydropyrazolo[1,5-a]pyrimidine was obtained as a white solid. LC-MS found: $(M+1)^+=$ 522.2.

Example 5

7-(3,4-Dichlorophenyl)-2,5-dimethyl-6-tosyl-4,7-dihydropyrazolo[1,5-a]pyrimidine Isomer 1: $K_v1.5$ IC$_{50}$ 48 nM Isomer 2: $K_v1.5$ IC$_{50}$ 131 nM

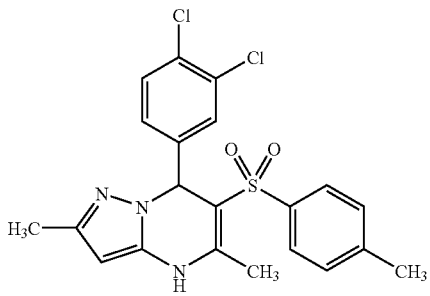

Following a procedure similar to that described in Example 1, 7-(3,4-dichlorophenyl)-2,5-dimethyl-6-tosyl-4,7-dihydropyrazolo[1,5-a]pyrimidine was obtained as a white solid. LC-MS found: $(M+1)^+=448.15$.

Example 6

7-(Benzo[d][1,3]dioxol-5-yl)-2,5-dimethyl-6-(phenylsulfonyl)-4,7-dihydropyrazolo[1,5-a]pyrimidine Racemate: $K_v1.5$% inhibition: 6.1% at 0.3 μM

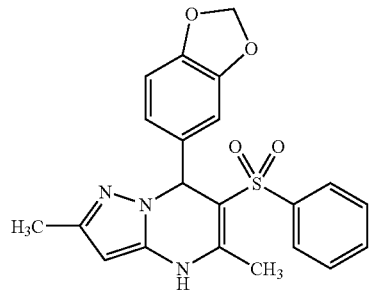

Following a procedure similar to that described in Example 1, 7-(benzo[d][1,3]dioxol-5-yl)-2,5-dimethyl-6-(phenylsulfonyl)-4,7-dihydropyrazolo[1,5-a]pyrimidine was obtained as a white solid. LC-MS found: $(M+1)^+=410.26$.

Example 7

7-(4-Chloro-3-fluorophenyl)-2,5-dimethyl-6-(phenylsulfonyl)-4,7-dihydropyrazolo[1,5-a]pyrimidine Isomer 1: $K_v1.5$% inhibition: 90.8% at 0.3 μM Isomer 2: $K_v1.5$% inhibition: 32.4% at 0.3 μM

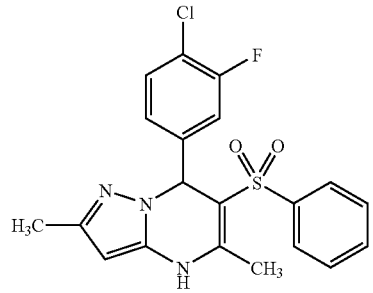

Following a procedure similar to that described in Example 1, 7-(4-chloro-3-fluorophenyl)-2,5-dimethyl-6-(phenylsulfonyl)-4,7-dihydropyrazolo[1,5-a]pyrimidine was obtained as a white solid. LC-MS-found: $(M+1)^+=418.1$.

Example 8

7-(3,4-Dichlorophenyl)-6-(4-methoxyphenylsulfonyl)-2,5-dimethyl-4,7-dihydropyrazolo[1,5-a]pyrimidine Isomer 1: $K_v1.5$ IC$_{50}$ 23 nM Isomer 2: $K_v1.5$ IC$_{50}$ 174 nM

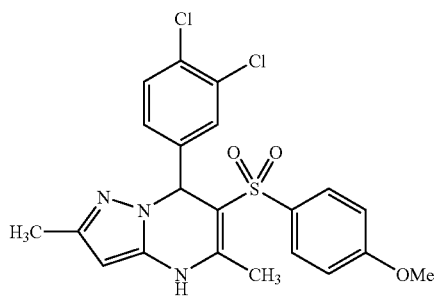

Following a procedure similar to that described in Example 1, 7-(3,4-dichlorophenyl)-6-(4-methoxyphenylsulfonyl)-2,5-dimethyl-4,7-dihydropyrazolo[1,5-a]pyrimidine was obtained as a white solid. LC-MS found: $(M+1)^+=464.21$.

Example 9

7-(3,4-Dichlorophenyl)-2,5-dimethyl-6-(4-(trifluoromethyl)phenylsulfonyl)-4,7-dihydropyrazolo[1,5-a]pyrimidine Isomer 1: $K_v1.5$ IC$_{50}$ 234 nM Isomer 2: $K_v1.5$% inhibition: 59.7% at 0.3 μM

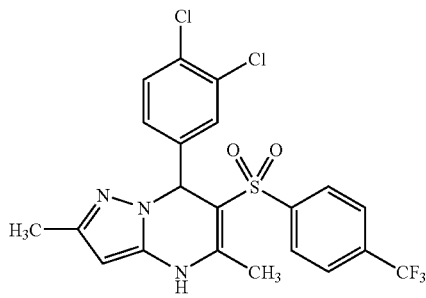

Following a procedure similar to that described in Example 1, 7-(3,4-dichlorophenyl)-2,5-dimethyl-6-(4-(trifluoromethyl)phenylsulfonyl)-4,7-dihydropyrazolo[1,5-a]pyrimidine was obtained as a white solid. LC-MS found: (M+1)$^+$=502.17.

Example 10

6-(Cyclohexylsulfonyl)-7-(3,4-dichlorophenyl)-2,5-dimethyl-4,7-dihydropyrazolo[1,5-a]pyrimidine Isomer 1: K$_v$1.5 IC$_{50}$ 77 nM Isomer 2: K$_v$1.5% inhibition: 59.3% at 0.3 μM

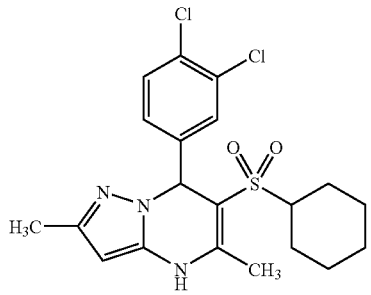

Following a procedure similar to that described in Example 1, 6-(cyclohexylsulfonyl)-7-(3,4-dichlorophenyl)-2,5-dimethyl-4,7-dihydropyrazolo[1,5-a]pyrimidine was obtained as a white solid. LC-MS found: (M+1)$^+$=440.17.

Example 11

7-(3,4-Dichlorophenyl)-2,5-dimethyl-6-(pyridin-2-ylsulfonyl)-4,7-dihydropyrazolo[1,5-a]pyrimidine Isomer 1: K$_v$1.5% inhibition: 72.5% at 0.3 μM Isomer 2: K$_v$1.5% inhibition: 21.5% at 0.3 μM

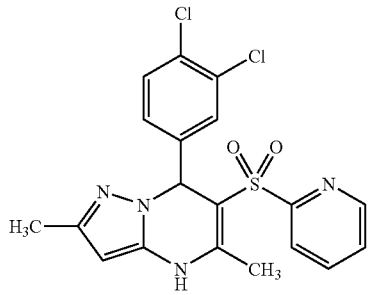

Following a procedure similar to that described in Example 1, 7-(3,4-dichlorophenyl)-2,5-dimethyl-6 (pyridin-2-ylsulfonyl)-4,7-dihydropyrazolo[1,5-a]pyrimidine was obtained as a white solid. LC-MS found: (M+1)$^+$=435.11.

Example 12

7-(3,4-Dichlorophenyl)-6-(4-fluorophenylsulfonyl)-5-methyl-2-(trifluoromethyl)-4,7-dihydropyrazolo[1,5-a]pyrimidine Isomer 1: K$_v$1.5 IC$_{50}$ 142 nM Isomer 2: K$_v$1.5% inhibition: 71.1% at 0.3 μM

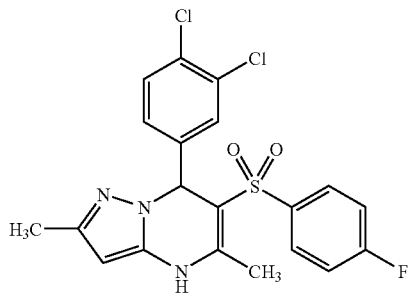

Following a procedure similar to that described in Example 1, 7-(3,4-dichlorophenyl)-6-(4-fluorophenylsulfonyl)-5-methyl-2-(trifluoromethyl)-4,7-dihydropyrazolo[1,5-a]pyrimidine was obtained as a white solid. LC-MS found: (M+1)$^+$=506.17.

Example 13

7-(3,4-Dichlorophenyl)-6-(isopropylsulfonyl)-2,5-dimethyl-4,7-dihydropyrazolo[1,5-a]pyrimidine Racemate: K$_v$1.5% inhibition: 15.4% at 0.3 μM

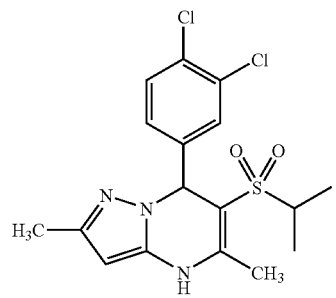

Following a procedure similar to that described in Example 1, 7-(3,4-dichlorophenyl)-6-(isopropylsulfonyl)-2,5-dimethyl-4,7-dihydropyrazolo[1,5-a]pyrimidine was obtained as a white solid. LC-MS found: (M+1)$^+$=400.2.

Example 14

6-(Benzylsulfonyl)-7-(3,4-dichlorophenyl)-2,5-dimethyl-4,7-dihydropyrazolo[1,5-a]pyrimidine Racemate: $K_v1.5$% inhibition: 50.4% at 0.3 μM

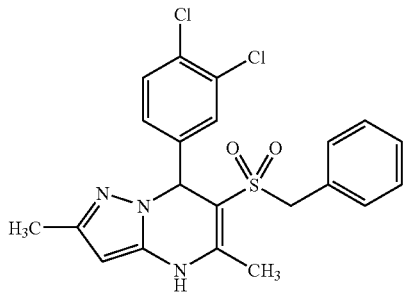

Following a procedure similar to that described in Example 1, 6-(benzylsulfonyl)-7-(3,4-dichlorophenyl)-2,5-dimethyl-4,7-dihydropyrazolo[1,5-a]pyrimidine was obtained as a white solid. LC-MS found: $(M+1)^+$=448.2.

Example 15

6-(Benzylsulfonyl)-7-(3,4-dichlorophenyl)-2,5-dimethylpyrazolo[1,5-a]pyrimidine

Racemate: $K_v1.5$% inhibition: 8.5% at 0.3 μM

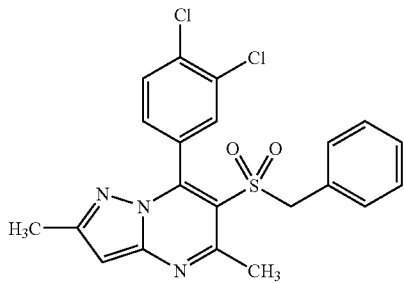

Following a procedure similar to that described in Example 1, 6-(benzylsulfonyl)-7-(3,4-dichlorophenyl)-2,5-dimethylpyrazolo[1,5-a]pyrimidine was obtained as a side product. LC-MS found: $(M+1)^+$=446.16.

Example 16

6-(Benzylsulfonyl)-7-(3,4-dichlorophenyl)-5-methyl-2-(trifluoromethyl)-4,7-dihydropyrazolo[1,5-a]pyrimidine Racemate: $K_v1.5$% inhibition: 37.2% at 0.3 μM

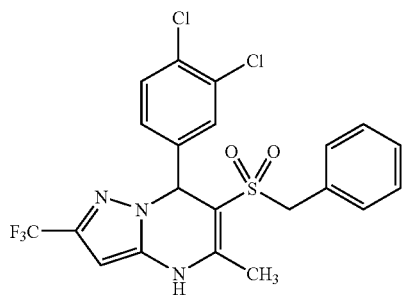

Following a procedure similar to that described in Example 1, 6-(benzylsulfonyl)-7-(3,4-dichlorophenyl)-5-methyl-2-(trifluoromethyl)-4,7-dihydropyrazolo[1,5-a]pyrimidine was obtained as a white solid. LC-MS found: $(M+1)^+$=502.18.

Example 17

7-(3-Chlorophenyl)-6-(4-methoxyphenylsulfonyl)-2,5-dimethyl-4,7-dihydropyrazolo[1,5-a]pyrimidine Isomer 1: $K_v1.5$ $IC_{50}$ 256 nM Isomer 2: $K_v1.5$% inhibition: 18.1% at 0.3 μM

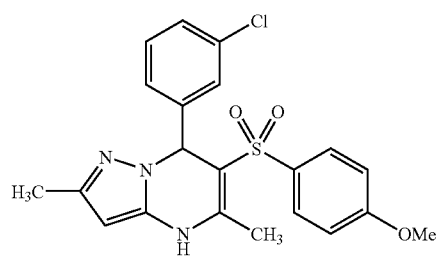

Following a procedure similar to that described in Example 1, 7-(3-chlorophenyl)-6-(4-methoxyphenylsulfonyl)-2,5-dimethyl-4,7-dihydropyrazolo[1,5-a]pyrimidine was obtained as a white solid. LC-MS found: $(M+1)^+$=430.20.

Example 18

6-(Butylsulfonyl)-7-(3,4-dichlorophenyl)-2,5-dimethyl-4,7-dihydropyrazolo[1,5-a]pyrimidine Isomer 1: $K_v1.5$% inhibition: 84.6% at 0.3 μM Isomer 2: $K_v1.5$% inhibition: 28.8% at 0.3 μM

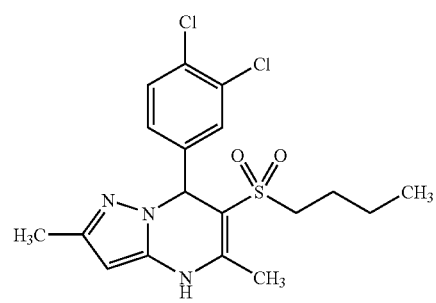

Following a procedure similar to that described in Example 1, 6-(butylsulfonyl)-7-(3,4-dichlorophenyl)-2,5-dimethyl-4,7-dihydropyrazolo[1,5-a]pyrimidine was obtained as a white solid. LC-MS found: $(M+1)^+$=414.18.

Example 19

7-(4-Chlorophenyl)-6-(4-methoxyphenylsulfonyl)-2,5-dimethyl-4,7-dihydropyrazolo[1,5-a]pyrimidine Isomer 1: $K_v1.5$ $IC_{50}$ 55 nM Isomer 2: $K_v1.5$% inhibition: 42.3% at 0.3 μM

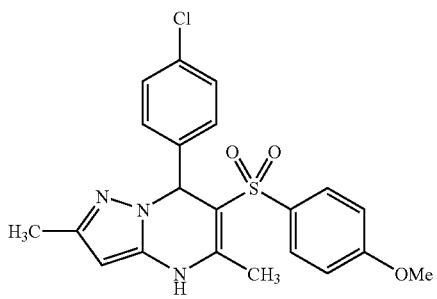

Following a procedure similar to that described in Example 1, 7-(4-chlorophenyl)-6-(4-methoxyphenylsulfonyl)-2,5-dimethyl-4,7-dihydropyrazolo[1,5-a]pyrimidine was obtained as a white solid. LC-MS found: (M+1)⁺=430.19.

Example 20

7-(5-Chlorothiophen-2-yl)-5-methyl-6-(phenylsulfonyl)-2-(trifluoromethyl)-4,7-dihydropyrazolo[1,5-a]pyrimidine Racemate: $K_v$1.5% inhibition: 7.8% at 0.3 μM

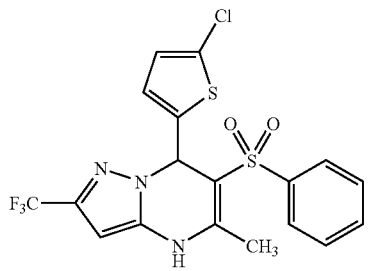

Following a procedure similar to that described in Example 1, 7-(5-chlorothiophen-2-yl)-5-methyl-6-(phenylsulfonyl)-2-(trifluoromethyl)-4,7-dihydropyrazolo[1,5-a]pyrimidine was obtained as a white solid. LC-MS found: (M+1)⁺=460.1.

Example 21

5-Methyl-6-(phenylsulfonyl)-7-(4-(pyrrolidin-1-yl)phenyl)-2-(trifluoromethyl)-4,7-dihydropyrazolo[1,5-a]pyrimidine Racemate: $K_v$1.5% inhibition: 11.1% at 0.3 μM

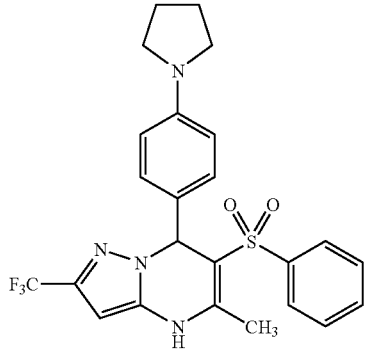

Following a procedure similar to that described in Example 1, 5-methyl-6-(phenylsulfonyl)-7-(4-(pyrrolidin-1-yl)phenyl)-2-(trifluoromethyl)-4,7-dihydropyrazolo[1,5-a]pyrimidine was obtained as a white solid. LC-MS found: (M+1)⁺= 489.29.

Example 22

7-(4-Fluoro-3-methylphenyl)-5-methyl-6-(phenylsulfonyl)-2-(trifluoromethyl)-4,7-dihydropyrazolo[1,5-a]pyrimidine Racemate: $K_v$1.5% inhibition: 30.7% at 0.3 μM

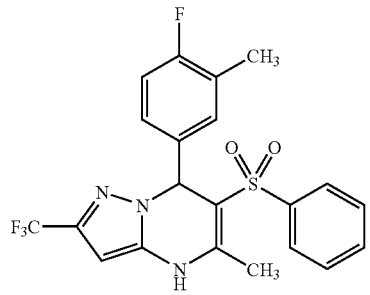

Following a procedure similar to that described in Example 1, 7-(4-fluoro-3-methylphenyl)-5-methyl-6-(phenylsulfonyl)-2-(trifluoromethyl)-4,7-dihydropyrazolo[1,5-a]pyrimidine was obtained as a white solid. LC-MS found: (M+1)⁺= 452.26.

Example 23

6-(4-Methoxyphenylsulfonyl)-2,5-dimethyl-7-(1-methyl-1H-benzo[d]imidazol-2-yl)-4,7-dihydropyrazolo[1,5-a]pyrimidine Isomer 1: $K_v$1.5% inhibition: 6.5% at 0.3 μM Isomer 2: $K_v$1.5% inhibition: 16.6% at 0.3 μM

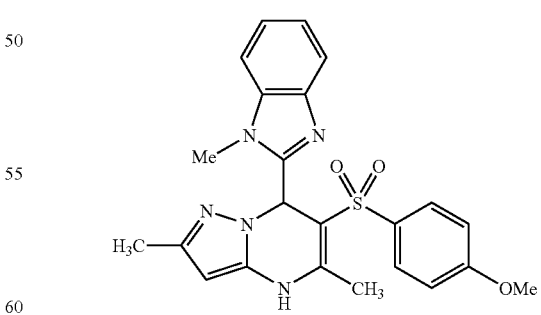

Following a procedure similar to that described in Example 1, 6-(4-methoxyphenylsulfonyl)-2,5-dimethyl-7-(1-methyl-1H-benzo[d]imidazol-2-yl)-4,7-dihydropyrazolo[1,5-a]pyrimidine was obtained as a white solid. LC-MS found: (M+1)⁺=450.3.

Example 24

7-(3-Fluoro-4-methylphenyl)-6-(4-methoxyphenyl-sulfonyl)-2,5-dimethyl-4,7-dihydropyrazolo[1,5-a]pyrimidine Isomer 1: $K_v1.5$ $IC_{50}$ 148 nM.

Isomer 2: $K_v1.5$ $IC_{50}$ 322 nM.

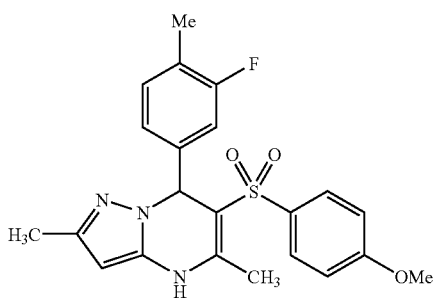

Following a procedure similar to that described in Example 1, 7-(3-fluoro-4-methylphenyl)-6-(4-methoxyphenylsulfonyl)-2,5-dimethyl-4,7-dihydropyrazolo[1,5-a]pyrimidine was obtained as a white solid. LC-MS found: $(M+1)^+=$ 428.28.

Example 25

7-(4-Chlorophenyl)-6-(4-methoxyphenylsulfonyl)-5-methyl-2-(trifluoromethyl)-4,7-dihydropyrazolo[1,5-a]pyrimidine Isomer 1: $K_v1.5$% inhibition: 85.6% at 0.3 μM Isomer 2: $K_v1.5$% inhibition: 82.9% at 0.3 μM

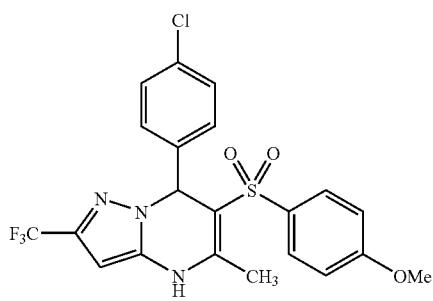

Following a procedure similar to that described in Example 1, 7-(4-chlorophenyl)-6-(4-methoxyphenylsulfonyl)-5-methyl-2-(trifluoromethyl)-4,7-dihydropyrazolo[1,5-a]pyrimidine was obtained as a white solid. LC-MS found: $(M+1)^+=$ 484.22.

Example 26

7-(4-Chlorophenyl)-5-methyl-6-(phenylsulfonyl)-2-(trifluoromethyl)-4,7-dihydropyrazolo[1,5-a]pyrimidine Isomer 1: $K_v1.5$% inhibition: 85.8% at 0.3 μM Isomer 2: $K_v1.5$% inhibition: 85.9% at 0.3 μM

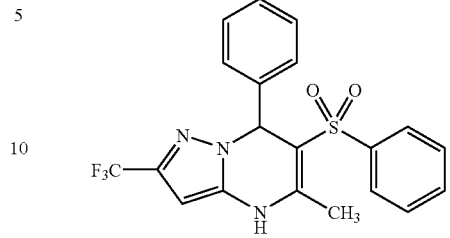

Following a procedure similar to that described in Example 1, 7-(4-chlorophenyl)-5-methyl-6-(phenylsulfonyl)-2-(trifluoromethyl)-4,7-dihydropyrazolo[1,5-a]pyrimidine was obtained as a white solid. LC-MS found: $(M+1)^+=454.18$.

Example 27

7-(4-Chlorophenyl)-6-(4-fluorophenylsulfonyl)-5-methyl-2-(trifluoromethyl)-4,7-dihydropyrazolo[1,5-a]pyrimidine Isomer 1: $K_v1.5$% inhibition: 47.6% at 0.3 μM Isomer 2: $K_v1.5$ $IC_{50}$ 92 nM

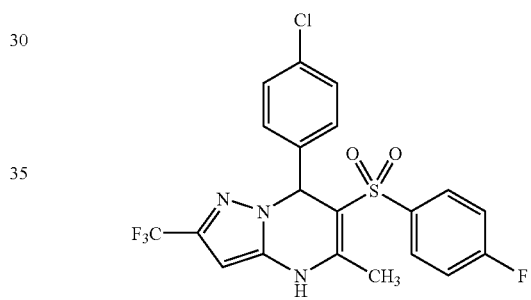

Following a procedure similar to that described in Example 1, 7-(4-chlorophenyl)-6-(4-fluorophenylsulfonyl)-5-methyl-2-(trifluoromethyl)-4,7-dihydropyrazolo[1,5-a]pyrimidine was obtained as a white solid. LC-MS found: $(M+1)^+=$ 472.20.

Example 28

7-(4-Chlorophenyl)-5-methyl-6-tosyl-2-(trifluoromethyl)-4,7-dihydropyrazolo[1,5-a]pyrimidine Isomer 1: $K_v1.5$% inhibition: 77.4% at 0.3 μM Isomer 2: $K_v1.5$% inhibition: 83.4% at 0.3 μM

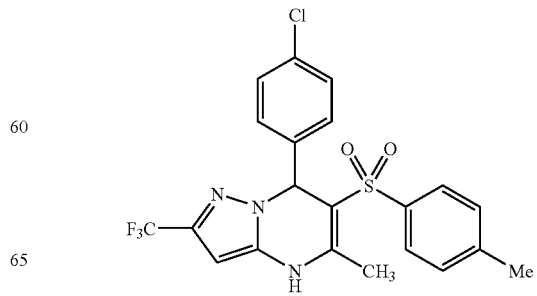

Following a procedure similar to that described in Example 1, 7-(4-chlorophenyl)-5-methyl-6-tosyl-2-(trifluoromethyl)-4,7-dihydropyrazolo[1,5-a]pyrimidine was obtained as a white solid. LC-MS found: (M+1)$^+$=468.3.

Example 29

7-(4-Chlorophenyl)-6-(cyclohexylsulfonyl)-5-methyl-2-(trifluoromethyl)-4,7-dihydropyrazolo[1,5-a]pyrimidine Isomer 1: $K_v1.5$ IC$_{50}$ 204 nM Isomer 2: $K_v1.5$% inhibition: 87.9% at 0.3 μM

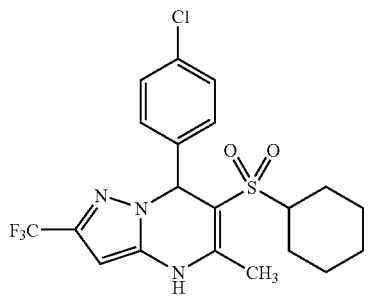

Following a procedure similar to that described in Example 1, 7-(4-chlorophenyl)-6-(cyclohexylsulfonyl)-5-methyl-2-(trifluoromethyl)-4,7-dihydropyrazolo[1,5-a]pyrimidine was obtained as a white solid. LC-MS found: (M+1)$^+$=460.27.

Example 30

6-(Butylsulfonyl)-7-(4-chlorophenyl)-5-methyl-2-(trifluoromethyl)-4,7-dihydropyrazolo[1,5-a]pyrimidine Isomer 1: $K_v1.5$ IC$_{50}$ 210 nM Isomer 2: $K_v1.5$% inhibition: 77% at 0.3 μM

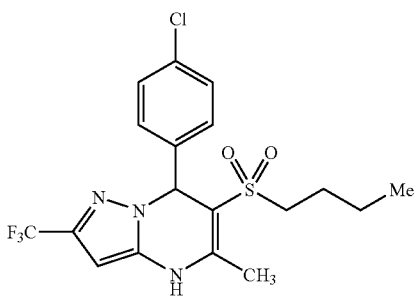

Following a procedure similar to that described in Example 1, 6-(butylsulfonyl)-7-(4-chlorophenyl)-5-methyl-2-(trifluoromethyl)-4,7-dihydropyrazolo[1,5-a]pyrimidine was obtained as a white solid. LC-MS found: (M+1)$^+$=460.27.

Example 31

7-(4-Chlorophenyl)-6-(4-chlorophenylsulfonyl)-5-methyl-2-(trifluoromethyl)-4,7-dihydropyrazolo[1,5-a]pyrimidine Isomer 1: $K_v1.5$% inhibition: 82.7% at 0.3 μM Isomer 2: $K_v1.5$% inhibition: 81.9% at 0.3 μM

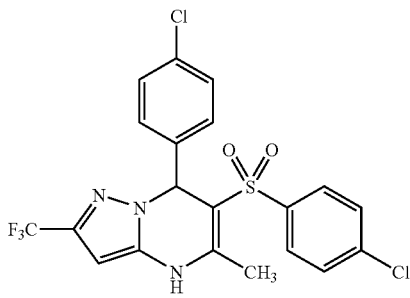

Following a procedure similar to that described in Example 1, 7-(4-chlorophenyl)-6-(4-chlorophenylsulfonyl)-5-methyl-2-(trifluoromethyl)-4,7-dihydropyrazolo[1,5-a]pyrimidine was obtained as a white solid. LC-MS found: (M+1)$^+$=488.20.

Example 32

7-(3-Fluoro-4-methylphenyl)-6-(4-methoxyphenylsulfonyl)-5-methyl-2-(trifluoromethyl)-4,7-dihydropyrazolo[1,5-a]pyrimidine Isomer 1: $K_v1.5$% inhibition: 81.8% at 0.3 μM Isomer 2: $K_v1.5$% inhibition: 72.7% at 0.3 μM

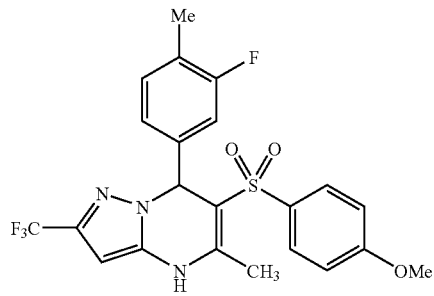

Following a procedure similar to that described in Example 1, 7-(3-fluoro-4-methylphenyl)-6-(4-methoxyphenylsulfonyl)-5-methyl-2-(trifluoromethyl)-4,7-dihydropyrazolo[1,5-a]pyrimidine was obtained as a white solid. LC-MS found: (M+1)$^+$=482.27.

Example 33

7-(4-Chloro-3-fluorophenyl)-5-methyl-6-(phenylsulfonyl)-2-(trifluoromethyl)-4,7-dihydropyrazolo[1,5-a]pyrimidine Isomer 1: $K_v1.5$% inhibition: 75.5% at 0.3 μM Isomer 2: $K_v1.5$% inhibition: 76.5% at 0.3 μM

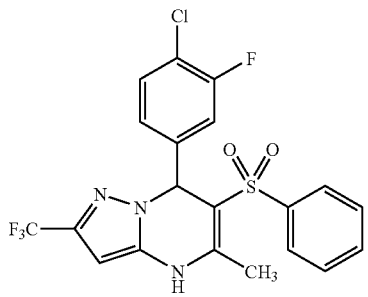

Following a procedure similar to that described in Example 1, 7-(4-chloro-3-fluorophenyl)-5-methyl-6-(phenylsulfo-

Example 34

6-(4-Chlorophenylsulfonyl)-5-methyl-7-p-tolyl-2-(trifluoromethyl)-4,7-dihydropyrazolo[1,5-a]pyrimidine Racemate: $K_v1.5$% inhibition: 37.6% at 0.3 μM

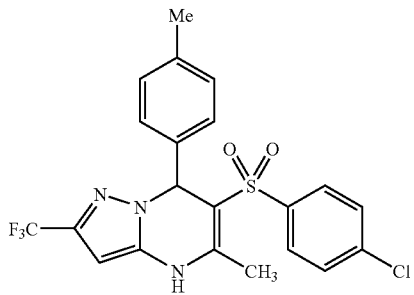

Following a procedure similar to that described in Example 1, 6-(4-chlorophenylsulfonyl)-5-methyl-7-p-tolyl-2-(trifluoromethyl)-4,7-dihydropyrazolo[1,5-a]pyrimidine was obtained as a white solid. LC-MS found: $(M+1)^+$=468.19.

Example 35

6-(4-Chlorophenylsulfonyl)-5-methyl-7-phenyl-2-(trifluoromethyl)-4,7-dihydropyrazolo[1,5-a]pyrimidine Isomer 1: $K_v1.5$ $IC_{50}$ 277 nM Isomer 2: $K_v1.5$ $IC_{50}$ 252 nM

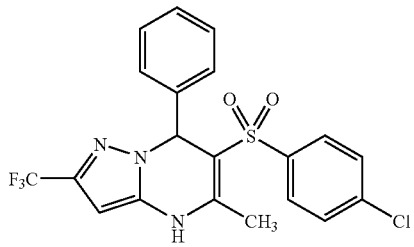

Following a procedure similar to that described in Example 1, 6-(4-chlorophenylsulfonyl)-5-methyl-7-phenyl-2-(trifluoromethyl)-4,7-dihydropyrazolo[1,5-a]pyrimidine was obtained as a white solid. LC-MS found: $(M+1)^+$=454.18.

Example 36

7-(4-Fluorophenyl)-5-methyl-6-(phenylsulfonyl)-2-(trifluoromethyl)-4,7-dihydropyrazolo[1,5-a]pyrimidine Isomer 1: $K_v1.5$ $IC_{50}$ 208 nM Isomer 2: $K_v1.5$% inhibition: 49% at 0.3 μM

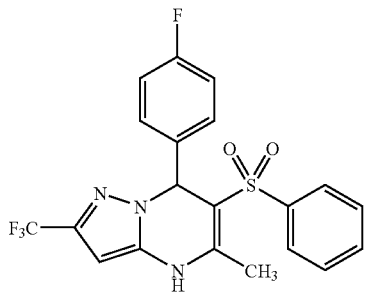

Following a procedure similar to that described in Example 1, 7-(4-fluorophenyl)-5-methyl-6-(phenylsulfonyl)-2-(trifluoromethyl)-4,7-dihydropyrazolo[1,5-a]pyrimidine was obtained as a white solid. LC-MS found: $(M+1)^+$=438.25.

Example 37

7-(3,4-Dichlorophenyl)-N-(4-methoxyphenyl)-2,5-dimethyl-4,7-dihydropyrazolo[1,5-a]pyrimidine-6-sulfonamide Racemate: $K_v1.5$% inhibition: 25% at 0.3 μM

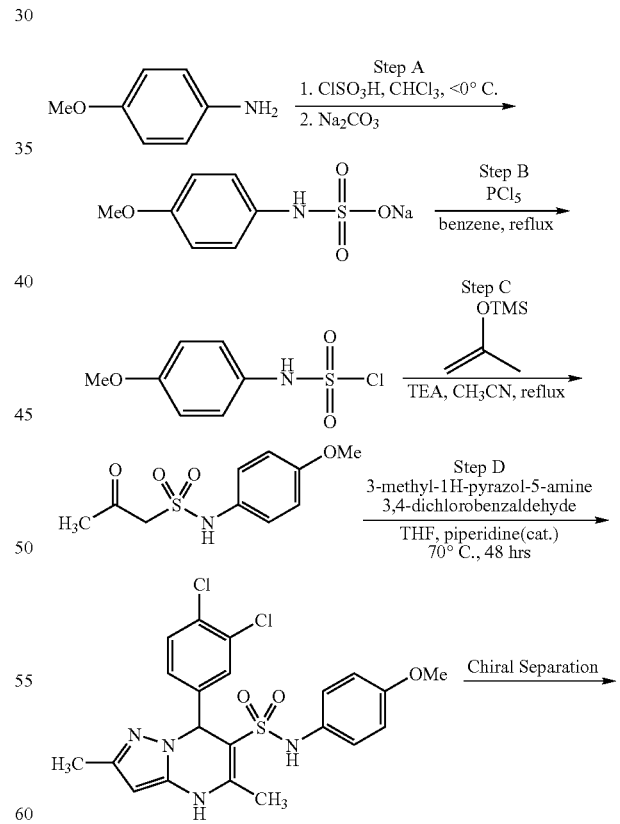

7-(3,4-Dichlorophenyl)-N-(4-methoxyphenyl)-2,5-dimethyl-4,7-dihydropyrazolo[1,5-a]pyrimidine-6-sulfonamide was synthesized following the route outlined above:

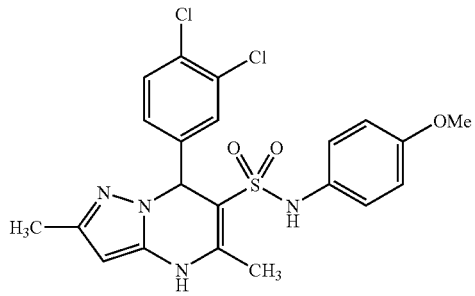

Step A:

4-Methoxybenzenamine (36.9 g, 0.3 mol) in chloroform (300 mL) was cooled with salt-ice to below 0° C. and chlorosulfonic (11.6 g, 0.1 mol) was added dropwise so as to maintain the temperature not to exceed 0° C. After all acid was added, the mixture was filtered. Solid collected was added to a solution of sodium carbonate (15.9 g, 0.15 mol) in 200 mL water. Aqueous solution washed with dichloromethane four times. Water was removed from the aqueous phase to leave a solid as product, sodium 4-methoxyphenylsulfamate.

Step B:

To sodium 4-methoxyphenylsulfamate (10.0 g 44 mmol) suspended in benzene (100 mL) was added $PCl_5$ (9.2 g, 44 mmol) cautiously. The mixture was slowly warmed up and refluxed for 15 hrs. After cooling to rt., the mixture was filtered through a pad of Celite and solvent was removed from filtrate to leave a brown oil as 4-methoxyphenylsulfamoyl chloride, which was used in the next step without further purification.

Step C:

4-Methoxyphenylsulfamoyl chloride (11.0 g, crude from Step B) in acetonitrile (5.0 mL) was added to a mixture of trimethyl(prop-1-en-2-yloxy)silane (0.85 g, 85% purity, 5.56 mmol) and triethylamine (2.0 mL) in acetonitrile (10 mL) at rt. Upon addition, the reaction was warmed up and refluxed for 2 hrs. After cooling to rt., solvent was removed under reduced pressure and product was purified by flash chromatography (silica gel, ethyl acetate/hexanes gradient) to give N-(4-methoxyphenyl)-2-oxopropane-1-sulfonamide as a solid. LC-MS found: $(M+1)^+=244.2$.

Step D:

N-(4-Methoxyphenyl)-2-oxopropane-1-sulfonamide (100 mg, 0.41 mmol, from Step C), 3-methyl-1H-pyrazol-5-amine (40 mg, 0.41 mmol) and 3,4-dichlorobenzaldehyde (72 mg, 0.41 mmol) were dissolved in THF (6 mL), to which was added a catalytic amount of piperidine (3 drops). The reaction in a sealed tube was stirred at 70° C. for about 36 hrs. After cooling to rt., solvent was removed and crude product was purified by HPLC (acetonitrile-water, 5% to 95% gradient) to provide pure product 7-(3,4-dichlorophenyl)-N-(4-methoxyphenyl)-2,5-dimethyl-4,7-dihydropyrazolo[1,5-a]pyrimidine-6-sulfonamide as a solid. LC-MS found: $(M+1)^+= 479.21$.

Example 38

N-Cyclohexyl-7-(3,4-dichlorophenyl)-2,5-dimethyl-4,7-dihydropyrazolo[1,5-a]pyrimidine-6-sulfonamide Isomer 1: $K_v1.5$ $IC_{50}$ 108 nM Isomer 2: $K_v1.5$% inhibition: 27.6% at 0.3 μM

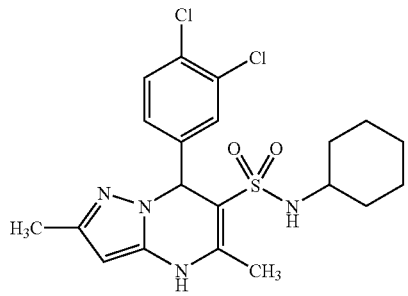

Following a procedure similar to that described in Example 37, N-cyclohexyl-7-(3,4-dichlorophenyl)-2,5-dimethyl-4,7-dihydropyrazolo[1,5-a]pyrimidine-6-sulfonamide was obtained as a white solid. LC-MS found: $(M+1)^+=454.18$.

Example 39

7-(3,4-Dichlorophenyl)-6-(3-methoxyphenylsulfonyl)-5-methyl-2-(trifluoromethyl)-4,7-dihydropyrazolo[1,5-a]pyrimidine Isomer 1: $K_v1.5$% inhibition: 78.6% at 0.3 μM Isomer 2: $K_v1.5$% inhibition: 79.6% at 0.3 μM

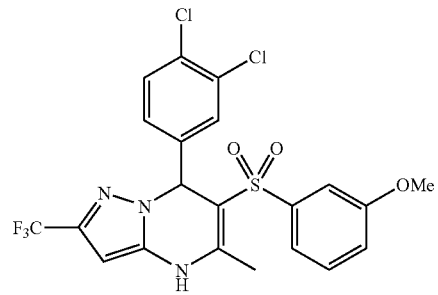

Following a procedure similar to that described in Example 1, 7-(3,4-dichlorophenyl)-6-(3-methoxyphenylsulfonyl)-5-methyl-2-(trifluoromethyl)-4,7-dihydropyrazolo[1,5-a]pyrimidine was obtained as a white solid. LC-MS found: $(M+1)^+= 518.2$.

Example 40

7-(4-Chlorophenyl)-6-(3-methoxyphenylsulfonyl)-5-methyl-2-(trifluoromethyl)-4,7-dihydropyrazolo[1,5-a]pyrimidine Isomer 1: $K_v1.5$% inhibition: 94.4% at 0.3 μM Isomer 2: $K_v1.5$% inhibition: 74.4% at 0.3 μM

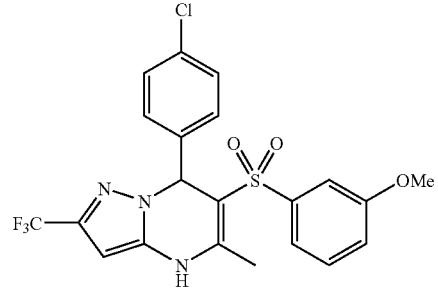

Following a procedure similar to that described in Example 1, 7-(4-chlorophenyl)-6-(3-methoxyphenylsulfonyl)-5-methyl-2-(trifluoromethyl)-4,7-dihydropyrazolo[1,5-a]pyrimidine was obtained as a white solid. LC-MS found: (M+1)$^+$=484.2.

Example 41

7-(3-Fluoro-4-methylphenyl)-6-(3-methoxyphenyl-sulfonyl)-5-methyl-2-(trifluoromethyl)-4,7-dihydro-pyrazolo[1,5-a]pyrimidine Isomer 1: K$_v$1.5% inhibition: 84.4% at 0.3 μM Isomer 2: K$_v$1.5% inhibition: 85.8% at 0.3 μM

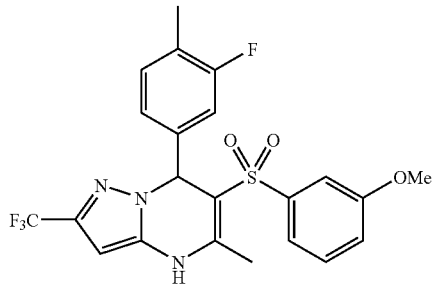

Following a procedure similar to that described in Example 1, 7-(3-fluoro-4-methylphenyl)-6-(3-methoxyphenylsulfonyl)-5-methyl-2-(trifluoromethyl)-4,7-dihydropyrazolo[1,5-a]pyrimidine was obtained as a white solid. LC-MS found: (M+1)$^+$=482.2.

Example 42

6-(4-Chlorophenylsulfonyl)-7-(3-fluoro-4-methylphenyl)-5-methyl-2-(trifluoromethyl)-4,7-dihydro-pyrazolo[1,5-a]pyrimidine Isomer 1: K$_v$1.5% inhibition: 94.5% at 0.3 μM Isomer 2: K$_v$1.5% inhibition: 92.9% at 0.3 μM

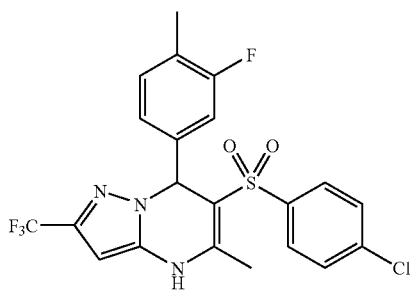

Following a procedure similar to that described in Example 1, 6-(4-chlorophenylsulfonyl)-7-(3-fluoro-4-methylphenyl)-5-methyl-2-(trifluoromethyl)-4,7-dihydropyrazolo[1,5-a] pyrimidine was obtained as a white solid. LC-MS found: (M+1)$^+$=486.2.

Example 43

6-(4-Chlorophenylsulfonyl)-7-(4-fluorophenyl)-5-methyl-2-(trifluoromethyl)-4,7-dihydropyrazolo[1,5-a]pyrimidine Isomer 1: K$_v$1.5% inhibition: 83.6% at 0.3 μM Isomer 2: K$_v$1.5% inhibition: 87.3% at 0.3 μM

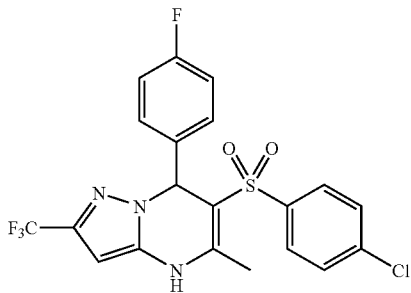

Following a procedure similar to that described in Example 1, 6-(4-chlorophenylsulfonyl)-7-(4-fluorophenyl)-5-methyl-2-(trifluoromethyl)-4,7-dihydropyrazolo[1,5-a]pyrimidine was obtained as a white solid. LC-MS found: (M+1)$^+$=472.2.

Example 44

6-(4-Chlorophenylsulfonyl)-7-cyclohexyl-5-methyl-2-(trifluoromethyl)-4,7-dihydropyrazolo[1,5-a]pyrimidine Isomer 1: K$_v$1.5 IC$_{50}$ 202 nM.

Isomer 2: K$_v$1.5% inhibition: 21.3% at 0.3 μM

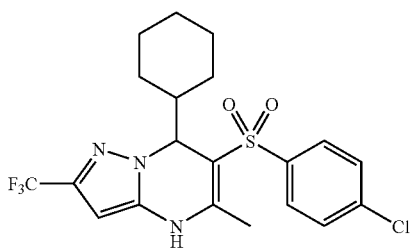

Following a procedure similar to that described in Example 1, 6-(4-chlorophenylsulfonyl)-7-cyclohexyl-5-methyl-2-(trifluoromethyl)-4,7-dihydropyrazolo[1,5-a]pyrimidine was obtained as a white solid. LC-MS found: (M+1)$^+$=460.3.

Example 45

6-(4-Chlorophenylsulfonyl)-7-isobutyl-5-methyl-2-(trifluoromethyl)-4,7-dihydropyrazolo[1,5-a]pyrimidine Isomer 1: K$_v$1.5 IC$_{50}$ 249 nM.

Isomer 2: K$_v$1.5% inhibition: 48% at 0.3 μM

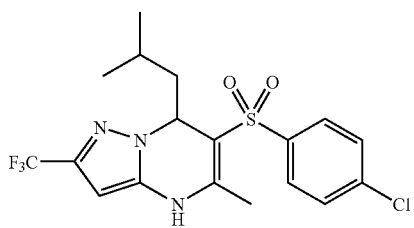

Following a procedure similar to that described in Example 1, 6-(4-chlorophenylsulfonyl)-7-isobutyl-5-methyl-2-(trifluoromethyl)-4,7-dihydropyrazolo[1,5-a]pyrimidine was obtained as a white solid. LC-MS found: $(M+1)^+=434.3$.

Example 46

7-(4-Chlorophenyl)-6-(2-methoxyphenylsulfonyl)-5-methyl-2-(trifluoromethyl)-4,7-dihydropyrazolo[1,5-a]pyrimidine Isomer 1: $K_v1.5$% inhibition: 78.1% at 0.3 µM Isomer 2: $K_v1.5$% inhibition: 74.7% at 0.3 µM

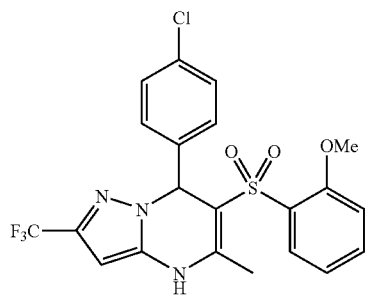

Following a procedure similar to that described in Example 1, 7-(4-chlorophenyl)-6-(2-methoxyphenylsulfonyl)-5-methyl-2-(trifluoromethyl)-4,7-dihydropyrazolo[1,5-a]pyrimidine was obtained as a white solid. LC-MS found: $(M+1)^+=484.2$.

Example 47

7-(4-Chlorophenyl)-5-methyl-6-(pyridin-2-ylsulfonyl)-2-(trifluoromethyl)-4,7-dihydropyrazolo[1,5-a]pyrimidine Isomer 1: $K_v1.5$ $IC_{50}$ 197 nM Isomer 2: $K_v1.5$% inhibition: 75.8% at 0.3 µM

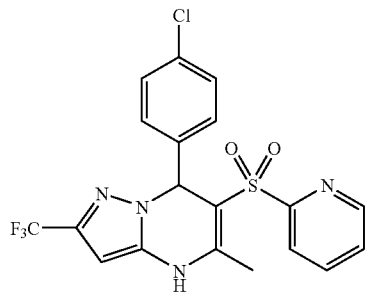

Following a procedure similar to that described in Example 1, 7-(4-chlorophenyl)-5-methyl-6-(pyridin-2-ylsulfonyl)-2-(trifluoromethyl)-4,7-dihydropyrazolo[1,5-a]pyrimidine was obtained as a white solid. LC-MS found: $(M+1)^+=455.2$.

Example 48

(7-(3,4-Dichlorophenyl)-6-(4-methoxyphenylsulfonyl)-2-(trifluoromethyl)-4,7-dihydropyrazolo[1,5-a]pyrimidin-5-yl)methanol Racemate: $K_v1.5$% inhibition: 15% at 0.3 µM

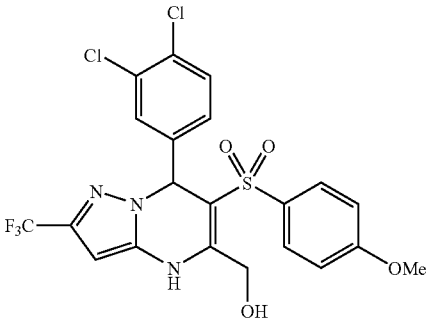

Following a procedure similar to that described in Example 1, (7-(3,4-dichlorophenyl)-6-(4-methoxyphenylsulfonyl)-2-(trifluoromethyl)-4,7-dihydropyrazolo[1,5-a]pyrimidin-5-yl)methanol was obtained as a white solid. LC-MS found: $(M+1)^+=534.1$.

Example 49

(7-(4-Chlorophenyl)-6-(4-methoxyphenylsulfonyl)-2-(trifluoromethyl)-4,7-dihydropyrazolo[1,5-a]pyrimidin-5-yl)methanol Isomer 1: $K_v1.5$% inhibition: 19.6% at 0.3 µM.

Isomer 2: $K_v1.5$% inhibition: 71.2% at 0.3 µM

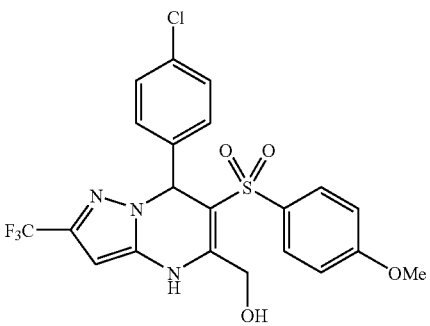

Following a procedure similar to that described in Example 1, (7-(4-chlorophenyl)-6-(4-methoxyphenylsulfonyl)-2-(trifluoromethyl)-4,7-dihydropyrazolo[1,5-a]pyrimidin-5-yl)methanol was obtained as a white solid. LC-MS found: $(M+1)^+=500.1$.

Example 50

6-(4-Chlorophenylsulfonyl)-5-methyl-7-(pyrimidin-5-yl)-2-(trifluoromethyl)-4,7-dihydropyrazolo[1,5-a]pyrimidine Isomer 1: $K_v1.5$% inhibition: 15.1% at 0.3 µM Isomer 2: $K_v1.5$% inhibition: 14.7% at 0.3 µM

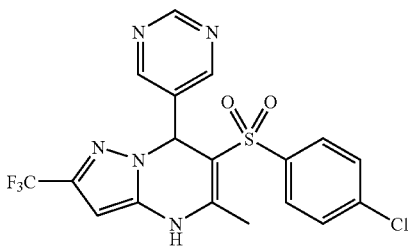

Following a procedure similar to that described in Example 1, 6-(4-chlorophenylsulfonyl)-5-methyl-7-(pyrimidin-5-yl)-2-(trifluoromethyl)-4,7-dihydropyrazolo[1,5-a]pyrimidine was obtained as a white solid. LC-MS found: $(M+1)^+=456.1$.

Example 51

7-(4-Chlorophenyl)-6-(3,4-dimethoxyphenylsulfonyl)-5-methyl-2-(trifluoromethyl)-4,7-dihydropyrazolo[1,5-a]pyrimidine Isomer 1: $K_v1.5$% inhibition: 69.2% at 0.3 μM Isomer 2: $K_v1.5$% inhibition: 79.2% at 0.3 μM

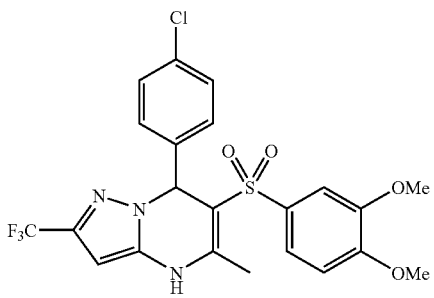

Following a procedure similar to that described in Example 1, 7-(4-chlorophenyl)-6-(3,4-dimethoxyphenylsulfonyl)-5-methyl-2-(trifluoromethyl)-4,7-dihydropyrazolo[1,5-a]pyrimidine was obtained as a white solid. LC-MS found: $(M+1)^+= 514.15$.

Example 52

7-(4-Chlorophenyl)-N-cyclohexyl-5-methyl-2-(trifluoromethyl)-4,7-dihydropyrazolo[1,5-a]pyrimidine-6-sulfonamide Racemate: $K_v1.5$% inhibition: 49.6% at 0.3 μM

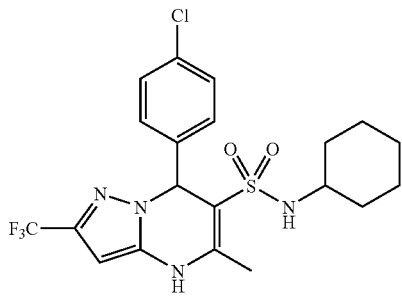

Following a procedure similar to that described in Example 37, 7-(4-chlorophenyl)-N-cyclohexyl-5-methyl-2-(trifluoromethyl)-4,7-dihydropyrazolo[1,5-a]pyrimidine-6-sulfonamide was obtained as a white solid. LC-MS found: $(M+1)^+= 475.28$.

Example 53

7-(3,4-Dichlorophenyl)-2,5-dimethyl-6-(pyrrolidin-1-ylsulfonyl)-4,7-dihydropyrazolo[1,5-a]pyrimidine Isomer 1: $K_v1.5$% inhibition: 95.7% at 0.3 μM Isomer 2: $K_v1.5$% inhibition: 54.7% at 0.3 μM The title compound was synthesized following the route outlined below.

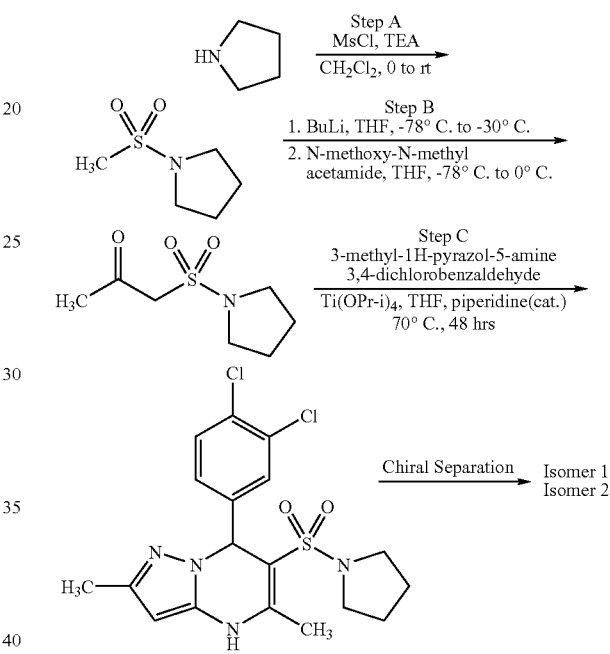

Step A: 1-(Methylsulfonyl)pyrrolidine

To a solution of pyrrolidine (8.25 g, 116 mmol) in dichloromethane (120 mL) were added triethylamine (19.0 mL, 139 mmol) followed by addition of methanesulfonyl chloride (9.0 mL, 116 mmol) at 0° C. The reaction was allowed to stir while warming up to rt. overnight, which was transferred to a separatory funnel and washed twice with 1.0N HCl and brine once. Organic phase was dried over magnesium sulfate, filtered and solvent was removed to leave a pure title product as a white solid. Step B: 1-(Pyrrolidin-1-ylsulfonyl)propan-2-one BuLi (1.6M in hexane, 22.0 mL, 35.2 mmol) was added dropwise at −75° C. to a solution of 1-(methylsulfonyl)pyrrolidine in THF (80 mL). Upon addition, the reaction was allowed to warm up to −30° C. over 20 min and stirring was continued at −30° C. for an additional hour. The reaction was cooled to −75° C. and N-methoxy-N-methyl acetamide (3.63 g, 35.2 mmol) was added dropwise. The reaction was allowed to stir while temperature was raised to 0° C. over a period of 2 hrs. HCl (1.0N, 35 mL) was added slowly. The mixture was diluted with diethyl ether (150 mL), organic phase was separated, washed with 1.0N HCl and brine, dried over magnesium sulfate, and filtered. After removal of solvent, a clear oil (solidified when cooled) was obtained as pure title product. LC-MS found: $(M+1)^+=192.2$.

Step C: 7-(3,4-Dichlorophenyl)-2,5-dimethyl-6-(pyrrolidin-1-ylsulfonyl)-4,7-dihydropyrazolo[1,5-a]pyrimidine A mixture of 1-(pyrrolidin-1-ylsulfonyl)propan-2-one (191 mg, 1.0 mmol), 3,4-dichlorobenzaldehyde (175 mg, 1.0 mmol), 3-methyl-1H-pyrazol-5-amine (97 mg, 1.0 mmol), piperidine (2 drops) and Ti(OPr-i)$_4$ (2 drops) in 1,4-dioxane (4.0 mL) in a sealed tube was stirred at 80° C. for 24 hrs. Solvent was removed and the residue was purified by flash chromatography (silica gel, 0% to 50% ethyl acetate in hexane gradient) to provide 7-(3,4-dichlorophenyl)-2,5-dimethyl-6-(pyrrolidin-1-ylsulfonyl)-4,7-dihydropyrazolo[1,5-a]pyrimidine as a white solid. LC-MS found: $(M+1)^+$= 427.10. The two enantiomers were separated with ChiralPAK AS using 20% EtOH-MeOH(1:1) in heptane as mobile phase.

Alternatively, the Bignelli reaction was carried out in two steps with higher yields. To 1-(pyrrolidin-1-ylsulfonyl)propan-2-one in THF was added an equivalent amount of 3,4-dichlorobenzaldehyde and a catalytic amount of titanium tetraisopropoxide. The reaction was stirred at 80° C. overnight. Solvent was removed and the residue was purified by silica flash chromatography (0% to 15% ethyl acetate-hexanes) to provide 4-(3,4-dichlorophenyl)-3-(pyrrolidin-1-ylsulfonyl)but-3-en-2-one. The product obtained was dissolved in 1,4-dioxane and one equivalent of 3-methyl-1H-pyrazol-5-amine was added. The reaction was stirred at 80° C. for 24-48 hrs. Solvent was removed and product was obtained after flash chromatography (silica gel, 0% to 40% ethyl acetate-hexanes).

Example 54

N-Benzyl-7-(4-chlorophenyl)-5-methyl-2-(trifluoromethyl)-4,7-dihydropyrazolo[1,5-a]pyrimidine-6-sulfonamide Racemate: K$_v$1.5% inhibition: 27.7% at 0.3 μM

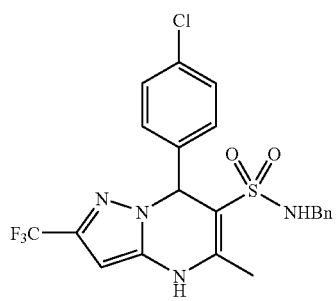

Following a procedure similar to that described in Example 53, N-benzyl-7-(4-chlorophenyl)-5-methyl-2-(trifluoromethyl)-4,7-dihydropyrazolo[1,5-a]pyrimidine-6-sulfonamide was obtained as a white solid. LC-MS found: $(M+1)^+$= 483.08.

Example 55

N-Benzyl-7-(4-chlorophenyl)-2,5-dimethyl-4,7-dihydropyrazolo[1,5-a]pyrimidine-6-sulfonamide Isomer 1: K$_v$1.5% inhibition: 22.9% at 0.3 μM Isomer 2: K$_v$1.5% inhibition: 17.2% at 0.3 μM

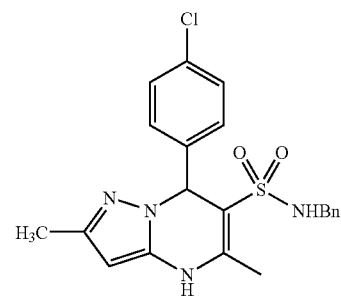

Following a procedure similar to that described in Example 53, N-benzyl-7-(4-chlorophenyl)-2,5-dimethyl-4,7-dihydropyrazolo[1,5-a]pyrimidine-6-sulfonamide was obtained as a white solid. LC-MS found: $(M+1)^+$=429.08.

Example 56

N-Benzyl-7-(3,4-dichlorophenyl)-5-methyl-2-(trifluoromethyl)-4,7-dihydropyrazolo[1,5-a]pyrimidine-6-sulfonamide Isomer 1: K$_v$1.5% inhibition: 50% at 0.3 μM Isomer 2: K$_v$1.5% inhibition: 37.5% at 0.3 μM

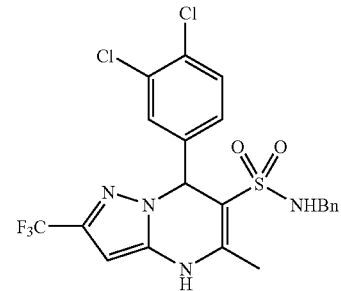

Following a procedure similar to that described in Example 53, N-benzyl-7-(3,4-dichlorophenyl)-5-methyl-2-(trifluoromethyl)-4,7-dihydropyrazolo[1,5-a]pyrimidine-6-sulfonamide was obtained as a white solid. LC-MS found: $(M+1)^+$= 517.15.

Example 57

N-tert-Butyl-7-(4-chlorophenyl)-5-methyl-2-(trifluoromethyl)-4,7-dihydropyrazolo[1,5-a]pyrimidine-6-sulfonamide Racemate: K$_v$1.5% inhibition: 34.1% at 0.3 μM Isomer 1: K$_v$1.5% inhibition: 48.6% at 0.3 μM Isomer 2: K$_v$1.5% inhibition: 36.9% at 0.3 μM

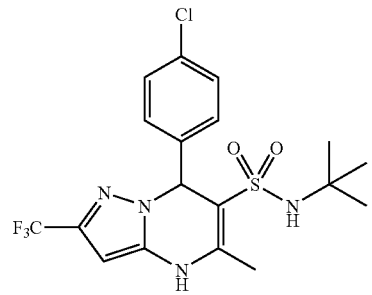

Following a procedure similar to that described in Example 53, N-tert-butyl-7-(4-chlorophenyl)-5-methyl-2-(trifluoromethyl)-4,7-dihydropyrazolo[1,5-a]pyrimidine-6-sulfonamide was obtained as a white solid. LC-MS found: $(M+1)^+$= 449.12.

Example 58

N-tert-Butyl-7-(3,4-dichlorophenyl)-5-methyl-2-(trifluoromethyl)-4,7-dihydropyrazolo[1,5-a]pyrimidine-6-sulfonamide Isomer 1: $K_v$1.5% inhibition: 42.9% at 0.3 μM
Isomer 2: $K_v$1.5% inhibition: 37.7% at 0.3 μM

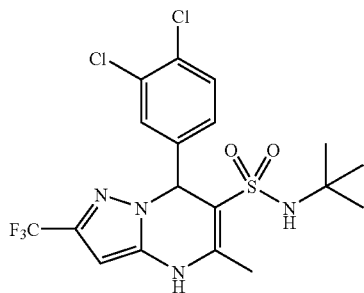

Following a procedure similar to that described in Example 53, N-tert-butyl-7-(3,4-dichlorophenyl)-5-methyl-2-(trifluoromethyl)-4,7-dihydropyrazolo[1,5-a]pyrimidine-6-sulfonamide was obtained as a white solid. LC-MS found: $(M+1)^+$= 483.1.

Example 59

7-(3,4-Dichlorophenyl)-5-methyl-6-(pyrrolidin-1-ylsulfonyl)-2-(trifluoromethyl)-4,7-dihydropyrazolo[1,5-a]pyrimidine Isomer 1: $K_v$1.5% inhibition: 89.8% at 0.3 μM
Isomer 2: $K_v$1.5% inhibition: 86.4% at 0.3 μM

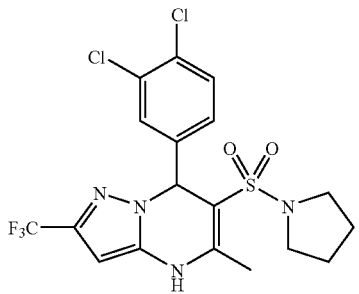

Following a procedure similar to that described in Example 53, 7-(3,4-dichlorophenyl)-5-methyl-6-(pyrrolidin-1-ylsulfonyl)-2-(trifluoromethyl)-4,7-dihydropyrazolo[1,5-a]pyrimidine was obtained as a white solid. LC-MS found: $(M+1)^+$= 481.0.

Example 60

7-(3,4-Dichlorophenyl)-N,2,5-trimethyl-N-phenyl-4,7-dihydropyrazolo[1,5-a]pyrimidine-6-sulfonamide Racemate: $K_v$1.5% inhibition: 83.2% at 0.3 μM

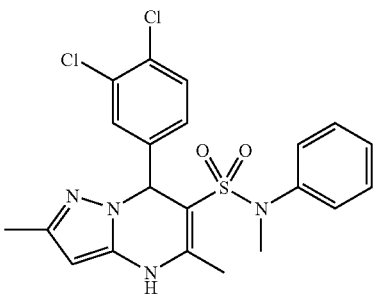

Following a procedure similar to that described in Example 53, 7-(3,4-dichlorophenyl)-N,2,5-trimethyl-N-phenyl-4,7-dihydropyrazolo[1,5-a]pyrimidine-6-sulfonamide was obtained as a white solid. LC-MS found: $(M+1)^+$=463.1.

Example 61

7-(3,4-Dichlorophenyl)-N,N-diethyl-2,5-dimethyl-4,7-dihydropyrazolo[1,5-a]pyrimidine-6-sulfonamide Isomer 1: $K_v$1.5% inhibition: 90.5% at 0.3 μM
Isomer 2: $K_v$1.5% inhibition: 42.3% at 0.3 μM

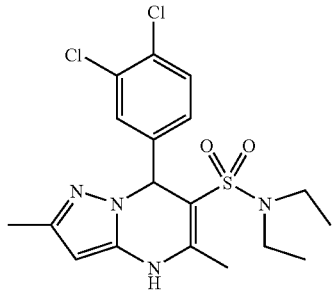

Following a procedure similar to that described in Example 53, 7-(3,4-dichlorophenyl)-N,N-diethyl-2,5-dimethyl-4,7-dihydropyrazolo[1,5-a]pyrimidine-6-sulfonamide was obtained as a white solid. LC-MS found: $(M+1)^+$=429.1.

Example 62

7-(3,4-Dichlorophenyl)-N,5-dimethyl-N-phenyl-2-(trifluoromethyl)pyrazolo[1,5-a]pyrimidine-6-sulfonamide Racemate: $K_v$1.5% inhibition: 12% at 0.3 μM

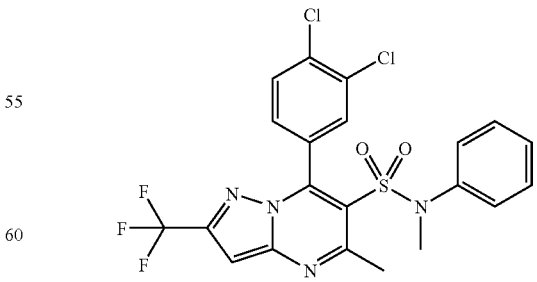

Following a procedure similar to that described in Example 53, a side product, 7-(3,4-dichlorophenyl)-N,5-dimethyl-N-phenyl-2-(trifluoromethyl)pyrazolo[1,5-a]pyrimidine-6-sulfonamide was obtained as a white solid. LC-MS found: $(M+1)^+$=515.01.

Example 63

7-(3,4-Dichlorophenyl)-N,5-dimethyl-N-phenyl-2-(trifluoromethyl)-4,7-dihydropyrazolo[1,5-a]pyrimidine-6-sulfonamide Isomer 1: K$_v$1.5% inhibition: 30% at 0.3 µM
Isomer 2: K$_v$1.5% inhibition: 31% at 0.3 µM

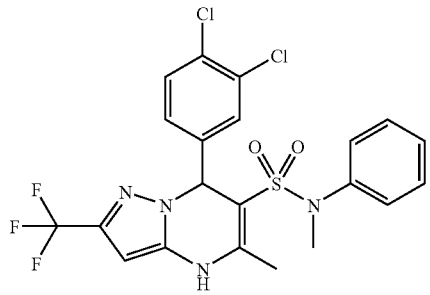

Following a procedure similar to that described in Example 53, 7-(3,4-dichlorophenyl)-N,5-dimethyl-N-phenyl-2-(trifluoromethyl)-4,7-dihydropyrazolo[1,5-a]pyrimidine-6-sulfonamide was obtained as a white solid. LC-MS found: (M+1)$^+$=517.00.

Example 64

7-(3,4-Dichlorophenyl)-N,N-diethyl-5-methyl-2-(trifluoromethyl)-4,7-dihydropyrazolo[1,5-a]pyrimidine-6-sulfonamide Isomer 1: K$_v$1.5% inhibition: 76.2% at 0.3 µM
Isomer 2: K$_v$1.5% inhibition: 60% at 0.3 µM

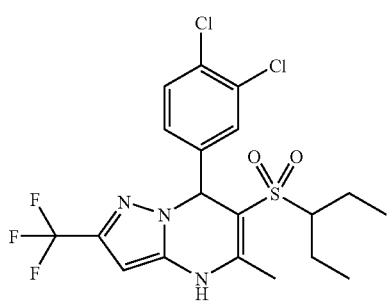

Following a procedure similar to that described in Example 53, 7-(3,4-dichlorophenyl)-N,N-diethyl-5-methyl-2-(trifluoromethyl)-4,7-dihydropyrazolo[1,5-a]pyrimidine-6-sulfonamide was obtained as a white solid. LC-MS found: (M+1)$^+$=483.0.

Example 65

7-(3,4-Dichlorophenyl)-5-methyl-6-(piperidin-1-ylsulfonyl)-2-(trifluoromethyl)-4,7-dihydropyrazolo[1,5-a]pyrimidine Isomer 1: K$_v$1.5% inhibition: 81% at 0.3 µM
Isomer 2: K$_v$1.5% inhibition: 78% at 0.3 µM

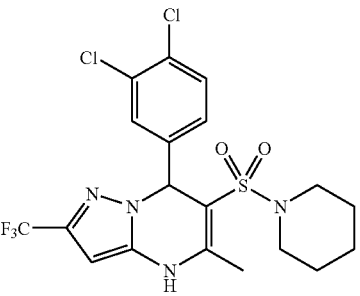

Following a procedure similar to that described in Example 53, 7-(3,4-dichlorophenyl)-5-methyl-6-(piperidin-1-ylsulfonyl)-2-(trifluoromethyl)-4,7-dihydropyrazolo[1,5-a]pyrimidine was obtained as a white solid. LC-MS found: (M+1)$^+$=495.0.

Example 66

7-(3,4-Dichlorophenyl)-5-methyl-6-(morpholinosulfonyl)-2-(trifluoromethyl)-4,7-dihydropyrazolo[1,5-a]pyrimidine Isomer 1: K$_v$1.5% inhibition: 51% at 0.3 µM
Isomer 2: K$_v$1.5% inhibition: 49% at 0.3 µM

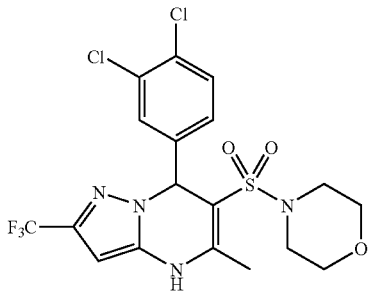

Following a procedure similar to that described in Example 53, 7-(3,4-dichlorophenyl)-5-methyl-6-(morpholinosulfonyl)-2-(trifluoromethyl)-4,7-dihydropyrazolo[1,5-a]pyrimidine was obtained as a white solid. LC-MS found: (M+1)$^+$=497.0.

Example 67

7-(4-Chlorophenyl)-5-methyl-6-(pyrrolidin-1-ylsulfonyl)-2-(trifluoromethyl)-4,7-dihydropyrazolo[1,5-a]pyrimidine Isomer 1: K$_v$1.5% inhibition: 60% at 0.3 µM
Isomer 2: K$_v$1.5% inhibition: 54% at 0.3 µM

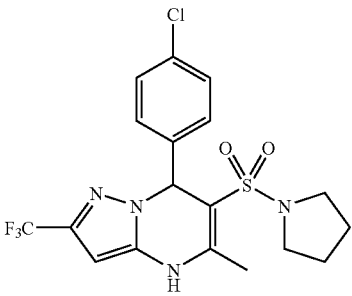

Following a procedure similar to that described in Example 53, 7-(4-chlorophenyl)-5-methyl-6-(pyrrolidin-1-ylsulfonyl)-2-(trifluoromethyl)-4,7-dihydropyrazolo[1,5-a]pyrimidine was obtained as a white solid. LC-MS found: (M+1)⁺= 447.1.

Example 68

7-(3,4-Dichlorophenyl)-2,5-dimethyl-6-(pyrrolidin-1-ylsulfonyl)-4,7-dihydro-[1,2,4]triazolo[1,5-a]pyrimidine Racemate: $K_v1.5$% inhibition: 7% at 0.3 μM

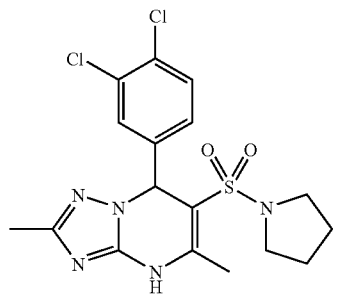

Following a procedure similar to that described in Example 53, 7-(3,4-dichlorophenyl)-2,5-dimethyl-6-(pyrrolidin-1-ylsulfonyl)-4,7-dihydro-[1,2,4]triazolo[1,5-a]pyrimidine was obtained as a white solid. LC-MS found: (M+1)⁺=428.0.

Example 69

3-Chloro-7-(3,4-dichlorophenyl)-2,5-dimethyl-6-(pyrrolidin-1-ylsulfonyl)-4,7-dihydropyrazolo[1,5-a]pyrimidine Isomer 1: $K_v1.5$% inhibition: 40% at 0.3 μM Isomer 2: $K_v1.5$% inhibition: 40% at 0.3 μM

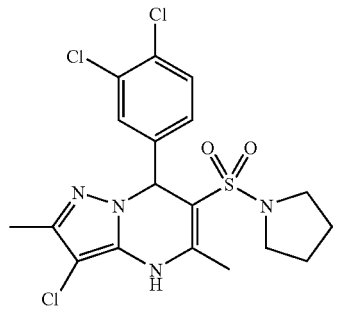

Following a procedure similar to that described in Example 53, 3-chloro-7-(3,4-dichlorophenyl)-2,5-dimethyl-6-(pyrrolidin-1-ylsulfonyl)-4,7-dihydropyrazolo[1,5-a]pyrimidine was obtained as a white solid. LC-MS found: (M+1)⁺=463.0.

Example 70

7-(3,4-Dichlorophenyl)-5-methyl-6-(4-phenylpiperazin-1-ylsulfonyl)-2-(trifluoromethyl)-4,7-dihydropyrazolo[1,5-a]pyrimidine Racemate: $K_v1.5$% inhibition: 26% at 0.3 μM

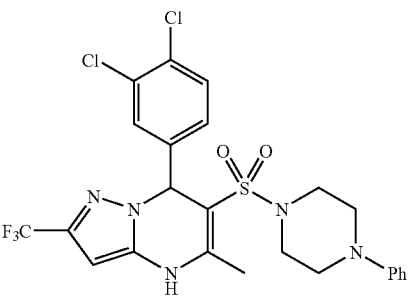

Following a procedure similar to that described in Example 53, 7-(3,4-dichlorophenyl)-5-methyl-6-(4-phenylpiperazin-1-ylsulfonyl)-2-(trifluoromethyl)-4,7-dihydropyrazolo[1,5-a]pyrimidine was obtained as a white solid. LC-MS found: (M+1)⁺=571.9.

Example 71

5-Methyl-7-(1-methyl-1H-indol-2-yl)-6-(pyrrolidin-1-ylsulfonyl)-2-(trifluoromethyl)-4,7-dihydropyrazolo[1,5-a]pyrimidine Racemate: $K_v1.5$% inhibition: 41% at 0.3 μM

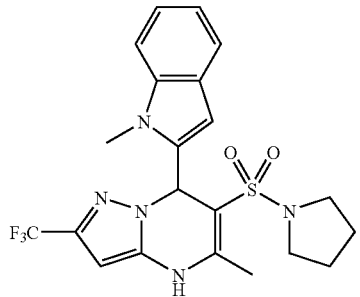

Following a procedure similar to that described in Example 53, 5-methyl-7-(1-methyl-1H-indol-2-yl)-6-(pyrrolidin-1-ylsulfonyl)-2-(trifluoromethyl)-4,7-dihydropyrazolo[1,5-a]pyrimidine was obtained as a white solid. LC-MS found: (M+1)⁺=466.0.

Example 72

6-(4-Chlorophenylsulfonyl)-5-methyl-7-(1-methyl-1H-indol-2-yl)-2-(trifluoromethyl)-4,7-dihydropyrazolo[1,5-a]pyrimidine Racemate: $K_v1.5$% inhibition: 34% at 0.3 μM

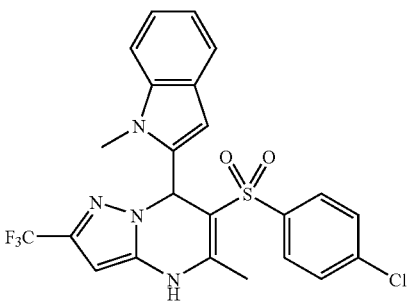

Following a procedure similar to that described in Example 53, 6-(4-chlorophenylsulfonyl)-5-methyl-7-(1-methyl-1H-indol-2-yl)-2-(trifluoromethyl)-4,7-dihydropyrazolo[1,5-a]pyrimidine was obtained as a white solid. LC-MS found: (M+1)$^+$=507.1.

Example 73

7-(3,4-Dichlorophenyl)-N-(4-methoxyphenylsulfonyl)-N,5-dimethyl-4,7-dihydropyrazolo[1,5-a]pyrimidine-6-carboxamide Racemate: K$_v$1.5% inhibition: 86% at 0.3 μM

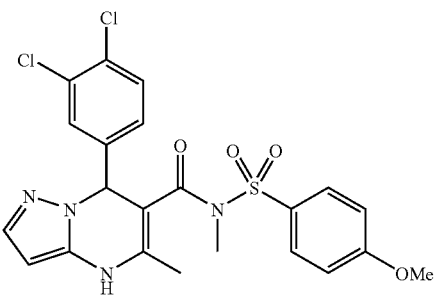

Step A: 4-(tert-Butoxycarbonyl)-7-(3,4-dichlorophenyl)-5-methyl-4,7-dihydropyrazolo[1,5-a]pyrimidine-6-carboxylic acid Following the procedure described in U.S. Pat. No. 6,706,720 B2, 4-(tert-butoxycarbonyl)-7-(3,4-dichlorophenyl)-5-methyl-4,7-dihydropyrazolo[1,5-a]pyrimidine-6-carboxylic acid was obtained as light yellow solid. LC-MS found: (M+1)$^+$=424.2.

Step B: tert-Butyl 7-(3,4-dichlorophenyl)-6-((4-methoxyphenylsulfonyl)carbamoyl)-5-methylpyrazolo[1,5-a]pyrimidine-4(7H)-carboxylate To a mixture of the product obtained from Step A (424 mg, 1.0 mmol), 4-methoxybenzene-sulfonamide (224 mg, 1.2 mmol), EDCl (230 mg, 1.2 mmol), in CH$_2$Cl$_2$ was added DMAP (146 mg, 1.2 mmol). The resulting mixture was stirred at room temperature under N$_2$ for 2.5 h. LC-MS indicated the completion of reaction. After reverse phase HPLC (acetonitrile/water) purification, the desired tert-butyl 7-(3,4-dichlorophenyl)-6-((4-methoxyphenylsulfonyl)carbamoyl)-5-methylpyrazolo[1,5-a]pyrimidine-4(7H)-carboxylate was obtained as white solid. LC-MS found: (M+1)$^+$=593.2.

Step C: tert-Butyl 7-(3,4-dichlorophenyl)-6-((4-methoxyphenylsulfonyl)-(methyl)carbamoyl)-5-methylpyrazolo[1,5-a]pyrimidine-4(7H)-carboxylate To a mixture of the product obtained from Step B (59.3 mg, 0.1 mmol) and iodomethane (excess) in DMF was added solid K$_2$CO$_3$ (excess). The mixture was stirred at room temperature under N$_2$ for 4 h. LC-MS indicated the completion of reaction. Most of the solvent was evaporated, and mixture was diluted with ethyl acetate, washed with water, brine and dried. After reverse phase HPLC (acetonitrile/water) purification, the desired tert-butyl 7-(3,4-dichlorophenyl)-6-((4-methoxyphenylsulfonyl)(methyl)carbamoyl)-5-methylpyrazolo[1,5-a]pyrimidine-4(7H)-carboxylate was obtained as white solid. LC-MS found: (M+1)$^+$=607.2.

Step D

To a mixture of the product obtained from Step C (60 mg, 0.1 mmol) in CH$_2$Cl$_2$ (5.0 mL) at room temperature under N$_2$ was added TFA (5.0 mL). The mixture was stirred for 1.5 h. LC-MS indicated the completion of reaction. Solvent was evaporated, and the mixture was purified by reverse phase HPLC (acetonitrile/water). The desired product was obtained as white solid. LC-MS found: (M+1)$^+$=507.2.

Example 74

7-(3,4-Dichlorophenyl)-N,5-dimethyl-N-(phenylsulfonyl)-4,7-dihydropyrazolo[1,5-a]pyrimidine-6-carboxamide Racemate: K$_v$1.5% inhibition: 79% at 0.3 μM

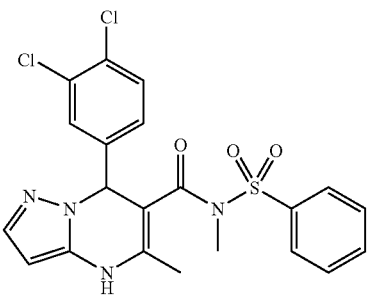

Following a procedure similar to that described in Example 73, 7-(3,4-dichlorophenyl)-N,5-dimethyl-N-(phenylsulfonyl)-4,7-dihydropyrazolo[1,5-a]pyrimidine-6-carboxamide was obtained as a white solid. LC-MS found: (M+1)$^+$=477.2.

Example 75

N-(4-Chlorophenylsulfonyl)-7-(3,4-dichlorophenyl)-N,5-dimethyl-4,7-dihydropyrazolo[1,5-a]pyrimidine-6-carboxamide Racemate: K$_v$1.5% inhibition: 89% at 0.3 μM

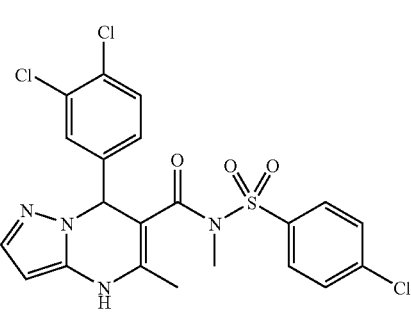

Following a procedure similar to that described in Example 73, N-(4-chlorophenylsulfonyl)-7-(3,4-dichlorophenyl)-N,5-dimethyl-4,7-dihydropyrazolo[1,5-a]pyrimidine-6-carboxamide was obtained as a white solid. LC-MS found: (M+1)$^+$=511.1.

Example 76

N-(7-Chloronaphthalen-2-ylsulfonyl)-7-(3,4-dichlorophenyl)-N,5-dimethyl-4,7-dihydropyrazolo[1,5-a]pyrimidine-6-carboxamide Racemate: K$_v$1.5% inhibition: 38% at 0.3 μM

73

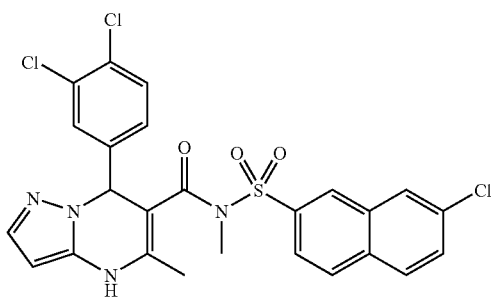

Following a procedure similar to that described in Example 73, N-(7-chloronaphthalen-2-ylsulfonyl)-7-(3,4-dichlorophenyl)-N,5-dimethyl-4,7-dihydropyrazolo[1,5-a]pyrimidine-6-carboxamide was obtained as a white solid. LC-MS found: $(M+1)^+=561.1$.

Example 77

7-(3,4-Dichlorophenyl)-N-(4-methoxyphenylsulfonyl)-N,2,5-trimethyl-4,7-dihydropyrazolo[1,5-a]pyrimidine-6-carboxamide Racemate: $K_v1.5$% inhibition: 0.172 µM

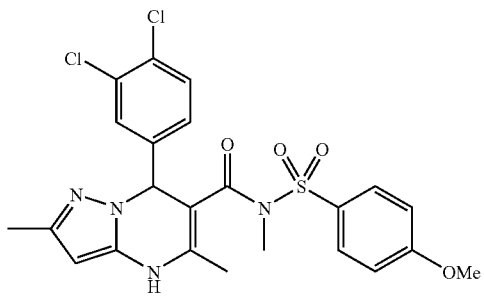

Following a procedure similar to that described in Example 73, 7-(3,4-dichlorophenyl)-N-(4-methoxyphenylsulfonyl)-N,2,5-trimethyl-4,7-dihydropyrazolo[1,5-a]pyrimidine-6-carboxamide was obtained as a white solid. LC-MS found: $(M+1)^+=521.2$.

Example 78

7-(3,4-Dichlorophenyl)-N,2,5-trimethyl-N-(phenylsulfonyl)-4,7-dihydropyrazolo[1,5-a]pyrimidine-6-carboxamide Racemate: $K_v1.5$% inhibition: 0.164 µM

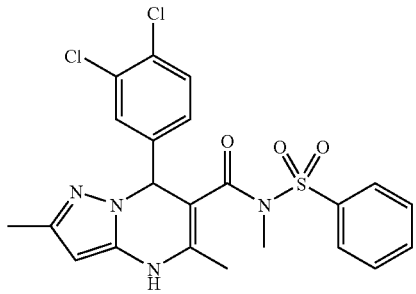

74

Following a procedure similar to that described in Example 73, 7-(3,4-dichlorophenyl)-N,2,5-trimethyl-N-(phenylsulfonyl)-4,7-dihydropyrazolo[1,5-a]pyrimidine-6-carboxamide was obtained as a white solid. LC-MS found: $(M+1)^+=491.2$.

Example 79

7-(3,4-Dichlorophenyl)-N,2,5-trimethyl-N-(phenylsulfonyl)-4,7-dihydropyrazolo[1,5-a]pyrimidine-6-carboxamide Isomer 1: $K_v1.5$% inhibition: 25% @0.3 µM Isomer 2: $K_v1.5$% inhibition: 88% @0.3 µM

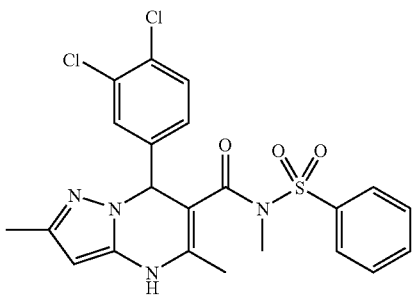

Following a procedure similar to that described in Example 73, 7-(3,4-dichlorophenyl)-N,2,5-trimethyl-N-(phenylsulfonyl)-4,7-dihydropyrazolo[1,5-a]pyrimidine-6-carboxamide was obtained as a white solid. LC-MS found: $(M+1)^+=491.2$.

Example 80

7-(3,4-Dichlorophenyl)-N-(4-fluorophenylsulfonyl)-N,2,5-trimethyl-4,7-dihydropyrazolo[1,5-a]pyrimidine-6-carboxamide Isomer 1: $K_v1.5$% inhibition: 37% @0.3 µM Isomer 2: $K_v1.5$% inhibition: 85% @0.3 µM

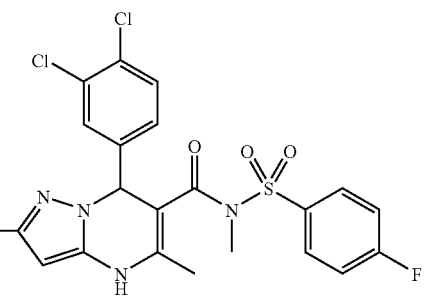

Following a procedure similar to that described in Example 73, 7-(3,4-dichlorophenyl)-N-(4-fluorophenylsulfonyl)-N,2,5-trimethyl-4,7-dihydropyrazolo[1,5-a]pyrimidine-6-carboxamide was obtained as a white solid. LC-MS found: $(M+1)^+=509.2$.

Example 81

7-(3,4-Dichlorophenyl)-N-(4-methoxyphenylsulfonyl)-N,2,5-trimethyl-4,7-dihydropyrazolo[1,5-a]pyrimidine-6-carboxamide Isomer 1: $K_v1.5$% inhibition: 16% @0.3 µM Isomer 2: $K_v1.5$% inhibition: 0.098 µM

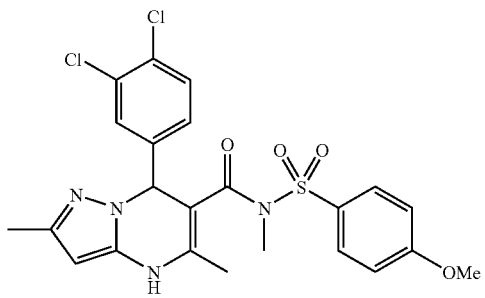

Following a procedure similar to that described in Example 73, 7-(3,4-dichlorophenyl)-N-(4-methoxyphenylsulfonyl)-N,2,5-trimethyl-4,7-dihydropyrazolo[1,5-a]pyrimidine-6-carboxamide was obtained as a white solid. LC-MS found: $(M+1)^+=521.2$.

Example 82

7-(3,4-Dichlorophenyl)-N-(4-fluorophenylsulfonyl)-N,5-dimethyl-2-(trifluoromethyl)-4,7-dihydropyrazolo[1,5-a]pyrimidine-6-carboxamide Racemate: $K_v1.5$% inhibition: 7% @0.3 µM

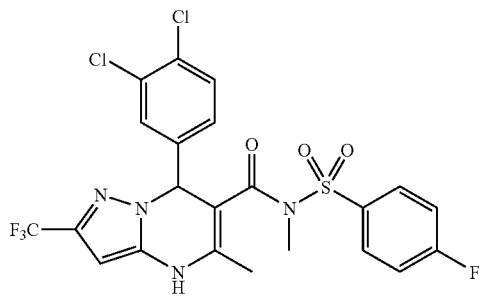

Following a procedure similar to that described in Example 73, 7-(3,4-dichlorophenyl)-N-(4-fluorophenylsulfonyl)-N,5-dimethyl-2-(trifluoromethyl)-4,7-dihydropyrazolo[1,5-a]pyrimidine-6-carboxamide was obtained as a white solid. LC-MS found: $(M+1)^+=563.2$.

Example 83

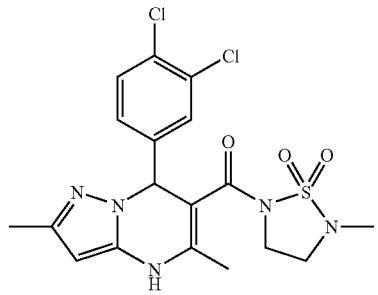

Racemate: $K_v1.5$% inhibition: 40% @0.3 µM

Following a procedure similar to that described in Example 73, the title compound was obtained as a white solid. LC-MS found: $(M+1)^+=456.2$.

Example 84

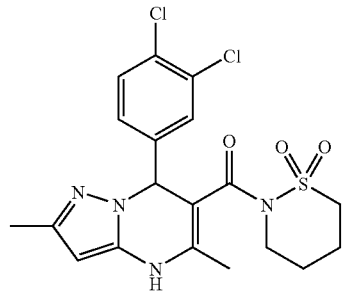

Isomer 1: $K_v1.5$% inhibition: 19% @0.3 µM

Isomer 2: $K_v1.5$% inhibition: 7% @0.3 µM

Following a procedure similar to that described in Example 73, the compound was obtained as a white solid. LC-MS found: $(M+1)^+=455.1$.

Example 85

N-(Butylsulfonyl)-7-(3,4-dichlorophenyl)-5-methyl-2-(trifluoromethyl)-4,7-dihydropyrazolo[1,5-a]pyrimidine-6-carboxamide Racemate: $K_v1.5$% inhibition: 11% @0.3 µM

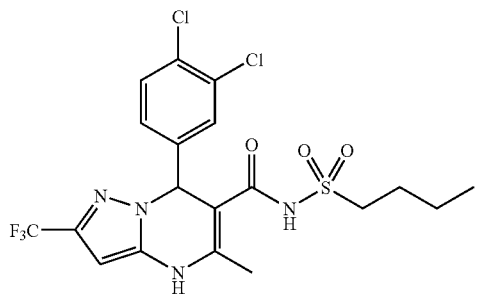

Following a procedure similar to that described in Example 73, N-(butylsulfonyl)-7-(3,4-dichlorophenyl)-5-methyl-2-(trifluoromethyl)-4,7-dihydropyrazolo[1,5-a]pyrimidine-6-carboxamide was obtained as a white solid. LC-MS found: $(M+1)^+=511.1$.

Example 86

N-(Butylsulfonyl)-7-(3,4-dichlorophenyl)-N,5-dimethyl-2-(trifluoromethyl)-4,7-dihydropyrazolo[1,5-a]pyrimidine-6-carboxamide Racemate: $K_v1.5$ $IC_{50}$: 0.242 µM

77

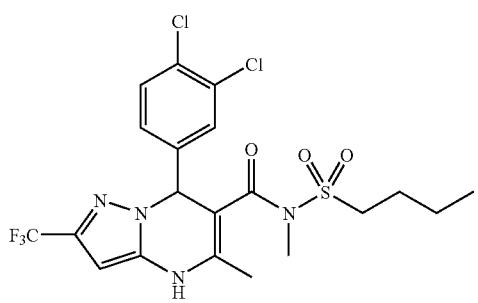

Following a procedure similar to that described in Example 73, N-(butylsulfonyl)-7-(3,4-dichlorophenyl)-N,5-dimethyl-2-(trifluoromethyl)-4,7-dihydropyrazolo[1,5-a]pyrimidine-6-carboxamide was obtained as a white solid. LC-MS found: (M+1)$^+$=525.1.

Example 87

7-(3,4-Dichlorophenyl)-N-(isopropylsulfonyl)-N,5-dimethyl-2-(trifluoromethyl)-4,7-dihydropyrazolo[1,5-a]pyrimidine-6-carboxamide Racemate: $K_v$1.5 IC$_{50}$: 0.259 µM

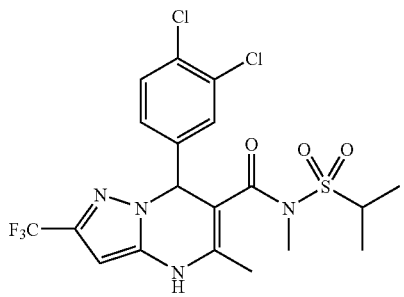

Following a procedure similar to that described in Example 73, 7-(3,4-dichlorophenyl)-N-(isopropylsulfonyl)-N,5-dimethyl-2-(trifluoromethyl)-4,7-dihydropyrazolo[1,5-a]pyrimidine-6-carboxamide was obtained as a white solid. LC-MS found: (M+1)$^+$=511.2.

Example 88

N-Cyclopropyl-7-(3,4-dichlorophenyl)-5-methyl-N-(propylsulfonyl)-2-(trifluoromethyl)-4,7-dihydropyrazolo[1,5-a]pyrimidine-6-carboxamide Racemate: $K_v$1.5% inhibition: 71% @0.3 µM

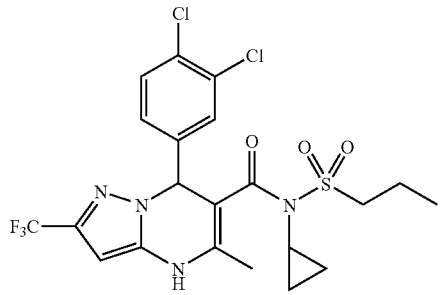

78

Following a procedure similar to that described in Example 73, N-cyclopropyl-7-(3,4-dichlorophenyl)-5-methyl-N-(propylsulfonyl)-2-(trifluoromethyl)-4,7-dihydropyrazolo[1,5-a]pyrimidine-6-carboxamide was obtained as a white solid. LC-MS found: (M+1)$^+$=537.1.

Example 89

N-(4-Chlorophenylsulfonyl)-7-(3,4-dichlorophenyl)-N,5-dimethyl-2-(trifluoromethyl)-4,7-dihydropyrazolo[1,5-a]pyrimidine-6-carboxamide Racemate: $K_v$1.5% inhibition: 40% @0.3 µM

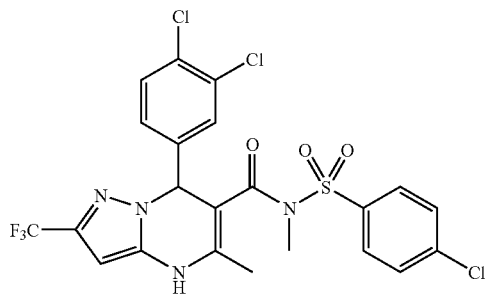

Following a procedure similar to that described in Example 73, N-(4-chlorophenylsulfonyl)-7-(3,4-dichlorophenyl)-N,5-dimethyl-2-(trifluoromethyl)-4,7-dihydropyrazolo[1,5-a]pyrimidine-6-carboxamide was obtained as a white solid. LC-MS found: (M+1)$^+$=579.0.

Example 90

7-(3,4-Dichlorophenyl)-N,5-dimethyl-N-(phenylsulfonyl)-2-(trifluoromethyl)-4,7-dihydropyrazolo[1,5-a]pyrimidine-6-carboxamide Isomer 1: $K_v$1.5% inhibition: 37% @0.3 µM Isomer 2: $K_v$1.5% inhibition: 51% @0.3 µM

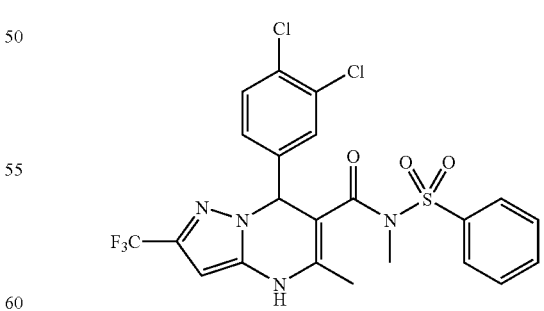

Following a procedure similar to that described in Example 73, 7-(3,4-dichlorophenyl)-N,5-dimethyl-N-(phenylsulfonyl)-2-(trifluoromethyl)-4,7-dihydropyrazolo[1,5-a]pyrimidine-6-carboxamide was obtained as a white solid. LC-MS found: (M+1)$^+$=545.1.

Example 91

7-(3,4-Dichlorophenyl)-N,5-dimethyl-N-(propylsulfonyl)-2-(trifluoromethyl)-4,7-dihydropyrazolo[1,5-a]pyrimidine-6-carboxamide Isomer 1: $K_v1.5$% inhibition: 72% @0.3 μM Isomer 2: $K_v1.5$% inhibition: 52% @0.3 μM

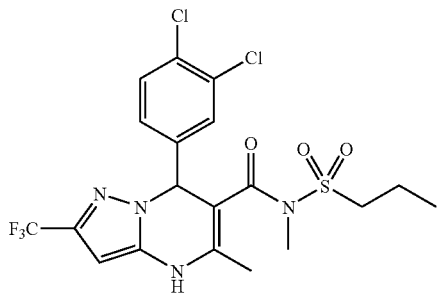

Following a procedure similar to that described in Example 73, 7-(3,4-dichlorophenyl)-N,5-dimethyl-N-(propylsulfonyl)-2-(trifluoromethyl)-4,7-dihydropyrazolo[1,5-a]pyrimidine-6-carboxamide was obtained as a white solid. LC-MS found: $(M+1)^+=525.1$.

Example 92

7-(3,4-Dichlorophenyl)-N,5-dimethyl-N-(phenylsulfonyl)-2-(trifluoromethyl)pyrazolo[1,5-a]pyrimidine-6-carboxamide Racemate: $K_v1.5$% inhibition: 41% @0.3 μM

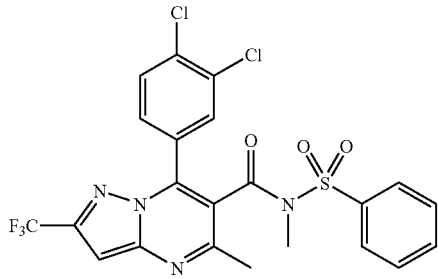

Following a procedure similar to that described in Example 73, 7-(3,4-dichlorophenyl)-N,5-dimethyl-N-(phenylsulfonyl)-2-(trifluoromethyl)pyrazolo[1,5-a]pyrimidine-6-carboxamide was obtained as a white solid. LC-MS found: $(M+1)^+=545.0$.

Example 93

N-(4-Chlorophenylsulfonyl)-7-(3,4-dichlorophenyl)-N-ethyl-5-methyl-2-(trifluoromethyl)-4,7-dihydropyrazolo[1,5-a]pyrimidine-6-carboxamide Isomer 1: $K_v1.5$% inhibition: 31% @0.3 μM Isomer 2: $K_v1.5$% inhibition: 27% @0.3 μM

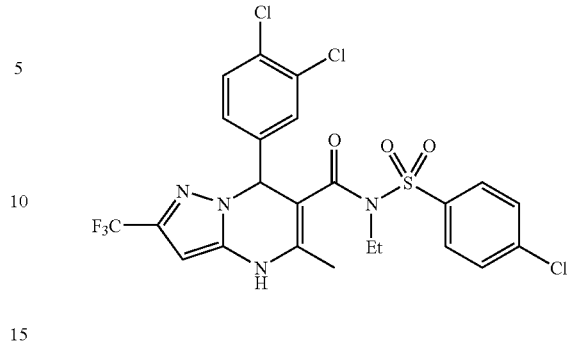

Following a procedure similar to that described in Example 73, N-(4-chlorophenylsulfonyl)-7-(3,4-dichlorophenyl)-N-ethyl-5-methyl-2-(trifluoromethyl)-4,7-dihydropyrazolo[1,5-a]pyrimidine-6-carboxamide was obtained as a white solid. LC-MS found: $(M+1)^+=593.1$.

Example 94

7-(3,4-Dichlorophenyl)-N-(3,5-dimethylisoxazol-4-ylsulfonyl)-N,2,5-trimethyl-4,7-dihydropyrazolo[1,5-a]pyrimidine-6-carboxamide Isomer 1: $K_v1.5$% inhibition: 80% @0.3 μM Isomer 2: $K_v1.5$% inhibition: 63% @0.3 μM

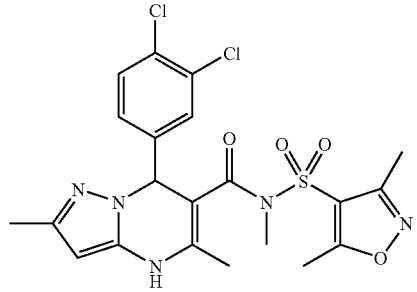

Following a procedure similar to that described in Example 73, 7-(3,4-dichlorophenyl)-N-(3,5-dimethylisoxazol-4-ylsulfonyl)-N,2,5-trimethyl-4,7-dihydropyrazolo[1,5-a]pyrimidine-6-carboxamide was obtained as a white solid. LC-MS found: $(M+1)^+=510.1$.

Example 95

7-(3,4-Dichlorophenyl)-N-(3,5-dimethylisoxazol-4-ylsulfonyl)-N,5-dimethyl-2-(trifluoromethyl)-4,7-dihydropyrazolo[1,5-a]pyrimidine-6-carboxamide Isomer 1: $K_v1.5$% inhibition: 91% @0.3 μM Isomer 2: $K_v1.5$% inhibition: 71% @0.3 μM

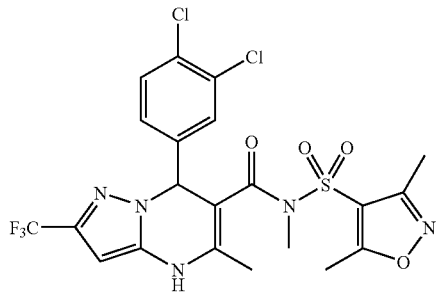

Following a procedure similar to that described in Example 73, 7-(3,4-dichlorophenyl)-N-(3,5-dimethylisoxazol-4-yl-sulfonyl)-N,5-dimethyl-2-(trifluoromethyl)-4,7-dihydropyrazolo[1,5-a]pyrimidine-6-carboxamide was obtained as a white solid. LC-MS found: (M+1)$^+$=564.0.

Example 96

7-(3,4-Dichlorophenyl)-N-(isopropylsulfonyl)-N,5-dimethyl-2-(trifluoromethyl)-4,7-dihydropyrazolo[1,5-a]pyrimidine-6-carboxamide Isomer 1: K$_v$1.5% inhibition: 57% @0.3 μM Isomer 2: K$_v$1.5% inhibition: 56% @0.3 μM

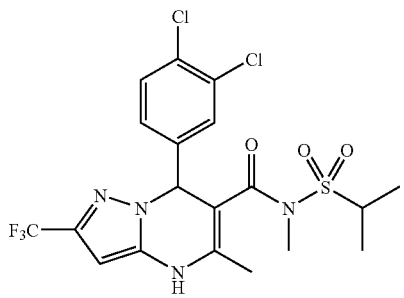

Following a procedure similar to that described in Example 73, 7-(3,4-dichlorophenyl)-N-(isopropylsulfonyl)-N,5-dimethyl-2-(trifluoromethyl)-4,7-dihydropyrazolo[1,5-a]pyrimidine-6-carboxamide was obtained as a white solid. LC-MS found: (M+1)$^+$=511.0.

Example 97

7-(3,4-Dichlorophenyl)-N-(3,5-dimethylisoxazol-4-ylsulfonyl)-N-ethyl-2,5-dimethyl-4,7-dihydropyrazolo[1,5-a]pyrimidine-6-carboxamide Isomer 1: K$_v$1.5% inhibition: 91% @0.3 μM Isomer 2: K$_v$1.5% inhibition: 50% @0.3 μM

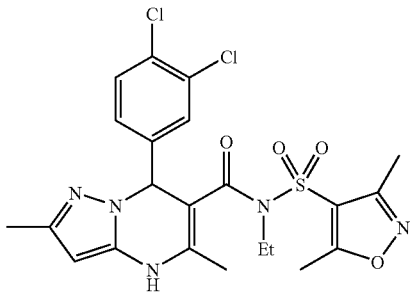

Following a procedure similar to that described in Example 73, 7-(3,4-dichlorophenyl)-N-(3,5-dimethylisoxazol-4-yl-sulfonyl)-N-ethyl-2,5-dimethyl-4,7-dihydropyrazolo[1,5-a]pyrimidine-6-carboxamide was obtained as a white solid. LC-MS found: (M+1)$^+$=524.0.

Example 98

N-(Cyclopropylsulfonyl)-7-(3,4-dichlorophenyl)-N,5-dimethyl-2-(trifluoromethyl)-4,7-dihydropyrazolo[1,5-a]pyrimidine-6-carboxamide Isomer 1: K$_v$1.5 IC$_{50}$: 0.112 μM Isomer 2: K$_v$1.5 IC$_{50}$: 0.200 μM

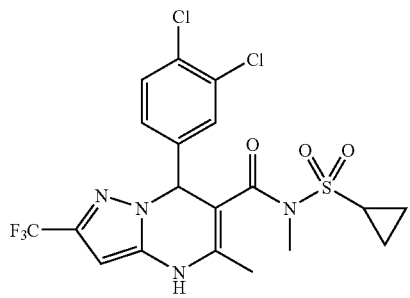

Following a procedure similar to that described in Example 73, N-(cyclopropylsulfonyl)-7-(3,4-dichlorophenyl)-N,5-dimethyl-2-(trifluoromethyl)-4,7-dihydropyrazolo[1,5-a]pyrimidine-6-carboxamide was obtained as a white solid. LC-MS found: (M+1)$^+$=509.1.

Example 99

7-(3,4-Dichlorophenyl)-6-((R)-3-methoxypyrrolidin-1-ylsulfonyl)-5-methyl-2-(trifluoromethyl)-4,7-dihydropyrazolo[1,5-a]pyrimidine Isomer 1: K$_v$1.5 IC$_{50}$: 86% @ 0.3 μM Isomer 2: K$_v$1.5 IC$_{50}$: 80% @ 0.3 μM

83

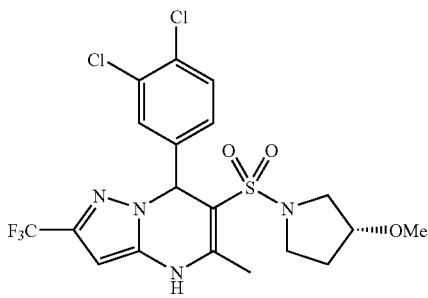

Following a procedure similar to that described in Example 53, 7-(3,4-dichlorophenyl)-6-((R)-3-methoxypyrrolidin-1-ylsulfonyl)-5-methyl-2-(trifluoromethyl)-4,7-dihydropyrazolo[1,5-a]pyrimidine was obtained as a white solid. LC-MS found: $(M+1)^+=511.0$.

What is claimed is:
1. A compound having the structure

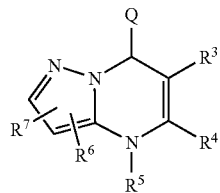

or stereoisomers thereof or a pharmaceutically acceptable salt thereof,
wherein Q is alkyl, substituted alkyl, cycloalkyl, substituted cycloalkyl, cycloheteroalkyl, substituted cycloheteroalkyl,
or

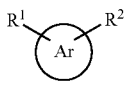

which is aryl, substituted aryl, heteroaryl or substituted heteroaryl;

$R^1$ and $R^2$ are the same or different and are independently selected from H, alkyl, substituted alkyl, halogen, carbocyclo, substituted carbocyclo, aryl, substituted aryl, heterocyclo, substituted heterocyclo, alkenyl, substituted alkenyl, alkynyl or substituted alkynyl, $CO_2R^a$, $CONR^bR^c$, $NR^dR^e$, $So_2NR^fR^g$ or $SO_2R^hR^i$ where $R^a$, $R^b$, $R^c$, $R^d$, $R^e$, $R^f$, $R^g$, $R^h$ and $R^i$ are the same or different and are independently selected from H, alkyl or aryl;

$R^3$ is

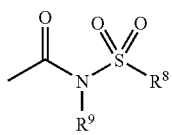

84 where $R^8$ is aryl, substituted aryl, carbocyclo, substituted carbocyclo, alkenyl, substituted alkenyl, alkynyl, substituted alkynyl, alkyl, substituted alkyl, heterocyclo, or substituted heterocyclo; and $R^9$ is H, alkyl, substituted alkyl, cycloalkyl or substituted cycloalkyl;

and wherein $R^8$ and $R^9$ together with the atoms to which they are bonded may optionally form a heterocyclic group or a substituted heterocyclic group;

$R^4$ is alkyl or substituted alkyl;

$R^5$ is H, alkyl or substituted alkyl;

$R^6$ and $R^7$ are the same or different and are independently selected from H, alkyl, substituted alkyl or polyhaloalkyl;

wherein the term "substituted alkyl" refers to alkyl groups substituted with one or more groups selected from alkyl, aryl (optionally substituted), substituted aryl, heterocyclo, substituted heterocyclo, carbocyclo, substituted carbocyclo, halo, hydroxy, arylalkoxy (optionally substituted), alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, and sulfonyl;

the term "substituted alkenyl" refers to alkenyl groups substituted with one or more groups selected from alkyl, substituted alkyl, aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, and sulfonyl;

the term "substituted alkynyl" refers to alkynyl groups substituted with one or more groups selected from alkyl, substituted alkyl, aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, and sulfonyl;

the term "substituted aryl" refers to aryl groups substituted with one or more groups selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, and sulfonyl, where optionally one or more pair of substituents may together with the atoms to which they are bonded form a 3 to 7 member ring;

the terms "substituted carbocyclo", "substituted cycloalky" and "refer to cycloalkyl groups " refer to cycloalkyl groups and cycloalkenyl groups substituted with one or more groups selected from alkyl, substututed alkyl, aryl substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, and sulfonyl; and the terms "substituted heterocyclo", "substituted cycloheteroalkyl" and "substituted heteroaryl" refer to heterocyclo, cycloheteroalkyl and heteroaryl groups, respectively, substituted with one or more groups selected from alkyl, substituted alkyl, alkenyl, oxo aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, and sulfonyl, where optionally one or more pair of substituents together with the atoms to which they are bonded form a 3 to 7 member ring.

2. The compound as defined in claim 1 wherein Q is

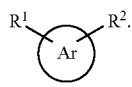

3. The compound as defined in claim 2 wherein at least one of $R^1$ and $R^2$ is other than H.

4. The compound as defined in claim 2 wherein

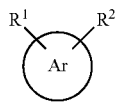

is phenyl.

5. The compound as defined in claim 2 wherein $R^1$ and $R^2$ are independently selected from H, halogen or alkyl.

6. The compound as defined in claim 1 wherein $R^4$ is alkyl, $R^5$ is H, $R^6$ is H, alkyl or trifluoromethyl, and $R^7$ is H.

7. The compound as defined in claim 2 wherein $R^3$ is

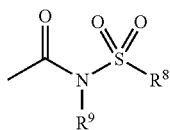

wherein $R^8$ is phenyl, alkyiphenyl, dialkyiphenyl, halophenyl, alkyl, alkoxyphenyl, dialkoxyphenyl, heteroaryl, dialkylbeteroaryl, cycloheteroalkyl, or cycloalkyl; and $R^9$ is alkyl or cycloalkyl.

8. The compound as defined in claim 2 wherein

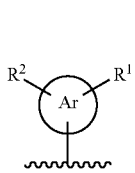 is 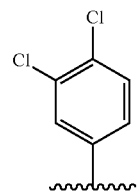; and $R^3$ is

-continued

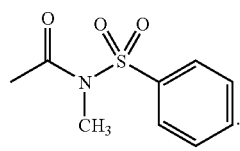

9. The compound as defined in claim 2 wherein Q is

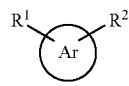

which is aryl (optionally substituted) or heteroaryl (optionally substituted);

$R^1$ is halogen or alkyl;

$R^2$ is halogen or hydrogen;

$R^3$ is

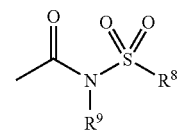

where $R^8$ is alkyl, alkoxyphenyl, phenyl, halophenyl, heteroaryl, dialkyiheteroaryl, cycloheteroalkyl, or cycloalkyl, and $R^9$ is alkyl or cycloalkyl, $R^4$ is alkyl or substituted alkyl $R^5$ is hydrogen;

$R^6$ is alkyl, hydrogen or trifluoromethyl; and $R^7$ is hydrogen.

10. The compound as defined in claim 9 wherein

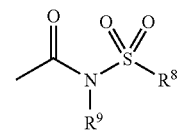

$R^3$ is where

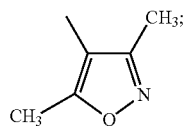

$R^8$ is heteroaryl which is and $R^9$ is cycloalkyl which is cyclopropyl.

11. The compound as defined in claim 2 wherein Q is which is phenyl,
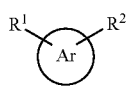
$R^1$ and $R^2$ are each chlorine, fluorine or methyl;
$R^3$ is
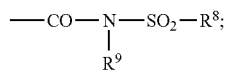
$R^8$ is substituted phenyl;
$R^9$ is methyl, ethyl, i-propyl or cyclopropyl;
$R^4$ is methyl;
$R^5$ is H;
$R^6$ is H, $CF_3$ or $CH_3$; and
$R^7$ is H.
12. The compound as defined in claim 1 having the structure
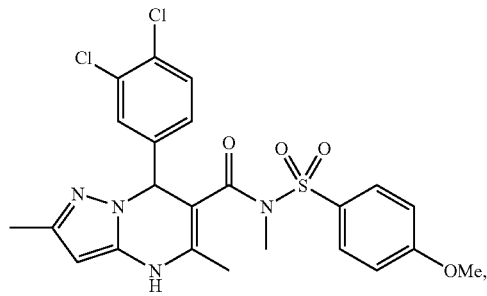
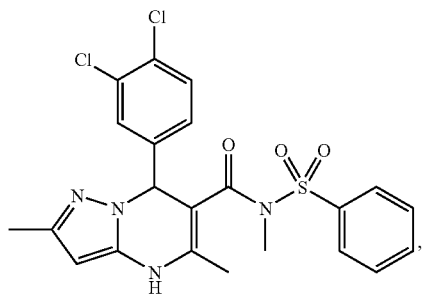
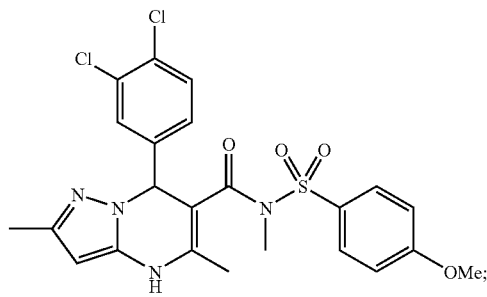
-continued
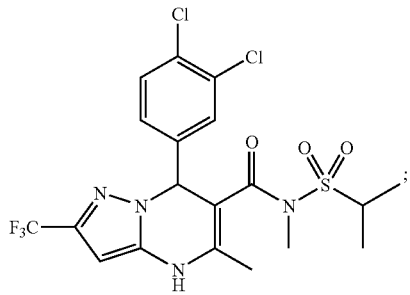
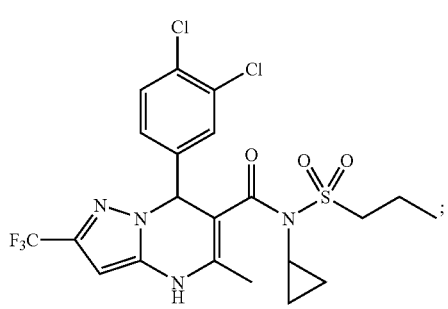
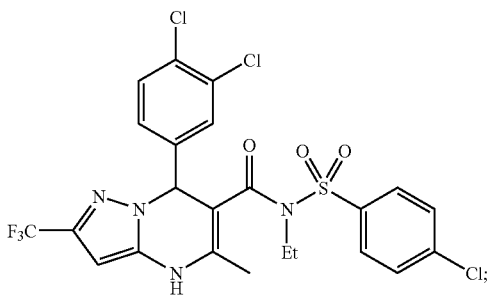
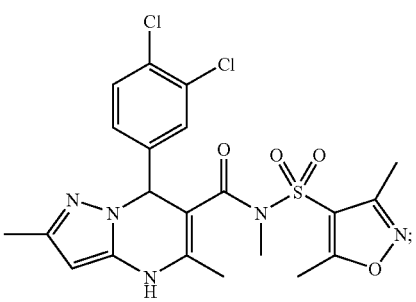
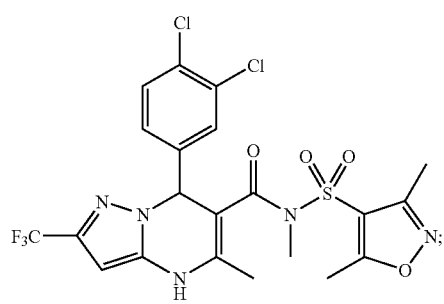

-continued
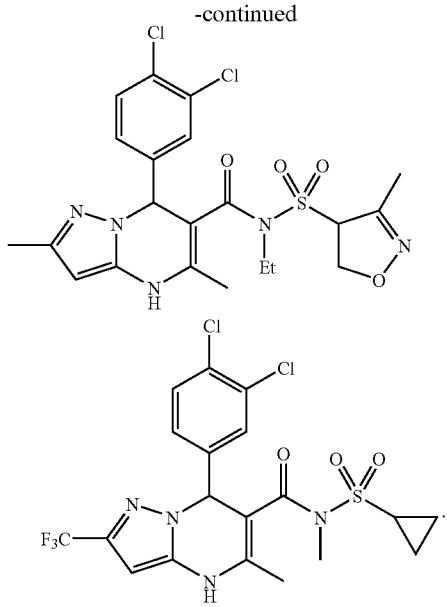
or
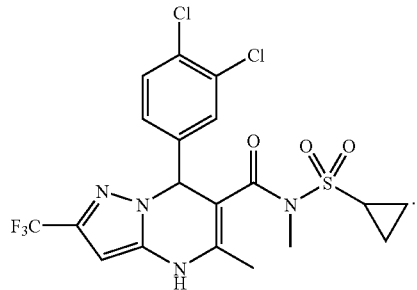
13. The compound as defined in claim 1 having the structure
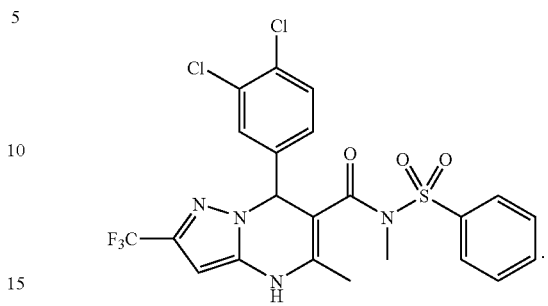
14. A pharmaceutically composition comprising a compound as defined in claim 1 and a pharmaceutically acceptable carrier thereof.
* * * * *

UNITED STATES PATENT AND TRADEMARK OFFICE
CERTIFICATE OF CORRECTION

PATENT NO.       : 7,507,730 B2                                          Page 1 of 3
APPLICATION NO. : 11/511154
DATED            : March 24, 2009
INVENTOR(S)      : Wei Han and Zilun Hu It is certified that error appears in the above-identified patent and that said Letters Patent is hereby corrected as shown below:

On the Title Page, (Title)
Line 2, "PYRAZOLO[1,5-A]PYRIMIDINES" should read -- PYRAZOLO[1,5-a]-PYRIMIDINES --.

Column 1
Line 2, "PYRAZOLO[1,5-A]PYRIMIDINES" should read -- PYRAZOLO[1,5-a]-PYRIMIDINES --.
Line 4, Please insert the following heading under the title of the invention:
-- CROSS-REFERENCE TO RELATED APPLICATION --.

Column 72
Lines 23-24, "$(CH_2)_rNR^{12f}R^{12}f$," should read -- $(CH_2)_rNR^{12f}, R^{12f}$, --;
Line 32, "$C(O)NR^{14c}R^{14c}$," should read -- $—C(O)NR^{14c}R^{14c}$, --;
Line 38, "$—C(O)NR^{16c}CR^{16c}$," should read -- $—C(O)NR^{16c}R^{16c}$, --;
Line 61, "$NR^{16c}R^{16c}$," should read -- $—NR^{16c}R^{16c}$, --.

Column 73
Line 14, "0-5 $R^{6e}$," should read -- 0-5 $R^{6e}$; --.

Column 76
Lines 9-10, after "being" delete "restinosis, organ transplantation, and cancer." and insert -- selected from multiple sclerosis, atherosclerosis, and rheumatoid arthritis. --.

Column 83
Line 34, "phannaceutically" should read -- pharmaceutically --;
Line 55, "$So_2NR^fR^g$or $SO_2R^hR^i$where" should read -- $SO_2NR^fR^g$ or $SO_2R^hR^i$ where --;
Line 56, "$R^h$and" should read -- $R^h$ and --;
Lines 60-65, after " 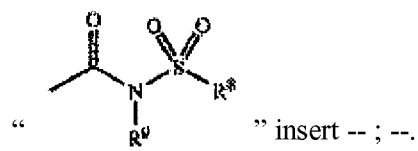 " insert -- ; --.

Signed and Sealed this

Thirtieth Day of November, 2010

David J. Kappos
*Director of the United States Patent and Trademark Office*

Column 84
Line 17, after "alkyl," insert -- substituted alkyl, --;
Line 18, after "substituted)," delete "substituted aryl,";
Line 53, "aroyl," should read -- aroyl --;
Lines 59-61, the terms "substituted carbocyclo", "substituted cycloalky" and "refer to cycloalkyl groups" refer to cycloalkyl groups and cycloalkenyl groups" should read -- the terms "substituted carbocyclo" and "substituted cycloalkyl" refer to cycloalkyl groups --;
Line 62, "substututed" should read -- substituted --;
Line 63, "aryl" should read -- aryl, --.

Column 85
Line 4, "heterocyclo" ," should read -- heterocyclo", --;
Line 8, "oxo" should read -- oxo, --;
Line 42, "H,alkyl" should read -- H, alkyl --;
Line 53, "alkyiphenyl, dialkyiphenyl," should read -- alkylphenyl, dialkylphenyl, --;
Lines 54-55, "dialkylbeteroaryl," should read -- dialkylheteroaryl, --;
Line 65, delete "$R^3$ is" and insert the same on Col. 85, Line 66 (Approx.).

Column 86
Line 25, "$R^3$is" should read -- $R^3$ is --;
Line 35, "dialkyiheteroaryl," should read -- dialkylheteroaryl, --;
Line 36, "$R^9$is" should read -- $R^9$ is --;
Line 37, after "substituted alkyl" insert -- ; --;
Lines 45-65, "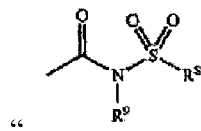

$R^3$ is
where

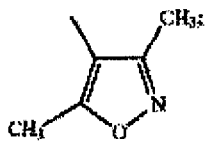

$R^8$ is heteroaryl which is"

should read

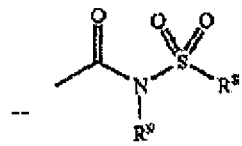

$R^3$ is
where

CERTIFICATE OF CORRECTION (continued)
U.S. Pat. No. 7,507,730 B2

$R^8$ is dialylheteroaryl which is 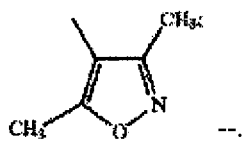 --.

Column 87

Line 1, after "is" insert --  --;

Lines 3-7, below "phenyl," delete "  ";
Line 11, "$R^{3\ is}$" should read -- $R^3$ is--;
Line 21, "$R^4$is" should read -- $R^4$ is --;
Lines 55-65, delete the following structure:

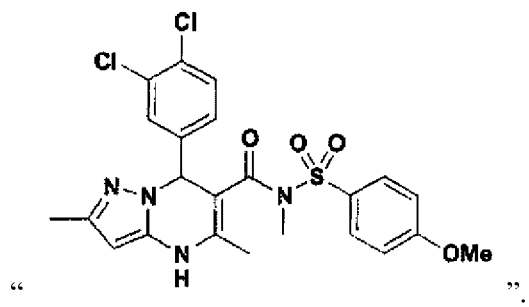

Column 90
Line 20, "pharmaceutically" should read -- pharmaceutical --.